(12) United States Patent
Lee et al.

(10) Patent No.: US 11,058,700 B2
(45) Date of Patent: Jul. 13, 2021

(54) MACROCYCLIC LACTONES AND USES THEREOF AS MODULATORS OF PURINERGIC RECEPTORS

(71) Applicant: City of Hope, Duarte, CA (US)

(72) Inventors: Peter P. Lee, San Marino, CA (US); Dobrin Draganov, San Dimas, CA (US)

(73) Assignee: City of Hope, Duarte, CA (US)

( * ) Notice: Subject to any disclaimer, the term of this patent is extended or adjusted under 35 U.S.C. 154(b) by 217 days.

(21) Appl. No.: 15/338,158

(22) Filed: Oct. 28, 2016

(65) Prior Publication Data

US 2017/0119807 A1    May 4, 2017

Related U.S. Application Data

(60) Provisional application No. 62/247,661, filed on Oct. 28, 2015.

(51) Int. Cl.
| | | |
|---|---|---|
| *A61K 31/7048* | (2006.01) | |
| *A61K 35/768* | (2015.01) | |
| *A61K 31/704* | (2006.01) | |
| *A61K 31/337* | (2006.01) |

(52) U.S. Cl.
CPC ........ *A61K 31/7048* (2013.01); *A61K 31/337* (2013.01); *A61K 31/704* (2013.01); *A61K 35/768* (2013.01)

(58) Field of Classification Search
None
See application file for complete search history.

(56) References Cited

U.S. PATENT DOCUMENTS

| | | | |
|---|---|---|---|
| 4,144,352 A | 3/1979 | Putter | |
| 4,861,760 A | 8/1989 | Mazuel et al. | |
| 4,911,920 A | 3/1990 | Jani et al. | |
| 5,212,162 A | 5/1993 | Missel et al. | |
| 5,403,841 A | 4/1995 | Lang et al. | |
| 6,696,483 B2 * | 2/2004 | Singh .................... | A61K 31/00 514/450 |
| 2009/0281175 A1 | 11/2009 | Kaoukhov et al. | |
| 2012/0225123 A1 * | 9/2012 | Schimmer .......... | A61K 31/7068 424/474 |

FOREIGN PATENT DOCUMENTS

| | | | |
|---|---|---|---|
| WO | WO-2012/150543 A1 | 11/2012 | |
| WO | WO-2013095286 A2 * | 6/2013 | ........... A61K 31/192 |

OTHER PUBLICATIONS

Liu et al. "Increasing Avermectin Production in Streptomyces avermitilis by Manipulating the Expression of a Novel TetR-Family Regulator and Its Target Gene Product", Applied and Environmental Microbiology, Aug. 2015. 81(15):5157-5173. (Year: 2015).*

Jacob LS. "Chapter 11: Cancer Chemotherapy". Pharmacology (Fourth Edition). Williams & Wilkins. 1996. pp. 253-274. (Year: 1996).*

Fajardo et al. Abstract 1024: Targeting PAK1 Activity in Breast Cancer: Inhibition of Cell Growth, Survival, Motility, and Signaling. Proceedings: AACR 106th Annual Meeting 2015; Apr. 18-22, 2015; 75(15 Suppl): Abstract 1024. (Year: 2015).*

Hashimoto et al. "Ivermectin Inactivates the Kinase PAK1 and Blocks the PAK1-Dependent Growth of Human Ovarian Cancer and NF2 Tumor Cell Lines". Drug Discov Ther. 2009; 3(6):243-246. (Year: 2009).*

Nanda et al. Abstract S1-09: A Phase Ib Study of Pembrolizumab (MK-3475) in Patients with Advanced Triple-Negative Breast Cancer. Proceedings of the Thirty-Seventh Annual CTRC-AACR San Antonio Breast Cancer Symposium: Dec. 9-13, 2014; San Antonio, TX. Cancer Res 2015;75(9 Suppl) Abstract S1-09. (Year: 2015).*

Yang et al. "Mouse Models for Tumor Metastasis". Methods Mol Biol. 2012; 928:221-228. (Year: 2012).*

Gunturi et al. "Nivolumab for the Treatment of Cancer". Expert Opinion on Investigational Drugs. 2015; 24(2):253-260, Published Online Dec. 12, 2014. (Year: 2014).*

Holliday et al. "Choosing the Right Cell Line for Breast Cancer Research". Breast Cancer Research. 2011, 13:215. (Year: 2011).*

Luo et al. "Expression of MAS1 In Breast Cancer". Cancer Sci. Jun. 7, 2015; 106:1240-1248. (Year: 2015).*

Melotti et al. "The River Blindness Drug Ivermectin and Related Macrocyclic Lactones Inhibit WNT-TCF Pathway Responses in Human Cancer". EMBO Mol Med. 2014; 6:1263-1278. (Year: 2014).*

Adinolfi, E. et al. (Jun. 15, 2012, e-published Apr. 13, 2012). "Expression of P2X7 receptor increases in vivo tumor growth," *Cancer Res* 72(12):2957-2969.

Burnstock, G. et al. (Dec. 2013). "Purinergic signalling and cancer," *Purinergic Signal* 9(4):491-540.

Crump, A. (May 2017, e-published Feb. 15, 2017). "Ivermectin: enigmatic multifaceted 'wonder' drug continues to surprise and exceed expectations," *J Antibiot* 70(5):495-505.

Dixon, C.J. et al. (1997). "Extracellular nucleotides stimulate proliferation in MCF-7 breast cancer cells via P2-purinoceptors," *Br J Cancer* 75(1):34-39.

Drinyaev, V.A. et al. (Oct. 6, 2004). "Antitumor effect of avermectins," *Eur J Pharmacol* 501(1-3):19-23.

Furusawa, S. et al. (2000). "Potentiation of Doxorubicin-Induced Apoptosis of Resistant Mouse Leukaemia Cells by Ivermectin," *Pharm Pharmacol Commun* 6:129-134.

Korystov, Y.N. et al. (Jun. 16, 2004). "Avermectins inhibit multidrug resistance of tumor cells," Eur J Pharmacol 493(1-3):57-64.

Martins, I. et al. (Jan. 2014, e-published Jul. 12, 2013). "Molecular mechanisms of ATP secretion during immunogenic cell death," *Cell Death Differ* 21(1):79-91.

Melotti, A. et al. (Oct. 2014). "The river blindness drug Ivermectin and related macrocyclic lactones inhibit WNT-TCF pathway responses in human cancer," *EMBO Mol Med* 6(10):1263-1278.

(Continued)

*Primary Examiner* — Leslie A. Royds Draper
(74) *Attorney, Agent, or Firm* — Mintz Levin Cohn Ferris Glovsky and Popeo, P.C.

(57) ABSTRACT

Described herein, inter alia, are macrocyclic lactones such as ivermectin and methods for their use in treating, for example, hyperproliferative disorders such as cancer.

5 Claims, 50 Drawing Sheets

Specification includes a Sequence Listing.

(56) References Cited

OTHER PUBLICATIONS

Pellegatti, P. et al. (Jul. 9, 2008). "Increased level of extracellular ATP at tumor sites: in vivo imaging with plasma membrane luciferase," *PLoS One* 3(7):e2599.

Seil. M. et al. (Dec. 2010, e-published Nov. 20, 2010). "Ivermectin-dependent release of IL-1 beta in response to ATP by peritoneal macrophages from P2X(7)-KO mice," *Purinergic Signal* 6(4):405-416.

Sharmeen, S. et al. (Nov. 4, 2010, e-published Jul. 19, 2010). "The antiparasitic agent ivermectin induces chloride-dependent membrane hyperpolarization and cell death in leukemia cells," *Blood* 116(18):3593-3603.

Zemkova, H. et al. (2014). "Allosteric modulation of ligand gated ion channels by ivermectin," *Physiol Res* 63 Suppl 1:S215-224.

\* cited by examiner

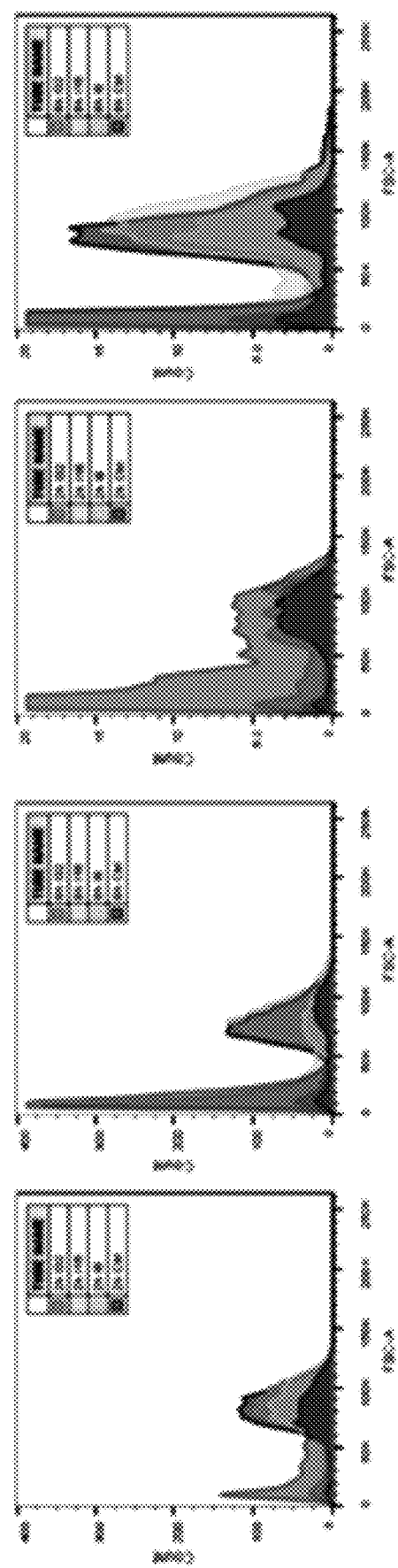
FIG. 9C - cont.

FIG. 10G

| GSE41445BCDataset | | T.TTEST | AvgNorm | AvgBC |
|---|---|---|---|---|
| P2XRs | P2RX1 | 1.79E-45 | 7.90 | 6.95 |
| | P2RX2 | 0.0224 | 6.38 | 5.91 |
| | P2RX3 | 0.1710 | 6.07 | 5.66 |
| | P2RX4 | 7.44E-3 | 7.06 | 6.74 |
| | P2RX5 | 5.09E-5 | 8.69 | 7.56 |
| | P2RX6 | 0.0969 | 6.79 | 6.48 |
| | P2RX7 | 1.71E-5 | 4.47 | 5.03 |
| P2YRs | P2RY1 | 0.160 | 4.27 | 3.71 |
| | P2RY2 | 7.01E-5 | 6.86 | 7.82 |
| | P2RY4 | 0.466 | 5.75 | 5.87 |
| | P2RY12 | 0.319 | 3.66 | 3.71 |
| | P2RY14 | 0.376 | 3.11 | 3.18 |
| | LTB4R | 0.0201 | 6.95 | 6.79 |
| | LPAR6 | 0.841 | 4.77 | 4.74 |
| | GPR17 | 0.887 | 5.04 | 4.69 |
| | P2RY10 | 0.357 | 4.75 | 4.84 |
| | P2RY8 | 0.0782 | 5.13 | 5.48 |
| | LPAR4 | 0.468 | 3.85 | 3.77 |
| | P2RY13 | 0.514 | 5.07 | 4.85 |
| | OXGR1 | 6.94E-3 | 4.50 | 5.00 |
| NOXs | NOX4 | 2.93E-3 | 4.71 | 3.89 |
| | NOX1 | 0.259 | 5.72 | 5.64 |
| | NOX5 | 0.0585 | 6.85 | 6.10 |
| | NOX3 | 0.397 | 4.70 | 4.72 |
| | NOX2 | 0.120 | 5.35 | 4.92 |
| | DUOX1 | 1.91E-3 | 6.21 | 5.45 |
| | DUOX2 | 4.71E-3 | 5.64 | 5.06 |
| GABARs | GABRA1 | 0.738 | 4.56 | 4.34 |
| | GABRA2 | 0.0834 | 4.24 | 3.75 |
| | GABRA3 | 0.152 | 5.39 | 5.22 |
| | GABRA4 | 0.0477 | 5.36 | 5.10 |
| | GABRA5 | 7.63E-3 | 4.69 | 4.32 |
| | GABRA6 | 0.0868 | 4.52 | 3.97 |
| Glycine Rs | GLRA1 | 0.0847 | 5.82 | 4.51 |
| | GLRA2 | 0.166 | 7.29 | 6.61 |
| | GLRA3 | 0.0890 | 3.58 | 3.39 |
| | GLRB | 0.286 | 5.32 | 5.46 |

MACROCYCLIC LACTONES AND USES THEREOF AS MODULATORS OF PURINERGIC RECEPTORS

CROSS-REFERENCES TO RELATED APPLICATIONS

This application claims the benefit of U.S. Provisional Application No. 62/247,661, filed Oct. 28, 2015, the contents of which is incorporated herein in its entirety and for all purposes.

STATEMENT AS TO RIGHTS TO INVENTIONS MADE UNDER FEDERALLY SPONSORED RESEARCH AND DEVELOPMENT

This invention was made with Government support under Grant Nos. W81XWH-11-1-0548 and W81XWH-12-1-0366 awarded by the Department of Defense. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 48440-593001US_ST25.TXT, created Oct. 26, 2016, 716 bytes, machine format IBM-PC, MS-Windows operating system, is hereby incorporated by reference.

BACKGROUND

Elevated levels of extracellular adenosine triphosphate (ATP) is one of the major characteristics of the tumor microenvironment. Exogenous ATP controls cellular and tissue defense/repair processes via signaling through purinergic receptors. High extracellular ATP levels also occur in vivo at sites of trauma, ischemia, or stroke and are associated with massive inflammatory responses and cell death (e.g. in excitable cells such as neurons). Thus, ATP can function as a prototypical danger signal that activates a potent immune response, but can also promote cancer progression.

Considering these examples of opposed functions, ATP/purinergic signaling appears to play a complex role within the tumor microenvironment. Tumor growth and survival appears to critically depend on optimal extracellular ATP levels, and displacing this balance from tumor-promoting to cytotoxic can serve as a therapy for cancer. Disclosed herein are solutions to these and other problems in the art.

BRIEF SUMMARY OF THE INVENTION

In an aspect is provided a method of treating cancer in a patient in need thereof, the method including administering a therapeutically effective amount of a macrocyclic lactone and a modulator of the ATP/P2X4/P2X7/Pannexin-1/Caspase-1 signaling pathway.

In an aspect is provided a method of treating cancer in a patient in need thereof, the method including administering a therapeutically effective amount of a macrocyclic lactone, or a pharmaceutically acceptable salt thereof, and a therapy selected from a reactive oxygen species inducing therapy, an ATP releasing therapy, an autophagy inducing therapy, irradiation therapy, cryoablation therapy, or thermal ablation therapy.

In an aspect is provided a method of treating cancer in a patient in need thereof, the method including administering a therapeutically effective amount of a macrocyclic lactone, or a pharmaceutically acceptable salt thereof, and an anti-cancer agent.

In an aspect is provided a method of treating cancer in a patient in need thereof, the method including administering a therapeutically effective amount of a macrocyclic lactone, or a pharmaceutically acceptable salt thereof, and a protein inhibitor selected from the group consisting of an mTOR inhibitor, an ER inhibitor, or an EGFR tyrosine kinase inhibitor.

In an aspect is provided a method of treating cancer in a patient in need thereof, the method including administering a therapeutically effective amount of a macrocyclic lactone, or a pharmaceutically acceptable salt thereof, and a bacterial agent.

In an aspect is provided a method of treating cancer in a patient in need thereof, the method including administering a therapeutically effective amount of a macrocyclic lactone, or a pharmaceutically acceptable salt thereof, and a virus (e.g. an oncolytic virus).

In an aspect is provided a method of treating cancer in a patient in need thereof, the method including administering a therapeutically effective amount of a macrocyclic lactone, or a pharmaceutically acceptable salt thereof, and an immunostimulant (e.g. an anti-cancer immunostimulant).

In an aspect is provided a pharmaceutical composition including a macrocyclic lactone, or pharmaceutically acceptable salt thereof, a second agent, and a pharmaceutically acceptable excipient, wherein the second agent is a modulator of the ATP/P2X4/P2X7/Pannexin-1/Caspase-1 signaling pathway, an anti-cancer agent, an mTOR inhibitor, an ER inhibitor, an EGFR tyrosine kinase inhibitor, a Toll-like receptor agonist, an RIG-I-like receptor agonist, a CD39 antagonist, a CD73 antagonist, a PD-1 inhibitor, a PD-L1 inhibitor, a PD-L2 inhibitor, a CTLA-4 inhibitor, a TIGIT inhibitor, a BTLA inhibitor, a LAG-3 inhibitor, a TIM-3 inhibitor, a 2B4 inhibitor, a CD160 inhibitor, a LIGHT/HVEM inhibitor, a GITR activator, an OX40 activator, a 41BB activator, an ICOS activator, a CD27 activator, a regulatory T cell depleting agent, or myeloid derived suppressor cell depleting agent.

BRIEF DESCRIPTION OF THE DRAWINGS

FIG. 1A: Mouse (4T1.2) and human (MDA-MB-231) TNBC cells manifest similar sensitivity to Ivermectin. Viability of cells treated with various doses of Ivermectin for 24 h. FIG. 1B: Extended exposure time reduces IC50 values to as low as 2 µM. 4T1.2 cells were seeded at 100 cells/well and individual colonies were counted after a week. Cancer cells were exposed to Ivermectin during the initial 24 h or during the entire duration of the assay. FIG. 1C: MDA-MB-231 breast cancer cells manifest higher sensitivity to Ivermectin compared to normal non-transformed human foreskin fibroblasts (HFFs). FIG. 1D: Flow cytometry analysis showing that cell death proceeds through two distinct pathways: a directly necrotic 7AAD-single positive or Annexin V/PS-single positive apoptotic pathway. FIG. 1E: Kinetics of necrotic versus apoptotic killing of 4T1.2 breast cancer cells. FIG. 1F: Ivermectin-induced cell death can be reversed by inhibition of various controlled cell death pathways. 4T1.2 cells were treated for 4 h with 32 µM Ivermectin in the presence of µM concentrations of Z-vad-fmk, Necrostatin-1, Digoxin, or VX-765, as indicated. FIG. 1G: Activation of Caspase-1, Caspase-3 and cleavage of PARP in 4T1.2 and MDA-MB- 231 cells treated with 32 µM for 4 h. Asterisk (*) indicates p<0.05 relative to untreated or Ivermectin alone controls, respectively. FIG. 1H: Western blot analysis showing constitutive and Ivermectin-induced cleavage of caspases 1 and 3 in murine (top) and human (bottom) breast cancer cells.

FIG. 2A: Ivermectin-induced ROS are $Ca^{2+}$-, ATP-, and P2X7-regulated. 4T1.2 cells were labeled with a ROS detection probe and treated for 1 h with 32 µM Ivermectin in the presence of 1 mM EDTA, 5mM NAC, 5 µM DPI, 2500 µunits/ml Apyrase, 3 mM ATP, and 10 µM KN-62. FIG. 2B: Ivermectin-induced cell death is transiently reversed by inhibition of NADPH oxidases with DPI (µM concentrations as indicated). Triangles (▲) indicate significant antagonism CI>1.0. FIG. 2C: Synergy between Ivermectin and $H_2O_2$- or irradiation-generated ROS, as well as the ROS-inducing chemotherapeutic agents paclitaxel (PTX) and doxorubicin (DOX). 4T1.2 cancer cells were irradiated (10-20 kRad) or treated with $H_2O_2$ (10-1000 µM), PTX (0.1-1 µM), or DOX (1-4 µM) and incubated with Ivermectin for 24 h/48 h. Circles (●) indicate significant synergy CI<1.0, see Table 1. Asterisk (*) indicates p<0.05 relative to untreated or Ivermectin alone controls, respectively.

FIG. 3A: Depletion of extracellular ATP with Apyrase (2500 µunits/ml) exacerbates killing of 4T1.2 cell by Ivermectin. FIG. 3B: Extracellular $Ca^{2+}$ and ATP contain Ivermectin-induced cell swelling. 4T1.2 cells were treated with 32 µM Ivermectin for 4 h in the presence of 1 mM EDTA or 2500 µunits/ml Apyrase. FIG. 3C: Ivermectin (0.5-32 µM) and high concentrations of extracellular ATP (0.3-3 mM) synergistically open pannexin-1 channels and permeabilize the membrane on live cells (7AAD-positive dead cells were gated out). 4T1.2 cells were treated for 30 min as indicated in the presence of 7 AAD and 5 µM YOPRO-1. FIG. 3D: Analysis of supernatants from Ivermectin-treated murine and human TNBC cells showing rapid release of ATP followed by its transient depletion. Depletion of extracellular ATP with Apyrase (2500 µunits/ml) was used as a positive control. FIG. 3E: Analysis of membrane-proximal ATP levels using cancer cells engineered to express a membrane-bound Luciferase. FIG. 3F: qPCR demonstrating over-expression of P2X4 and P2X7 receptors in mouse 4T1.2 breast cancer cells versus mouse embryonic fibroblasts (MEF). FIG. 3G: The P2X7-specific inhibitor KN-62 (1-10 µM) blocks Ivermectin cytotoxicity (IVM 8-32 µM, 4-48 h treatments). Asterisk (*) indicates p<0.05 relative to untreated or Ivermectin alone controls, respectively.

FIG. 4A: Kinetics of cytosolic $Ca^{2+}$ increase in 4T1.2 cells treated with Ivermectin. FIG. 4B: Inhibition of CaMKII is equally effective at blocking the initial cytotoxicity of Ivermectin. 4T1.2 cells were treated for 4 h with 32 µM Ivermectin in the presence of the P2X7/CaMKII dual inhibitor KN-62 or the CaMKII-specific inhibitor KN-63, at µM concentrations as indicated. FIG. 4C: Flow cytometry analysis of JC-1 loaded 4T1.2 cells showing that high doses of Ivermectin result in a sudden mitochondrial de-polarization, while lower doses cause similar effects but after transient hyper-polarization. FIG. 4D: MPTP contributes to Ivermectin. 4T1.2 cells were treated for 4 h with 32 µM Ivermectin in the presence of the MPTP inhibitor Cyclosporin A at µM concentrations as indicated. Asterisk (*) indicates p<0.05 relative to untreated or Ivermectin alone controls, respectively.

FIG. 5A: qPCR showing the extent of gene knockdown in 4T1.2 cells transfected with shRNA targeting the P2X7 receptor versus non-targeting (NT) control (left panel). The right panel shows that P2X7 knockdown does not compromise cancer cell growth and viability. One million wt, shRNA(NT) and shRNA(P2X7) 4T1.2 cells were plated and incubated for 48 h before evaluation of cell numbers and viability. FIG. 5B: P2X7 knockdown cells are more resistant to ATP and the ATP/IVM combo. 4T1.2 cells were treated for 24 h with 1-3 mM ATP, 6-10 µM Ivermectin, or combinations of ATP and Ivermectin. P2X7 knockdown suppresses the synergy between Ivermectin and high dose ATP, as shown by calculation of combination index (CI) values, see Table 2. FIG. 5C: P2X7 knockdown cells are resistant to ATP/Ivermectin induced membrane permeabilization (Asterisk (*) indicates p<0.05). FIG. 5D: The combination of Ivermectin (16 µM) and exogenous ATP (3 mM) can synergistically kill even some resistant human cancer cell lines like breast (MCF7), prostate (DU-145), head and neck (A253), and ovarian (SKOV3) cancer cells. FIG. 5E: Comparison of the protective effects of P2X7, CaMKII, and NADPH oxidases inhibition in short-term (4 h, 32 µM IVM) and long-term (24 h, 12 µM IVM) exposure of 4T1.2 cells to Ivermectin. Asterisk (*) indicates p<0.05 relative to Ivermectin alone controls.

FIG. 6A: Ivermectin induces autophagy in breast cancer cells. MDA-MB-231 GFL-LC3 cells were treated with different doses of Ivermectin for 24 h and formation of green fluorescent puncta was evaluated by confocal fluorescence microscopy. FIG. 6B: Western blot confirming the induction of autophagy in both murine and human breast cancer cells, as evidenced by LC3 lipidation and autophagic degradation of p62(SQSTM1). FIG. 6C: Ivermectin up-regulates surface exposure of M6P receptor (top panel) but does not impact the exposure of Calreticulin (CRT) (bottom panel). MDA-MB-231 cells (triplicates) were treated with different doses of Ivermectin for up to 24h and surface stained with antibody-specific for the human M6P receptor versus isotype control. Similarly, 4T1.2 and MB231 cells were treated with different doses of Ivermectin for 4-24 h, and were stained with an antibody specific for both human and mouse CRT versus isotype control. Mean fluorescent intensity (MFI) values and ratios versus isotype control were calculated after gating on live/membrane-intact cells. FIG. 6D: Ivermectin (32 µM) induces release of HMGB1 from murine and human TNBC cells (triplicates). FIG. 6E: Ivermectin treatment induces release of cytosolic LDH, data are normalized to maximum release (lysis). Asterisk (*) indicates p<0.05 relative to untreated or Ivermectin alone controls, respectively.

FIG. 8A: Combinations of different cell death inhibitors provide superior protection against Ivermectin. 4T1.2 cells were treated with 32 μM Ivermectin for 4 h and flow cytometry was used to evaluate the fraction of live, apoptotic, early and late necrotic cells. Cells were also pre-incubated for 1 h with different inhibitors of cell death pathways: apoptosis (z-vad-fmk, 4 and 40 μM), necroptosis (necrostatin-1, 10 and 100 μM), autosis (digoxin, 10 and 100 μM), and pyroptosis (VX-765, 10 and 100 μM). Synergy between the inhibitors was evaluated using the less effective lower drug dose. FIG. 8B: Flow cytometry analysis of caspase-1/3 activation in 4T1.2 cells treated with 32 μM Ivermectin for 1 h-4 h showing that caspase-1 cleavage precedes that of caspase-3.

FIG. 9A: Ivermectin causes hyper/de-polarization of the plasma membrane of mouse and human breast cancer cells, respectively. FIG. 9B: Ivermectin promotes slightly bigger cytosolic Cl⁻ influx in mouse compared to human breast cancer cells. FIG. 9C: Ivermectin causes very modest swelling of apoptotic and surviving 4T1.2 cells. FIG. 9D: Ivermectin-induced cell death is exacerbated by inhibition of I (Cl, swell) channels with DCPIB. FIG. 9E: Ivermectin induced $Ca^{2+}$ flux in 4T1.2 cells is dependent on both extracellular and intracellular (ER) $Ca^{2+}$ release. Extracellular and intracellular $Ca^{2+}$ was chelated with 1 mM EDTA and 20 μM BAPTA/AM, respectively. Chelation of extracellular rather than ER $Ca^{2+}$ protects against Ivermectin; plate bound viability assay and flow cytometry analysis of suspension cells are shown. FIG. 9F: Ivermectin induces generation of ROS in both murine and human TNBC cells. FIG. 9G: Blockade of H2O2- and Ivermectin-induced ROS by ROS scavengers NAC and GSH. FIG. 9H: Reactive oxygen species (ROS) scavengers fail to prevent or delay Ivermectin cytotoxicity.

FIGS. 10A-10L. Extracellular Dual roles of ATP and purinergic signaling in Ivermectin's killing. 4T1.2 cells were treated with Ivermectin for 4 h in the presence of different inhibitors at μM concentrations as indicated. FIG. 10A: The non-specific P2 purinergic receptor inhibitor Suramin (4-400 μM) exacerbates Ivermectin-induced cell death. FIG. 10B: Inhibition of extracellular ATPases with PSB 069 protects against Ivermectin cytotoxicity. FIG. 10C: Blockade of pannexin-1 channels with Panx-1 mimetic blocking peptide (Anaspec) and Probenecid at μM concentrations as indicated exacerbates killing. FIG. 10D: Human MDA-MB-231 cells have higher background membrane permeabilization to YOPRO-1 than the murine 4T1.2 cells and do not respond to further stimulation with 3 mM ATP and Ivermectin. FIG. 10E: ATP plays a transiently protective role only in the mouse but not human breast cancer cells. 4T1.2 and MDA-MB-231 cells were treated with 32 μM Ivermectin for 4 h in the presence of ATP at mM concentrations as indicated. FIG. 10F: qPCR showing up-regulation of P2X4 and P2X7 receptors on several murine cancer cell lines, including 4T1.2 and DD-Her2/neu (breast), and B16 (melanoma). FIG. 10G: Up-regulated expression of P2X4 and P2X7 receptors is a characteristic feature of human breast cancer. Expression of P2X and P2Y purinergic receptors, NOX family members, GABA, and Glycine receptors was analyzed using publicly available breast cancer cell lines datasets. Statistically significant (p<0.05) up-regulation and down-regulation in breast cancer versus normal cells is shown in red and blue, respectively. FIG. 10H: Correlation between sensitivity to Ivermectin and ATP across various human cancer cell lines. Cancer cells were treated for 24 h with 3 mM ATP or Ivermectin at 16 and 32 μM doses as indicated. FIG. 10I: KN-62 (10 μM) blocks both apoptotic and necrotic cell death (IVM 8 or 32 μM, 4 h). FIG. 10J: 10 μM KN-62 provides protection against Ivermectin in a broad spectrum of murine and human cancer cell types. Murine cells were treated with 32 μM Ivermectin for 4 h, while human cells were treated with 16 μM Ivermectin for 24 h. FIG. 10K: The P2X7 inhibitors PPADs, oxATP, and A438079 fail to provide protection against Ivermectin. 4T1.2 cells were treated with Ivermectin for 4 h after 30 min pre-incubation with P2X7 inhibitors at μM concentrations as indicated. FIG. 10L: Modulation of ATP+Ivermectin-induced membrane permeabilization by various P2X7-specific inhibitors. Membrane permeabilization in 4T1.2 cells was induced by the combination of 3 mM ATP and 32 μM Ivermectin. P2X7 inhibitors blocked membrane permeabilization at the μM doses indicated.

FIG. 11A: Inhibition of CaMKII blocks initial cytotoxicity in various highly Ivermectin-sensitive mouse cancer cell lines. Murine breast (DDHer-2), colon (CT26) and prostate (RM1) cancer cells were treated for 4 h with 32 μM Ivermectin in the presence of the P2X7/CaMKII dual inhibitor KN-62 or the CaMKII-specific inhibitor KN-93 at μM concentrations as indicated. FIG. 11B: Inhibition of MPTP with Cyclosporin A protects various highly Ivermectin-sensitive mouse cancer cell lines. Mouse breast (DDHer-2), colon (CT26) and prostate (RMI) cancer cells were treated for 4 h with 32 μM Ivermectin in the presence of the MPTP inhibitor Cyclosporin A at μM concentrations as indicated.

FIG. 12A: P2X7 knockdown inhibits both the early necrotic and the later apoptotic death pathways. FIG. 12B: Comparison of the protective effects of P2X7, CaMKII, and NADPH oxidase inhibition in short-term (4 h, 32 μM IVM) and long-term (24 h, 12 μM IVM) exposure of murine versus human TNBC cells. FIG. 12C: Only inhibition of the P2X7 receptor with KN-62 rather than inhibition of CaMKII (KN-93) and MPTP (Cyclosporin A) protects against ATP induced cytotoxicity. 4T1.2 and MDA-MB-231 cells were treated for 24 h with 2 and 3 mM ATP, respectively, in the presence of various inhibitors (μM concentrations indicated). FIG. 12D: High concentrations of exogenous extracellular ATP favor the necrotic over apoptotic death pathway induced by Ivermectin. FIG. 12E: The CaMKII-specific inhibitor KN-93 is the most potent at blocking ATP- and Ivermectin-induced membrane permeabilization to YOPRO-1. 4T1.2 cells were treated with 32 μM Ivermectin for 30 min in the presence of YOPRO-1 and 10 μM KN-62, 30 μM KN-93, and 400 μM Suramin. Asterisk (*) indicates p<0.05 relative to the respective control in each treatment group.

FIG. 13A: Murine 4T1.2 (breast), but not murine CT26 (colon adenocarcinoma) or human MB231 (breast) cancer cells manifest constitutive surface exposure of Calreticulin (CRT). FIG. 13B: Ivermectin does not induce the plasma membrane exposure of CRT (P>0.05) on live MB231 cells, neither does it up-regulate the exposure of CRT on the murine 4T1.2 cells. 4T1.2 and MB231 cells were treated with different doses of Ivermectin for 4 h and 24 h followed by surface staining with antibody-specific for both mouse and human CRT versus Isotype control and in the presence of viability/membrane integrity probe. Flow cytometry plots shown are gated on live or dead cells as indicated.

DETAILED DESCRIPTION

I. Definitions

Figure 1A:
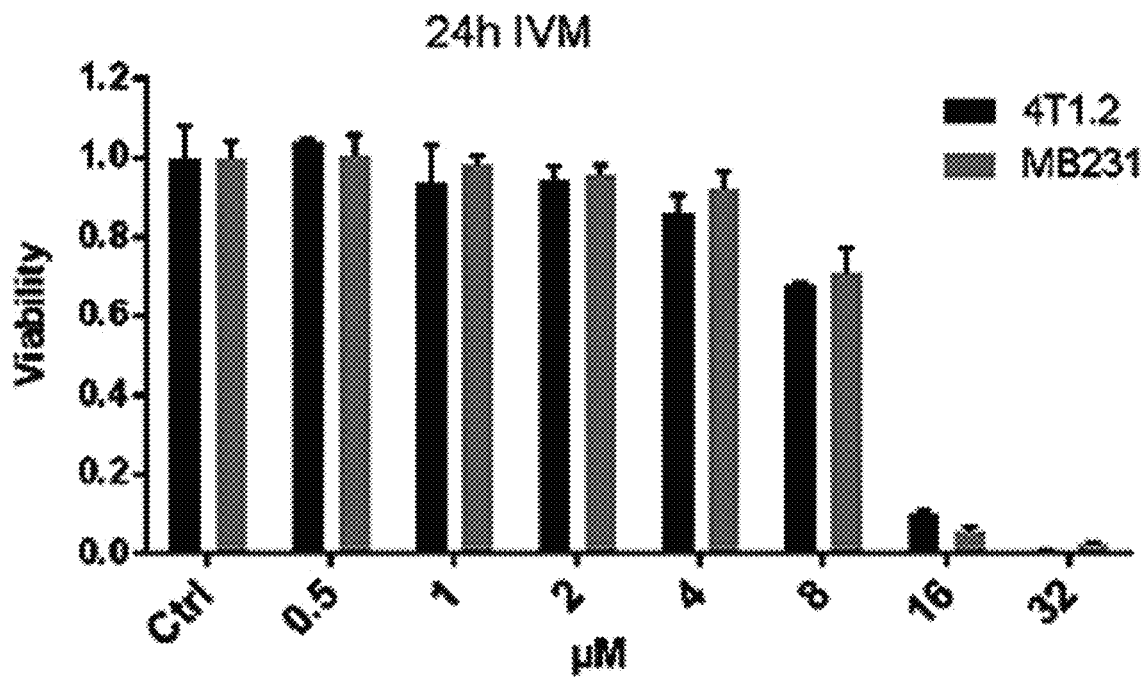
FIGS. 1A-1H. Ivermectin kills breast cancer cells through a mixed apoptotic and necrotic mechanism.

The abbreviations used herein have their conventional meaning within the chemical and biological arts. The chemical structures and formulae set forth herein are constructed according to the standard rules of chemical valency known in the chemical arts.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66: 1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, which is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, compounds of the present invention may exist in a prodrug form.

Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)-or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

The terms "a" or "an," as used in herein means one or more.

The term "local" as used herein, refers to the non-parenteral administration of a therapeutic agent. A local administration may include, but is not limited to topical or intratumoral. A minimal amount of systemic distribution is expected during a local administration but would be expected to maintain subclinical thresholds.

The terms "treating" or "treatment" refers to an indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat cancer (e.g. prostate cancer, castration-resistant prostate cancer, breast cancer, triple negative breast cancer, glioblastoma, medulloblastoma, cervical cancer, pancreatic cancer, ovarian cancer, lung cancer, squamous cell carcinoma (e.g head, neck, or esophagus cancer), colorectal cancer, or hematological malignancies (e.g. leukemia, acute myeloid leukemia, lymphoma, B cell lymphoma, or multiple myeloma)). For example certain methods herein treat cancer by decreasing or reducing or preventing the occurrence, growth, metastasis, or progression of cancer; or treat cancer by decreasing a symptom of cancer. Symptoms of cancer (e.g. prostate cancer, castration-resistant prostate cancer, breast cancer, triple negative breast cancer, glioblastoma, medulloblastoma, cervical cancer, pancreatic cancer, ovarian cancer, lung cancer, squamous cell carcinoma (e.g head, neck, or esophagus cancer), colorectal cancer, or hematological malignancies (e.g. leukemia, acute myeloid leukemia, lymphoma, B cell lymphoma, or multiple myeloma)), colorectal cancer, leukemia, acute myeloid leukemia, lymphoma, B cell lymphoma, or multiple myeloma) would be known or may be determined by a person of ordinary skill in the art. The term "treating" and conjugations thereof, include prevention of an injury, pathology, condition, or disease (e.g. preventing the development of one or more symptoms of cancer (e.g. prostate cancer, castration-resistant prostate cancer, breast cancer, triple negative breast cancer, glioblastoma, medulloblastoma, cervical cancer, pancreatic cancer, ovarian cancer, lung cancer, squamous cell carcinoma (e.g head, neck, or esophagus cancer), colorectal cancer, hematological malignancies (e.g. leukemia, acute myeloid leukemia, lymphoma, B cell lymphoma, or multiple myeloma)). In embodiments, the treatment does not include prevention.

An "effective amount" is an amount sufficient to accomplish a stated purpose (e.g. achieve the effect for which it is administered, treat a disease, reduce enzyme activity, increase enzyme activity, reduce transcriptional activity, increase transcriptional activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein (e.g. transcription factor) relative to the absence of the antagonist. An "activity increasing amount," as used herein, refers to an amount of agonist (activator) required to increase the activity of an enzyme or protein (e.g. transcription factor) relative to the absence of the agonist. A "function disrupting amount," as used herein, refers to the amount of antagonist (inhibitor) required to disrupt the function of an enzyme or protein (e.g. transcription factor) relative to the absence of the antagonist. A "function increasing amount," as used herein, refers to the amount of agonist (activator) required to increase the function of an enzyme or protein (e.g. transcription factor) relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The term "associated" or "associated with" in the context of a substance or substance activity or function associated with a disease (e.g., cancer) means that the disease (e.g. cancer) is caused by (in whole or in part), or a symptom of the disease is caused by (in whole or in part) the substance or substance activity or function. For example, a symptom of a disease or condition associated with the ATP/P2X4/P2X7/Pannexin-1/Caspase-1 signaling pathway. As used herein, what is described as being associated with a disease, if a causative agent, could be a target for treatment of the disease. For example, a disease associated with the ATP/P2X4/P2X7/Pannexin-1/Caspase-1 signaling pathway, may be treated with a macrocyclic lactone, alone or in combination with a modulator (e.g. compounds, agents, and therapies as described herein) effective for modulating the ATP/P2X4/P2X7/Pannexin-1/Caspase-1 signaling pathway. As used herein, what is described as being associated with a disease, if a causative agent, could be a target for treatment of the disease.

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. ATP, P2X4, P2X7). In some embodiments contacting includes allowing a compound described herein to interact with a protein or enzyme that is involved in a signaling pathway (e.g. ATP/P2X4/P2X7/Pannexin-1/Caspase-1 signaling pathway).

As defined herein, the term "inhibition", "inhibit", "inhibiting" and the like (e.g. in reference to a protein-inhibitor (e.g. antagonist) interaction) means negatively affecting (e.g. decreasing) the activity or function of a target compound (e.g. a protein such as mTOR, ER, EGFR tyrosine kinase, CD39, CD73, PD-1, PD-L1, PD-L2, CTLA-4, TIGIT, BTLA, LAG-3, TIM-3, 2B4, CD 160, or LIGHT/HVEM) with an inhibitor relative to the activity or function of the target compound (e.g. protein) in the absence of the inhibitor. In some embodiments inhibition refers to reduction of a disease or symptoms of disease. Thus, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like (e.g. in reference to a protein-inhibitor (e.g. antagonist) interaction) means positively affecting (e.g. increasing) the activity or function of a target compound (e.g. a protein such as P2X4, P2X7, Pannexin-1, Toll-like receptors, RIG-I-like receptors, GITR, OX40, 41BB, ICOS, or CD27) relative to the activity or function of the protein in the absence of the activator. In some embodiments, activation refers to an increase in the activity of a signal transduction pathway or signaling pathway (e.g. ATP/P2X4/P2X7/Pannexin-1/Caspase-1 signaling pathway). Thus, activation may include, at least in part, partially or totally increasing stimulation, increasing or enabling activation, or activating, sensitizing, or up-regulating signal transduction or enzymatic activity of a target compound (e.g. a protein such as P2X4, P2X7, Pannexin-1, Toll-like receptor, RIG-I-like receptor, GITR, OX40, 41BB, ICOS, or CD27).

The term "modulator" refers to a composition that increases or decreases the activity of a target molecule or the function of a target molecule (e.g., P2X4, P2X7, Pannexin-1, Toll-like receptor, RIG-I-like receptor, GITR, OX40, 41BB, ICOS, CD27, mTOR, ER, EGFR tyrosine kinase, CD39, CD73, PD-1, PD-L1, PD-L2, CTLA-4, TIGIT, BTLA, LAG-3, TIM-3, 2B4, CD160, or LIGHT/HVEM) with a modulator relative to the activity or function of the target compound (e.g. protein) in the absence of the modulator. In some embodiments, modulation refers to an increase or decrease in the activity of a signal transduction pathway or signaling pathway (e.g. ATP/P2X4/P2X7/Pannexin-1/Caspase-1 signaling pathway). In some embodiments, a modulator is a compound (e.g. macrocyclic lactone and ATP, macrocyclic lactone and ATP analogs, macrocyclic lactone and BzATP) that reduces the severity of one or more symptoms of a disease associated with a protein (e.g., P2X4, P2X7, Pannexin-1, Toll-like receptors, RIG-I-like receptors, GITR, OX40, 41BB, ICOS, CD27, mTOR, ER, EGFR tyrosine kinase, CD39, CD73, PD-1, PD-L1, PD-L2, CTLA-4, TIGIT, BTLA, LAG-3, TIM-3, 2B4, CD160, or LIGHT/HVEM) or pathway (e.g. ATP/P2X4/P2X7/Pannexin-1/Caspase-1 signaling pathway), for example cancer.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a mammal. In some embodiments, a patient is a mouse. In some embodiments, a patient is an experimental animal. In some embodiments, a patient is a rat. In some embodiments, a patient is a test animal.

"Disease" or "condition" refer to a state of being or health status of a patient or subject capable of being treated with a compound, pharmaceutical composition, or method provided herein. In some embodiments, the disease is cancer.

Examples of diseases, disorders, or conditions include, but are not limited to, cancer (e.g.

prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma). In some instances, "disease" or "condition" refers to cancer. In some further instances, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma. In some further instances, "cancer" refers to lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, metastatic cancer, or carcinoma.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairycell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

"Therapy resistant" or "therapy-resistant" cancers, tumor cells, and tumors refer to cancers that have become resistant (e.g. are not as susceptible to being treated by the resistant therapy compared to a non-resistant cancer, tumor cell, or tumor) to one or more cancer therapies (e.g. apoptosis-mediated, non-apoptosis-mediated, reactive oxygen species inducing therapy, ATP releasing therapy, autophagy inducing therapy, irradiation therapy, cryoablation therapy, thermal ablation therapy) including, but not limited to, chemotherapy, hormonal therapy, radiotherapy, immunotherapy, and combinations thereof.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). In embodiments, administration includes direct administration to a tumor. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent or chemotherapeutic). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, J. *Biomater. Sci. Polym. Ed.* 7: 623-645, 1995; as biodegradable and injectable gel formulations (see, e.g., *Gao Pharm. Res.* 12: 857-863, 1995); or, as microspheres for oral administration (see, e.g., Eyles, *J. Pharm. Pharmacol.* 49: 669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13: 293-306, 1996; Chonn, *Curr. Opin. Biotechnol.* 6: 698-708, 1995; Ostro, *Am. J. Hosp. Pharm.* 46: 1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in an effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g., a protein such as mTOR, ER, EGFR tyrosine kinase, CD39, CD73, PD-1, PD-L1, PD-L2, CTLA-4, TIGIT, BTLA, LAG-3, TIM-3, 2B4, CD160, or LIGHT/HVEM) or pathway (e.g. ATP/P2X4/P2X7/Pannexin-1/Caspase-1 signaling pathway) and/or reducing, eliminating, or slowing the progression of disease symptoms (e.g. symptoms of cancer). Determination of a therapeutically effective amount of a compound or combination of compounds of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent(s).

In some embodiments, co-administration includes administering one or more active agents within 0.5, 1, 2, 4, 6, 8, 10, 12, 16, 20, or 24 hours of another active agent. Co-administration includes administering two or more active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with each other and/or with other treatments for cancer such as surgery.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (GLEEVEC®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D;

antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine;

calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cyclopatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab;

eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol.™ (i.e. paclitaxel, taxol), Taxotere.™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin Al (i.e. BTO-956 and DIME), Fijianolide B, Laulimalide, Narcosine (also known as NSC-5366), Nascapine, Hemiasterlin, Vanadocene acetylacetonate, Monsatrol, lnanocine (i.e. NSC-698666), Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (–)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., full-time), immunostimulants (e.g., Bacillus Calmette-Guérin (BCG), levami sole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (IRESSA™), erlotinib (TARCEVA™), cetuximab (ERBITUX™), lapatinib (TYKERB™), panitumumab (VECTIBIX™), vandetanib (CAPRELSA™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

according to the present invention "antibody" or "immunoglobulin" have the same meaning, and will be used equally in the present invention. the term "antibody" as used herein refers to immunoglobulin molecules and immunologically active portions of immunoglobulin molecules, i.e., molecules that contain an antigen binding site that specifically binds an antigen. As such, the term antibody encompasses not only whole antibody molecules, but also antibody fragments as well as variants (including derivatives) of antibodies and antibody fragments. in natural antibodies, two heavy chains are linked to each other by disulfide bonds and each heavy chain is linked to a light chain by a disulfide bond, There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. the light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine the binding site specific to the antigenic epitope. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. the specificity of the antibody resides in the structural complementarity between the antibody binding site and the antigenic epitope. Antibody binding sites are made up of residues that are primarily from the hypervariable or complementarity determining regions (CDRs). Occasionally, residues from hypervariable or framework regions (FR) influence the overall domain structure and hence the binding site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The term "chimeric antibody" refers to an antibody which comprises a VH domain and a VL domain of an antibody (e.g. CD39, CD73) from any species, preferably mouse, and a CH domain and a CL domain of a human antibody.

According to the invention, the term "humanized antibody" refers to an antibody having variable region framework and constant regions from a human antibody but retains the CDRs of an antibody (e.g. CD39, CD73) from any species, preferably mouse.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

"Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

The term "depleting agent" refers to a protein-inhibitor (e.g. antagonist, agent) capable of reducing or negatively affecting (e.g. inhibiting, decreasing) the quantity of the target (e.g., regulatory T cells, myeloid derived suppressor cells) relative to the quantity of target in the absence of the depleting agent. In embodiments, a regulatory T cell depleting agent reduces the overall amount of regulatory T cells relative to the absence of the T cell depleting agent. In embodiments, a myeloid derived suppressor cell depleting agent reduces the overall amount of myeloid derived suppressor cells relative to the absence of the myeloid derived suppressor cell depleting agent. In embodiments, the quantity of the target in the treated subject is at least about 10% lower than, at least about 25% lower than, at least about 50% lower than, at least about 75% lower than, and/or at least about 90% lower than the quantity of the target in the untreated subject.

The term "mTOR" refers to the protein "mechanistic target of rapamycin (serine/threonine kinase)" or "mammalian target of rapamycin". The term "mTOR" may refer to the nucleotide sequence or protein sequence of human mTOR (e.g., Entrez 2475, Uniprot P42345, RefSeq NM_004958, or RefSeq NP_004949). The term "mTOR" includes both the wild-type form of the nucleotide sequences or proteins as well as any mutants thereof. In some embodiments, "mTOR" is wild-type mTOR. In some embodiments, "mTOR" is one or more mutant forms. In embodiments, an mTOR is the human mTOR. In embodiments, the mTOR has the nucleotide sequence corresponding to reference number GI:206725550. In embodiments, the mTOR has the nucleotide sequence corresponding to RefSeq NM_004958.3. In embodiments, the mTOR has the protein sequence corresponding to reference number GI:4826730. In embodiments, the mTOR has the protein sequence corresponding to RefSeq NP_004949.1 In embodiments, the mTOR is a mutant mTOR. In embodiments, the mutant mTOR is associated with a disease that is not associated with wildtype mTOR.

The term "estrogen receptor" or "ER" refers to a nuclear receptor activated by binding of the hormone estrogen (17β-estradiol). The term "estrogen receptor" may refer to the nucleotide sequence or protein sequence of human estrogen receptor. The term "estrogen receptor" may refer to the nucleotide sequence or protein sequence of human estrogen receptor 1 (a.k.a. ER-alpha, ERalpha, or ERα) (e.g., Entrez 2099, Uniprot P03372, RefSeq NM_000125, GI: 170295798, or OMIM 133430). The term "estrogen receptor" may refer to the nucleotide sequence or protein sequence of human estrogen receptor 2 (a.k.a. ER-beta, ERbeta, or ERβ) (e.g., Entrez 2100, Uniprot Q92731, RefSeq NM_001040275, GI: 94538324, or OMIM 601663). The term "estrogen receptor" includes both the wild-type form of the nucleotide sequences or proteins as well as any mutants thereof. In some embodiments, "estrogen receptor" is wild-type estrogen receptor. In some embodiments, "estrogen receptor" is one or more mutant forms. In embodiments, an estrogen receptor is the wildtype human estrogen receptor. In embodiments, an estrogen receptor is the wild-type human ERα. In embodiments, an estrogen receptor is the wildtype human ERβ. In embodiments, an estrogen receptor is the wildtype human ERα or ERβ. In embodiments, an estrogen receptor is the wildtype human ERα and ERβ. In embodiments, the estrogen receptor is a mutant estrogen receptor. In embodiments, the mutant estrogen receptor is associated with a disease that is not associated with wildtype estrogen receptor (e.g., drug resistant cancer, therapy resistant cancer).

The term "EGFR" refers to epidermal growth factor. The term "EGFR" may refer to the nucleotide sequence or protein sequence of human EGFR (e.g., Entrez 1956, Uniprot P0053, RefSeq NM_005228, GI: 41327737, RefSEQ NP_005219, and/or GI: 29725609). The term "EGFR" includes both the wild-type form of the nucleotide sequences or proteins as well as any mutants thereof. In some embodiments, "EGFR" is wild-type EGFR. In some embodiments, "EGFR" is one or more mutant forms. In embodiments, a EGFR is the human EGFR. In embodiments, the EGFR has the nucleotide sequence corresponding to reference number GI: 41327737. In embodiments, the EGFR has the nucleotide sequence corresponding to RefSeq NM_005228.3. In embodiments, the EGFR has the protein sequence corresponding to RefSeq NP_005219.2. In embodiments, the EGFR has the protein sequence corresponding to GI: 29725609.

The term "P2X purinoceptor 4" or "P2X4" or "P2RX4" refers to a ligand-gated cation channel that opens in response to the binding of ATP or ATP-analogs. The term "P2X4" may refer to the nucleotide sequence or protein sequence of human P2RX4 (e.g., Entrez 5205, Uniprot Q99571, RefSeq NM_001256796, GI: 378404896, RefSEQ NP_001243725, and/or GI: 378404897). The term "P2X4" includes both the wild-type form of the nucleotide sequences or proteins as well as any mutants thereof. In some embodiments, "P2X4" is wild-type P2X4. In some embodiments, "P2X4" is one or more mutant forms. In embodiments, the P2X4 has the nucleotide sequence corresponding to reference number GI: 378404896. In embodiments, the P2X4 has the nucleotide sequence corresponding to RefSeq NM_001256796.1. In embodiments, the P2X4 has the protein sequence corresponding to RefSeq NP_001243725.1. In embodiments, the P2X4 has the protein sequence corresponding to GI: 378404897.

The term "P2X purinoceptor 7" or "P2X7" or "P2RX7" refers to a ligand-gated cation channel that opens in response to the binding of ATP or ATP-analogs. The term "P2X7" may refer to the nucleotide sequence or protein sequence of human P2RX7 (e.g., Entrez 5207, Uniprot Q99572, RefSeq NM_002562, GI: 300068986, RefSEQ NP_002553, and/or GI: 300068987). The term "P2X7" includes both the wild-type form of the nucleotide sequences or proteins as well as any mutants thereof. In some embodiments, "P2X7" is wild-type P2X7. In some embodiments, "P2X7" is one or more mutant forms. In embodiments, a P2X7 is the human P2X7. In embodiments, the P2X7 has the nucleotide sequence corresponding to reference number GI: 300068986. In embodiments, the P2X7 has the nucleotide sequence corresponding to RefSeq NM_002562.5. In embodiments, the P2X7 has the protein sequence corresponding to RefSeq NP_002553.3. In embodiments, the P2X7 has the protein sequence corresponding to GI: 300068987.

The term "Pannexin-1" or "Pannexinl" or "Pannexin 1" refers to a large transmembrane channel. The term "Pannexin-1" may refer to the nucleotide sequence of human pannexin 1 PANX1 (e.g., Entrez 24145, Uniprot Q96RD7, RefSeq NM_015368, and/or GI: 39995063. The term "Pannexin-1" includes both the wild-type form of the nucleotide sequences or proteins as well as any mutants thereof. In some embodiments, "Pannexin-1" is wild-type Pannexin-1. In some embodiments, "Pannexin-1" is one or more mutant forms. In embodiments, a Pannexin-1 is the human Pannexin-1. In embodiments, the Pannexin-1has the nucleotide sequence corresponding to reference number GI: 39995063. In embodiments, the P2X7 has the nucleotide sequence corresponding to RefSeq NM_015368.3.

The term "Liver X receptor" or "LXR" refers to a member of the nuclear receptor family of transcription factors having two isoforms, LXRα and LXRβ. The term "Liver X receptor" may refer to LXRα or LXRβ. The term "Liver X receptor" may refer to the nucleotide sequence of human NR1H3 (e.g., Entrez 10062, Uniprot Q13133, RefSeq NM_005693, and/or GI: 353731054). The term "Liver X receptor" includes both the wild-type form of the nucleotide sequences or proteins as well as any mutants thereof. In some embodiments, "Liver X receptor" is wild-type Liver X receptor. In some embodiments, "Liver X receptor" is one or more mutant forms. In embodiments, a Liver X receptor is the human Liver X receptor. In embodiments, the Liver X receptor has the nucleotide sequence corresponding to reference number GI: 353731054. In embodiments, the Liver X receptor has the nucleotide sequence corresponding to RefSeq NM_005693.3. The term "Liver X receptor" may refer to the nucleotide sequence or protein sequence of human NR1H3 (e.g., Entrez 7376, Uniprot P55055, RefSeq NM_007121, and/or GI: 375331886). The term "Liver X receptor" includes both the wild-type form of the nucleotide sequences or proteins as well as any mutants thereof. In some embodiments, "Liver X receptor" is wild-type Liver X receptor. In some embodiments, "Liver X receptor" is one or more mutant forms. In embodiments, the Liver X receptor has the nucleotide sequence corresponding to reference number GI: 375331886. In embodiments, the Liver X receptor has the nucleotide sequence corresponding to RefSeq NM_007121.5.

The term "ATP/P2X4/P2X7/Pannexin-1/Caspase-1 signaling pathway" refers to the signaling pathway initiated by P2X4 activation, followed by activation of P2X7, followed by the opening of Pannexin-1 channels, followed by activation of caspase-1. In embodiments, activation of the ATP/P2X4/P2X7/Pannexin-1/Caspase-1 signaling pathway results in opening P2X4/P2X7/Pannexin-1 channels resulting in at least partial (e.g. partial) permeabilization of the plasma membrane. In embodiments, activation of the ATP/P2X4/P2X7/Pannexin-1/Caspase-1 signaling pathway results in cell death. In embodiments, prolonged stimulation of the ATP/P2X4/P2X7/Pannexin-1/Caspase-1 signaling pathway results in cell death.

The term "macrocyclic lactone" refers to a compound having a lactone ring moiety with 10 or more members. In embodiments, the macrocyclic lactone is a 16-membered macrocyclic lactone.

In embodiments, the macrocyclic lactone is a microorganism (e.g. engineered microorganism or particular soil microorganism, such as those belonging to the genus *Streptomyces*) fermentation product, or synthetic or semi-synthetic chemical derivative thereof. In embodiments, the macrocyclic lactone modulates (e.g. potentiate, enhances sensitivity of) a P2X4 receptor. In embodiments, macrocyclic lactones comprise fermentation products, or chemical derivatives thereof, produced by *Streptomyces avermitilis*, also called avermectins. Useful macrocyclic lactones are set forth, for example, in PCT/IB2012/052165, which is incorporated herein by reference for all purposes. In embodiments, macrocyclic lactones comprise fermentation products, or chemical derivatives thereof, produced by Streptomyces hygroscopicus, also called milbemycins. In embodiments, a macrocyclic lactone is an avermectin (e.g. ivermectin, abamectin, doramectin, eprinomectin, or selamectin). In embodiments, the macrocyclic lactone is ivermectin (commercialized under the name of MECTIZAN™/ STROMECTOI™ (Merck & Co. Inc.)) In embodiments, the macrocyclic lactone is abamectin. In embodiments, the macrocyclic lactone is doramectin. In embodiments, the macrocyclic lactone is eprinomectin. In embodiments, the macrocyclic lactone is selamectin. In embodiments, the macrocyclic lactone is described in Chem. Pharm. Bull. (Tokyo). 2012, 60 (8): 931-944, which is incorporated herein by reference for all purposes. In embodiments, the macrocyclic lactone is a milbemycin (e.g. milbemectin, milbemycin oxime, moxidectin, or nemadectin). As avermectins, the family of milbemycins includes closely related compounds and semisynthetic mixtures thereof (e.g. those disclosed in U.S. Pat. No. 4,144,352, which is incorporated herein by reference for all purposes).

The term "avermectin" refers to 16-membered macrocyclic lactone derivates typically used to treat parasitic worms. In embodiments, the avermectin is or includes compounds that are described in Albers-Schonberg et al., 1981, J. Am. Chem. Soc, 103, 4216-4221, which is incorporated herein by reference for all purposes; Danishefsky et al, 1989, J. Am. Chem. Soc, 111, 2967-2980, which is incorporated herein by reference for all purposes; US 2009/0281175, which is incorporated herein by reference for all purposes, as well as derivatives or mixtures thereof. Useful macrocyclic lactones are set forth, for example, in PCT/IB2012/052165 which is incorporated herein by reference for all purposes. In embodiments, an avermectin is ivermectin, abamectin, doramectin, eprinomectin or selamectin.

The term "abamectin" is or includes a mixture of avermectin Bla and avermectin B1b. In particular, abamectin covers a mixture of macrocyclic lactones comprising about or at least 80% of avermectin Bla and about or less than 20% of avermectin B1b. In embodiments, the abamectin is the commercial compound commercialized under the names of AFFIRM™, AVID™ (Syngenta) and ZEPHYL™.

The term "ivermectin" is used according to its plain and ordinary meaning in the art and includes a mixture of 22,23-dihydroxy-avermectin Bla and 22,23-dihydroxy-avermectin B1b. In embodiments, ivermectin is a mixture of macrocyclic lactones including at least 90% of 22,23-dihydroxy-avermectin B1a and about 10% or less of 22,23-dihydroxy-avermectin B1b. 22,23-dihydroxy-avermectin B1a may also be referred to as (10E, 14E, 16E)-(1R, 4S, 5'S, 6R, 6'R, 8R, 12S, 13S, 20R, 21R, 24S)-6'-[(S)-sec-butyl]-21,24-dihydroxy-5',11,13,22-tetramethyl-2-oxo-(3 ,7, 19-tri oxatetracyclo[15.6.1.1$^{4,8}$.O$^{20, 24}$]pentacosa-10,14,16,22-tetraene)-6-spiro-2'-(tetrahydropyran)-12-yl 2,6-dideoxy-4-O—(2,6-dideoxy-3-O-methyl-α-L-arabino-hexopyranosyl)-3-O-methyl-α-L-arabino-hexopyranoside. 22,23-dihydroxy-avermectin B1b may also be referred to asa (10E, 14E, 16E)-(1R, 4S, 5'S, 6R, 6'R, 8R, 12S, 13S, 20R, 21R, 24S)-21,24-dihydroxy-6'-isopropyl-5',11,13, 22-tetramethyl-2-oxo-(3,7, 19-oxatetracyclo[15.6.1.1$^{4,8}$.O$^{20, 24}$]pentacosa-10,14,16,22-tetraene)-6-spiro-2'-(tetrahydro pyran)-12-yl 2,6-dideoxy-4-O—(2,6-dideoxy-3-O-methyl-α-L-arabino-hexopyranosyl)-3-O-methyl-α-L-arabino-hexo pyranoside. In embodiments, ivermectin is a commercial compound referred to as STROMECTOL™ (Merck & Co., Inc.) or MECTIZAN™. In embodiments, the macrocyclic lactone is 22,23-dihydroxy-avermectin B1a or 22,23-dihydroxy-avermectin B1b.

"Reactive oxygen species inducing therapy" refers to treatments or agents that increase reactive oxygen species to therapeutic levels (e.g. by modulating hormone activity). In embodiments, the therapeutic levels are amounts sufficient to provide an anti-cancer effect either alone or with additional anti-cancer agents (e.g. a macrocyclic lactone such as ivermectin). Modulation of hormone activity may include increasing, decreasing, blocking, removing, or otherwise changing the level of a hormone or the level of activity of a hormone. Non-limiting examples of oxidizing species include superoxide radical, hydroxyl radical, organic hydroperoxide, alkoxy radicals, peroxy radicals, hypochlorous acid, and hydrogen peroxide (Br. J. Exp. Path. (1989) 70, 737-757). In embodiments, a reactive oxygen species inducing therapy is also an ATP releasing therapy. In embodiments, a reactive oxygen species inducing therapy is an autophagy inducing therapy. In embodiments, a reactive oxygen species inducing therapy increases activation of NADPH oxidase. In embodiments, a reactive oxygen species inducing therapy comprises $H_2O_2$. In embodiments, a reactive oxygen species inducing therapy is irradiation therapy, cryoablation therapy, or thermal ablation therapy.

"ATP releasing therapy" refers to treatments or agents that increase ATP to therapeutic levels (e.g. by modulating hormone activity). In embodiments, the therapeutic levels are amounts sufficient to provide an anti-cancer effect either alone or with additional anti-cancer agents (e.g. a macrocyclic lactone such as ivermectin). Modulation of hormone activity may include increasing, decreasing, blocking, removing, or otherwise changing the level of a hormone or the level of activity of a hormone. In embodiments, the ATP releasing therapy is administration of a pro-apoptotic drug such as doxorubicin or staurosporine. In embodiments, the ATP releasing therapy is an autophagy inducing therapy. In embodiments, the ATP releasing therapy is a reactive oxygen species inducing therapy. In embodiments, the ATP releasing therapy is also irradiation therapy, cryoablation therapy, or thermal ablation therapy.

"Autophagy inducing therapy" refers to treatments or agents that increase the rate of lysosomal degradation of proteins and organelles to therapeutic levels (e.g. by modulating hormone activity). In embodiments, the therapeutic levels are amounts sufficient to provide an anti-cancer effect either alone or with additional anti-cancer agents (e.g. a macrocyclic lactone such as ivermectin). Modulation of hormone activity may include increasing, decreasing, blocking, removing, or otherwise changing the level of a hormone or the level of activity of a hormone. In embodiments, the autophagy inducing therapy is an ATP releasing therapy. In embodiments, the autophagy inducing therapy is a reactive oxygen species inducing therapy. In embodiments, the autophagy inducing therapy is irradiation therapy, cryoablation therapy, or thermal ablation therapy. In embodiments, an autophagy inducing therapy comprises tetrandrine.

"Irradiation therapy" is used in accordance with its plain ordinary meaning and refers to a method of treatment using radiation to inhibit the growth or proliferation of cells to therapeutic levels. In embodiments, the therapeutic levels are amounts sufficient to provide an anti-cancer effect either alone or with additional anti-cancer agents (e.g. a macrocyclic lactone such as ivermectin). In embodiments, the radiation is x-rays, gamma rays, or charged particles.

"Cryoablation therapy" is used in accordance with its plain ordinary meaning and refers to a method of treatment using extreme cold fluids to destroy, damage, or inhibit the growth or proliferation of cells to therapeutic levels. In embodiments, the therapeutic levels are amounts sufficient to provide an anti-cancer effect either alone or with additional anti-cancer agents (e.g. a macrocyclic lactone such as ivermectin). In embodiments, the fluid is in the range of −75° C. to −10° C. In embodiments, the fluid is a pressurized refrigerant. In embodiments, the fluid is liquid nitrous oxide.

"Thermal ablation therapy" is used in accordance with its plain ordinary meaning and refers to a method of treatment using a heat or energy source to destroy, damage, or inhibit the growth or proliferation of cells to therapeutic levels. In embodiments, the therapeutic levels are amounts sufficient to provide an anti-cancer effect either alone or with additional anti-cancer agents (e.g. a macrocyclic lactone such as ivermectin). In embodiments, the heat or energy source is high-intensity focused ultrasound, radiofrequency, microwave, or laser beam. In embodiments, thermal ablation therapy is high-intensity focused ultrasound therapy. In embodiments, thermal ablation therapy is radiofrequency therapy. In embodiments, thermal ablation therapy is microwave therapy. In embodiments, thermal ablation therapy is laser ablation therapy.

A modulator of the ATP/P2X4/P2X7/Pannexin-1/Caspase-1 signaling pathway refers to a compound that increases or decreases an activity within, or effect of, the ATP/P2X4/P2X7/Pannexin-1/Caspase-1 signaling pathway relative to the absence of the modulator of the ATP/P2X4/P2X7/Pannexin-1/Caspase-1 signaling pathway. In embodiments, the modulator of the ATP/P2X4/P2X7/Pannexin-1/Caspase-1 signaling pathway is an agonist of the ATP/P2X4/P2X7/Pannexin-1/Caspase-1 signaling pathway that increases an activity within or effect of the ATP/P2X4/P2X7/Pannexin-1/Caspase-1 signaling pathway relative to the absence of the modulator of the ATP/P2X4/P2X7/Pannexin-1/Caspase-1 signaling pathway. In embodiments, the agonist of the ATP/P2X4/P2X7/Pannexin-1/Caspase-1 signaling pathway is a P2X4 agonist or P2X7 agonist. The increase may include partially or totally increasing stimulation, increasing or enabling activation, or activating, sensitizing, or up-regulating signal transduction or enzymatic activity or the amount of a protein (e.g. a protein decreased in a disease such as cancer). In embodiments, the modulator of the ATP/P2X4/P2X7/Pannexin-1/Caspase-1 signaling pathway is an antagonist of the ATP/P2X4/P2X7/Pannexin-1/Caspase-1 signaling pathway that decreases an activity within or effect of the ATP/P2X4/P2X7/Pannexin-1/Caspase-1 signaling pathway relative to the absence of the modulator of the ATP/P2X4/P2X7/Pannexin-1/Caspase-1 signaling pathway. In embodiments, the agonist of the ATP/P2X4/P2X7/Pannexin-1/Caspase-1 signaling pathway is ATP. In embodiments, the agonist of the ATP/P2X4/P2X7/Pannexin-1/Caspase-1 signaling pathway is an ATP analog. In embodiments, the agonist of the ATP/P2X4/P2X7/Pannexin-1/Caspase-1 signaling pathway is an ATP derivative. In embodiments, the agonist of the ATP/P2X4/P2X7/Pannexin-1/Caspase-1 signaling pathway is BzATP. In embodiments, the agonist of the ATP/P2X4/P2X7/Pannexin-1/Caspase-1 signaling pathway is ADP. In embodiments, the agonist of the ATP/P2X4/P2X7/Pannexin-1/Caspase-1 signaling pathway is AMP. In embodiments, the agonist of the ATP/P2X4/P2X7/Pannexin-1/Caspase-1 signaling pathway is αβ-methylene ATP.

As defined herein, a "P2X4 agonist" refers to an agent that increases an activity within or effect of the ATP/P2X4/P2X7/Pannexin-1/Caspase-1 signaling pathway (e.g. activation of the signaling pathway) by directly effecting the level or activity of P2X4. In embodiments, the P2X4 agonist is ATP. In embodiments, the P2X4 agonist is an ATP analog. In embodiments, P2X4 agonist is an ATP derivative. In embodiments P2X4 agonist is BzATP. In embodiments, P2X4 agonist is ADP. In embodiments, P2X4 agonist is AMP. In embodiments, P2X4 agonist is αβ-methylene ATP.

As defined herein, a "P2X7 agonist" refers to an agent that increases an activity within or effect of the ATP/P2X4/P2X7/Pannexin-1/Caspase-1 signaling pathway (e.g. activation of the signaling pathway) by directly effecting the level or activity of P2X7. In embodiments, the P2X7 agonist is ATP. In embodiments, the P2X7 agonist is an ATP analog. In embodiments, P2X7 agonist is an ATP derivative. In embodiments P2X7 agonist is BzATP. In embodiments, P2X7 agonist is ADP. In embodiments, P2X7 agonist is AMP. In embodiments, P2X7 agonist is αβ-methylene ATP.

ATP is used in accordance with its plain ordinary meaning and refers to adenosine triphosphate. An ATP analog is a compound that is similar or comparable in function and appearance but not in exact structure or origin to a reference compound. In embodiments, an ATP analog is an ATP precursor (e.g. adenosine diphosphate, adenosine monophosphate), or chemical derivative (e.g. 2'(3')—O—(4-benzoylbenzoyl)adenosine-5'-triphosphate (BzATP), 7-deazaadenosine analog, 5'-N-ethylcarboxamidoadenosine, 3"-ethynyladenosine, formycin, BCX4430, N6-2-(4-aminophenyl) ethyladenosine, toyocamycin, N6-(3-methoxyl-4-hydroxybenzyl) adenine riboside (B2), 2-chloroadenosine).

An "mTOR inhibitor" refers to a compound (e.g. antibody, drug) that decreases the activity or levels of mTOR. In embodiments, an mTOR inhibitor binds mTOR. In embodiments, the mTOR inhibitor inhibits the enzymatic activity of mTOR. In embodiments, the mTOR inhibitor inhibits a function of mTOR. In embodiments, the mTOR inhibitor inhibits a protein-protein interaction of mTOR. In embodiments, the mTOR inhibitor inhibits the normal localization of mTOR. In embodiments, the mTOR inhibitor inhibits ligand binding to mTOR. In embodiments, the mTOR inhibitor induces an inactive conformation of mTOR. In embodiments, the mTOR inhibitor increases degradation of mTOR. In embodiments, the mTOR inhibitor inhibits post-translational modification of mTOR. In embodiments, the mTOR inhibitor is rapamycin or a rapamycin derivative (e.g. sirolimus, temsirolimus, everolimus, deforolimus).

An "ER inhibitor" refers to a compound (e.g. antibody, drug) that decreases the activity or levels of estrogen receptor (ER). In embodiments, an ER inhibitor binds ER. In embodiments, the ER inhibitor inhibits the enzymatic activity of ER. In embodiments, the ER inhibitor inhibits a function of ER. In embodiments, the ER inhibitor inhibits a protein-protein interaction of ER. In embodiments, the ER inhibitor inhibits the normal localization of ER. In embodiments, the ER inhibitor inhibits ligand binding to ER. In embodiments, the ER inhibitor induces an inactive conformation of ER. In embodiments, the ER inhibitor increases degradation of ER. In embodiments, the ER inhibitor inhibits posttranslational modification of ER. In embodiments, the ER inhibitor is tamoxifen. In embodiments, the ER inhibitor is an antiestrogen, an aromatase inhibitor, SERM, fluvestrant, clomifene, femarelle, ormeloxifene, raloxifene, tamoxifen, toremifene, lasofoxifene, ospemifene, anastrozole, letrozole, exemestane, vorozole, formestane, fadrozole, aminoglutethimide, and testolactone. In embodiments, the ER inhibitor is fluvestrant, clomifene, femarelle, ormeloxifene, raloxifene, tamoxifen, toremifene, lasofoxifene, and ospemifene.

An "EGFR tyrosine kinase inhibitor" or "EGFR inhibitor" refers to a compound (e.g. antibody, drug) that decreases the activity or levels of EGFR. In embodiments, an EGFR inhibitor binds EGFR. In embodiments, the EGFR inhibitor inhibits the enzymatic activity of EGFR. In embodiments, the EGFR inhibitor inhibits a function of EGFR. In embodiments, the EGFR inhibitor inhibits a protein-protein interaction of EGFR. In embodiments, the EGFR inhibitor inhibits the normal localization of EGFR. In embodiments, the EGFR inhibitor inhibits ligand binding to EGFR. In embodiments, the EGFR inhibitor induces an inactive conformation of EGFR. In embodiments, the EGFR inhibitor increases degradation of EGFR. In embodiments, the EGFR inhibitor inhibits post-translational modification of EGFR. In embodiments, the EGFR inhibitors is gefitinib, erlotinib, cetuximab, lapatinib, panitumumab, vandetanib, afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626, zalutumumab, nimotuzumab, matuzumab, AP26113, or CO-1686. Other EGFR inhibitors are well known in the art and determining that such EGFR inhibitors may be examples of "EGFR inhibitors" is within the skill of a person of ordinary skill in the art.

The term "immunostimulant" is used in accordance with its plain ordinary meaning and refers to a compound (e.g. antibody, drug) that increases the activity of the immune system. In embodiments, the immunostimulant is an anti-cancer immunostimulant. In embodiments, the immunostimulant is deoxycholic acid, imiquimod, resiquimod, an antibody, a cytokine, beta-glucans, a Toll-like receptor agonist, an RIG-I-like receptor agonist, a CD39 antagonist, a CD73 antagonist, a PD-1 inhibitor, a PD-L1 inhibitor, a PD-L2 inhibitor, a CTLA-4 inhibitor, a TIGIT inhibitor, a BTLA inhibitor, a LAG-3 inhibitor, a TIM-3 inhibitor, a 2B4 inhibitor, a CD160 inhibitor, a LIGHT/HVEM inhibitor, a GITR activator, an OX40 activator, a 41BB activator, an ICOS activator, a CD27 activator, a regulatory T cell depleting agent, or myeloid derived suppressor cell depleting agent. In embodiments, the immunostimulant is a Toll-like receptor 3 agonist. In embodiments, the immunostimulant is a Toll-like receptor 4 agonist. In embodiments, the immunostimulant is a Toll-like receptor 5 agonist. In embodiments, the immunostimulant is a Toll-like receptor 7 agonist. In embodiments, the immunostimulant is a Toll-like receptor 9 agonist. In embodiments, the immunostimulant is a RIG-I-like receptor agonist. In embodiments, the immunostimulant is a RIG-I receptor agonist. In embodiments, the immunostimulant is a MDA-5 receptor agonist. In embodiments, the immunostimulant is a CD39 antagonist, or a CD73 antagonist. In embodiments, the immunostimulant is a PD-1 inhibitor, a PD-L1 inhibitor, a PD-L2 inhibitor, a CTLA-4 inhibitor, a TIGIT inhibitor, a BTLA inhibitor, a LAG-3 inhibitor, a TIM-3 inhibitor, a 2B4 inhibitor, a CD160 inhibitor, a LIGHT/HVEM inhibitor. In embodiments, the immunostimulant is a GITR activator, an OX40 activator, a 41BB activator, an ICOS activator, a CD27 activator. In embodiments, the immunostimulant is a regulatory T cell depleting agent. In embodiments, the immunostimulant is a myeloid derived suppressor cell depleting agent.

II. Pharmaceutical Compositions

In an aspect is provided a pharmaceutical composition that includes a macrocyclic lactone, or pharmaceutically acceptable salt thereof, a second agent, and a pharmaceutically acceptable excipient. The second agent is a modulator of the ATP/P2X4/P2X7/Pannexin-1/Caspase-1 signaling pathway, an anti-cancer agent, an mTOR inhibitor, an ER inhibitor, an EGFR tyrosine kinase inhibitor, a Toll-like receptor agonist, an RIG-I-like receptor agonist, a CD39 antagonist, a CD73 antagonist, a PD-1 inhibitor, a PD-L1 inhibitor, a PD-L2 inhibitor, a CTLA-4 inhibitor, a TIGIT inhibitor, a BTLA inhibitor, a LAG-3 inhibitor, a TIM-3 inhibitor, a 2B4 inhibitor, a CD160 inhibitor, a LIGHT/HVEM inhibitor, a GITR activator, an OX40 activator, a 41BB activator, an ICOS activator, a CD27 activator, a regulatory T cell depleting agent, or myeloid derived suppressor cell depleting agent.

In embodiments, the second agent is a modulator of the ATP/P2X4/P2X7/Pannexin-1/Caspase-1 signaling pathway. In embodiments, the second agent is an anti-cancer agent. In embodiments, the second agent is an mTOR inhibitor. In embodiments, the second agent is an ER inhibitor. In embodiments, the second agent is an EGFR tyrosine kinase inhibitor. In embodiments, the second agent is a Toll-like receptor agonist. In embodiments, the second agent is a Toll-like receptor 3 agonist. In embodiments, the second agent is a Toll-like receptor 4 agonist. In embodiments, the second agent is a Toll-like receptor 5 agonist. In embodiments, the second agent is a Toll-like receptor 7 agonist. In embodiments, the second agent is a Toll-like receptor 9 agonist. In embodiments, the second agent is a RIG-I-like receptor agonist. In embodiments, the second agent is a RIG-I receptor agonist. In embodiments, the second agent is a MDA-5 receptor agonist. In embodiments, the second agent is a CD39 antagonist, or a CD73 antagonist. In embodiments, the second agent is a PD-1 inhibitor, a PD-L1 inhibitor, a PD-L2 inhibitor, a CTLA-4 inhibitor, a TIGIT inhibitor, a BTLA inhibitor, a LAG-3 inhibitor, a TIM-3 inhibitor, a 2B4 inhibitor, a CD160 inhibitor, a LIGHT/HVEM inhibitor. In embodiments, the second agent is a GITR activator, an OX40 activator, a 41BB activator, an ICOS activator, a CD27 activator. In embodiments, the second agent is a regulatory T cell depleting agent. In embodiments, the second agent is a myeloid derived suppressor cell depleting agent.

III. Methods of Treatment

In an aspect is provided a method of treating cancer in a patient in need thereof. The method including administering a therapeutically effective amount of a macrocyclic lactone and a modulator of the ATP/P2X4/P2X7/Pannexin-1/Caspase-1 signaling pathway. In embodiments the macrocyclic lactone is an avermectin or a milbemycin. In embodiments, the macrocyclic lactone is ivermectin, abamectin, doramectin, eprinomectin, selamectin, moxidectin, milbemycin oxime, nemadectin, or milbemectin. In embodiments, the macrocyclic lactone is ivermectin. In embodiments, the macrocyclic lactone is capable of crossing the blood-brain barrier. In embodiments, the macrocyclic lactone is not capable of crossing the blood-brain barrier. In embodiments, the macrocyclic lactone enhances the sensitivity of the ATP/P2X4/P2X7/Pannexin-1/Caspase-1 signaling pathway to ATP.

In embodiments a method of treating cancer in a patient in need thereof is provided. The method including administering a therapeutically effective amount of a macrocyclic lactone. In embodiments, the macrocyclic lactone is ivermectin.

In embodiments, the modulator of the ATP/P2X4/P2X7/Pannexin-1/Caspase-1 signaling pathway is a P2X7 agonist. In embodiments, the modulator of the ATP/P2X4/P2X7/Pannexin-1/Caspase-1 signaling pathway is ATP, ATP analog, ATP precursor (e.g. adenosine diphosphate, adenosine monophosphate), or chemical derivative thereof (e.g. 2'(3')—O—(4-benzoylbenzoyl)adenosine-5'-triphosphate (BzATP), 7-deaza-adenosine analog, 5'-N-ethylcarboxamidoadenosine, 3"-ethynyladenosine, formycin, BCX4430, N6-2-(4-aminophenyl) ethyladenosine, toyocamycin, N6-(3-methoxyl-4-hydroxybenzyl) adenine riboside (B2), 2-chloroadenosine). In embodiments, the modulator of the ATP/P2X4/P2X7/Pannexin-1/Caspase-1 signaling pathway is ATP. In embodiments, the modulator of the ATP/P2X4/P2X7/Pannexin-1/Caspase-1 signaling pathway is an ATP analog. In embodiments, the modulator of the ATP/P2X4/P2X7/Pannexin-1/Caspase-1 signaling pathway is an ATP derivative. In embodiments, the modulator of the ATP/P2X4/P2X7/Pannexin-1/Caspase-1 signaling pathway is BzATP.

In embodiments, the modulator of the ATP/P2X4/P2X7/Pannexin-1/Caspase-1 signaling pathway is a Liver X receptor ligand. In embodiments, the modulator of the ATP/P2X4/P2X7/Pannexin-1/Caspase-1 signaling pathway is a Liver X receptor agonist. In embodiments, the Liver X receptor agonist is a derivative of cholesterol. In embodiments, the Liver X receptor agonist is a nonsteroidal agonist. In embodiments, the Liver X receptor agonist is an 22(R)-hydroxycholesterol, 24(S)-hydroxycholesterol, 27-hydroxycholesterol, and cholestenoic acid, 9-cis-retinoic acid, hypocholamide, N,N-dimethyl-3beta-hydroxy-cholenamide (DMHCA), T0901317, or GW3965. In embodiments, the Liver X receptor agonist is T0901317. In embodiments, the Liver X receptor agonist is GW3965.

In an aspect is provided a method of treating cancer in a patient in need thereof. The method including administering a therapeutically effective amount of a macrocyclic lactone, or a pharmaceutically acceptable salt thereof, and a therapy selected from the group consisting of a reactive oxygen species inducing therapy, an ATP releasing therapy, an autophagy inducing therapy, irradiation therapy, cryoablation therapy, and thermal ablation therapy. In embodiments, a reactive oxygen species inducing therapy is also an ATP releasing therapy. In embodiments, a reactive oxygen species inducing therapy is also an autophagy inducing therapy. In embodiments, a reactive oxygen species inducing therapy is increased activation of NADPH oxidase. In embodiments, a reactive oxygen species inducing therapy is irradiation therapy, cryoablation therapy, or thermal ablation therapy. In embodiments, an ATP releasing therapy is administration of a pro-apoptotic drug such as doxorubicin or staurosporine. In embodiments, an ATP releasing therapy is also an autophagy inducing therapy. In embodiments, an ATP releasing therapy is also a reactive oxygen species inducing therapy. In embodiments, an ATP releasing therapy is also irradiation therapy, cryoablation therapy, or thermal ablation therapy. In embodiments, an autophagy inducing therapy is also an ATP releasing therapy. In embodiments, an autophagy inducing therapy is also a reactive oxygen species inducing therapy. In embodiments, an autophagy inducing therapy is also irradiation therapy, cryoablation therapy, or thermal ablation therapy. In embodiments, an autophagy inducing therapy is administration of tetrandrine. In embodiments, thermal ablation therapy is high-intensity focused ultrasound therapy, radiofrequency therapy, microwave therapy, or laser ablation therapy. In embodiments, thermal ablation therapy is high-intensity focused ultrasound therapy. In embodiments, thermal ablation therapy is radiofrequency therapy. In embodiments, thermal ablation therapy is microwave therapy. In embodiments, thermal ablation therapy is laser ablation therapy.

In an aspect is provided a method of treating cancer in a patient in need thereof, the method including administering a therapeutically effective amount of a macrocyclic lactone, or a pharmaceutically acceptable salt thereof, and an anti-cancer agent. In embodiments, the anti-cancer agent is doxorubicin. In embodiments, the anti-cancer agent is taxol, vincristine, vinblastine, vinorelbine, vindesine, podophyllotoxin, paclitaxel, or docetaxel. In embodiments, the anti-cancer agent is taxol. In embodiments, the anti-cancer agent is docetaxel. In embodiments, the anti-cancer agent is paclitaxel. In embodiments, the anti-cancer agent is a proteasome inhibitor. In embodiments, the anti-cancer agent is lactacystin, disulfiram, epigallocatchin-3-gallate, salinosporamide A, epoxomicin, bortezomib, carfilizomib, MG132, ONX 0912, CEP-18770, MLN9708, or ixazomib. In embodiments, the anti-cancer agent is bortezomib or carfilizomib. In embodiments, the anti-cancer agent is bortezomib. In embodiments, the anti-cancer agent is carfilizomib.

In an aspect is provided a method of treating cancer in a patient in need thereof, the method including administering a therapeutically effective amount of a macrocyclic lactone, or a pharmaceutically acceptable salt thereof, and a protein inhibitor selected from the group consisting of an mTOR inhibitor, an ER inhibitor, or an EGFR tyrosine kinase inhibitor. In embodiments, the mTOR inhibitor is rapamycin or rapamycin derivatives (e.g. sirolimus, temsirolimus, everolimus, deforolimus). In embodiments, the ER inhibitor is tamoxifen. In embodiments, the ER inhibitor is an antiestrogen, an aromatase inhibitor, SERM, fluvestrant, clomifene, femarelle, ormeloxifene, raloxifene, tamoxifen, toremifene, lasofoxifene, ospemifene, anastrozole, letrozole, exemestane, vorozole, formestane, fadrozole, aminoglutethimide, and testolactone. In embodiments, the ER inhibitor is fluvestrant, clomifene, femarelle, ormeloxifene, raloxifene, tamoxifen, toremifene, lasofoxifene, and ospemifene. In embodiments, the EGFR tyrosine kinase inhibitor is an antibody. In embodiments, the EGFR tyrosine kinase inhibitor is lapatinib, cetuximab, or trastuzumab. In embodiments, the EGFR tyrosine kinase inhibitor is gefitinib, erlotinib, cetuximab, lapatinib, panitumumab, vandetanib, afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626, zalutumumab, nimotuzumab, matuzumab, AP26113, or CO-1686.

In an aspect is provided a method of treating cancer in a patient in need thereof, the method including administering a therapeutically effective amount of a macrocyclic lactone, or a pharmaceutically acceptable salt thereof, and a bacterial agent. In embodiments the bacterial agent is a *Streptococcus mitis, Staphylococcus epidermis, Bacillus* sp., *Mycoplasma* sp., *Chlamydophila, pneumonia, Robinsoniella peoriensis, Pedioccocus acidilactici, Leuconostoc lactis, L. mesenteroides, Staphylococcus epidermidis, Mycoplasma* sp., *Ralstonia insidiosa, Fusobacterium naviforme, Prevotella* sp., *Salmonella typhi, H. pylori, H. hepaticus, H. bilis, Chlamydia pneumonia, C. trachomatis, C. psittaci, Chlamydia trachomatis, Mycoplasma* sp., *Streptococcus gallolyticus, Fusobacterium nucleatum, F. necrophorum, F. mortiferum, F. perfoetens, Roseburia* sp., *Faecalibacterium* sp., *Escherichia coli, Citrobacter* sp., *H. pylori,* or *Mycoplasma* sp. species. In embodiments, the bacterial agent is bacteria, modified bacteria, engineered bacteria, or fragment thereof.

In an aspect is provided a method of treating cancer in a patient in need thereof, the method including administering a therapeutically effective amount of a macrocyclic lactone, or a pharmaceutically acceptable salt thereof, and an oncolytic virus. The term "oncolytic virus" is used according to its plain ordinary meaning and refers to a virus that preferentially infects and kills cancer cells. In embodiments, the oncolytic virus is a modified virus, engineered virus, or fragment thereof. In embodiments, the oncolytic virus may be replaced with a viral antigen. In embodiments, the oncolytic virus is an adenovirus, reovirus, measles, herpes simplex, or Newcastle disease virus. In embodiments, the oncolytic virus is talimogene laherparepvec, H101, Onyx-15, Vesicular stomatitis virus, poliovirus, reolysin, senecavirus, or RIGVIR.

In an aspect is provided a method of treating cancer in a patient in need thereof, the method including administering a therapeutically effective amount of a macrocyclic lactone, or a pharmaceutically acceptable salt thereof, and an immunostimulant. In embodiments, the immunostimulant includes a Toll-like receptor agonist or a RIG-I-like receptor agonist. In embodiments, the Toll-like receptor agonist is a TLR3, TLR4, TLR5, TLR7, or TLR9 agonist. In embodiments, the Toll-like receptor agonist is Pam3Cyc, CFA, MALP2, Pam2Cys, FSL-1, Hib-OMPC, AGP, MPL A, RC-529, MDF2β, CFA, Flagellin, guanosine analogs, imidazoquinolines (e.g. Imiquimod, R848, loxoribine), Hsp60, Hsp70, fibronectin domain A, polyribosinic:polyribocytidic acid, polyadenosine-polyuridylic acid (poly AU) Ampligen (polyI:polyC U; Hemispherx Biopharma) and Polyinosinic-Polycytidylic acid stabilized with poly-L-lysine and carboxymethylcellulose (Poly-ICLC, HILTONOL®), Monophosphoryl lipid A, synthetic oligonucleotides containing unmethylated CpG dinucleotide (CpG-ODN), or HMGB-1. In embodiments, the RIG-I-like receptor agonist is 5'ppp-dsRNA or a poly(deoxyadenylic-deoxythymidylic) acid sodium salt.

In embodiments, the immunostimulant includes a CD39 antagonist or a CD73 antagonist. In embodiments, the CD39 antagonist is ARL67156. In embodiments, the CD39 antagonist is PSB 069. In embodiments, the CD39 antagonist is a CD39 antibody. In embodiments, the CD39 antagonist is a CD39 humanized antibody. In embodiments, the CD39 antagonist is a CD39 chimeric antibody. In embodiments, the CD73 antagonist is a CD73 antibody. In embodiments, the CD73 antagonist is a CD73 humanized antibody. In embodiments, the CD73 antagonist is a CD73 chimeric antibody. In embodiments, the CD73 inhibitor is α,β-methylene ADP.

In embodiments, immunostimulant includes a PD-1 inhibitor, a PD-L1 inhibitor, a PD-L2 inhibitor, a CTLA-4 inhibitor, a TIGIT inhibitor, a BTLA inhibitor, a LAG-3 inhibitor, a TIM-3 inhibitor, a 2B4 inhibitor, a CD 160 inhibitor, or a LIGHT/HVEM inhibitor.

In embodiments, the immunostimulant includes a GITR activator, an OX40 activator, a 41BB activator, an ICOS activator, or a CD27 activator.

In embodiments, the immunostimulant reduces the level of regulatory T cells. In embodiments, the immunostimulant reduces the level of regulatory T cells relative to the absence of the immunostimulant.

In embodiments, the immunostimulant reduces the level of myeloid derived suppressor cells. In embodiments, the immunostimulant reduces the level of myeloid derived suppressor cells relative to the absence of the immunostimulant.

In an aspect is provided a pharmaceutical composition comprising a macrocyclic lactone, or pharmaceutically acceptable salt thereof, a second agent, and a pharmaceutically acceptable excipient. The second agent is a modulator of the ATP/P2X4/P2X7/Pannexin-1/Caspase-1 signaling pathway, an anti-cancer agent, an mTOR inhibitor, an ER inhibitor, an EGFR tyrosine kinase inhibitor, a Toll-like receptor agonist, an RIG-I-like receptor agonist, a CD39 antagonist, a CD73 antagonist, a PD-1 inhibitor, a PD-L1 inhibitor, a PD-L2 inhibitor, a CTLA-4 inhibitor, a TIGIT inhibitor, a BTLA inhibitor, a LAG-3 inhibitor, a TIM-3 inhibitor, a 2B4 inhibitor, a CD160 inhibitor, a LIGHT/HVEM inhibitor, a GITR activator, an OX40 activator, a 41BB activator, an ICOS activator, a CD27 activator, a regulatory T cell depleting agent, or myeloid derived suppressor cell depleting agent.

In an aspect is provided a method of treating cancer in a patient in need of the treatment, the method including administering a pharmaceutical composition comprising a macrocyclic lactone, or pharmaceutically acceptable salt thereof, a second agent, and a pharmaceutically acceptable excipient as described herein (including in an aspect, embodiment, table, figure, claim, sequence listing, or example).

In an aspect is provided a pharmaceutical composition comprising a macrocyclic lactone, or pharmaceutically acceptable salt thereof, a second agent, and a pharmaceutically acceptable excipient as described herein (including in an aspect, embodiment, table, figure, claim, sequence listing, or example) for use in the manufacture of a medicament for treatment of a disease (e.g., cancer). The use may include administering to the subject a therapeutically effective amount of a pharmaceutical composition described herein.

In an aspect is provided a pharmaceutical composition comprising a macrocyclic lactone, or pharmaceutically acceptable salt thereof, a second agent, and a pharmaceutically acceptable excipient as described herein (including in an aspect, embodiment, table, figure, claim, sequence listing, or example) for use in the treatment of a cancer in a subject in need of such treatment. The use includes administering to the subject a pharmaceutical composition described herein. The use may include administering to the subject a therapeutically effective amount of a pharmaceutical composition described herein.

In embodiments, the method or use includes administering a therapeutically effective amount of a pharmaceutical composition described herein (including in an aspect, embodiment, table, figure, claim, sequence listing, or example).

In embodiments, the method or use includes systemic administration of the pharmaceutical composition. In embodiments, the method or use includes parenteral administration of the pharmaceutical composition. In embodiments, the method or use includes intravenous administration of the pharmaceutical composition. In embodiments, the method or use includes administration directly to a tumor. In embodiments, the method or use includes local administration to the site of cancer.

In embodiments, the cancer is a hematopoietic cell cancer. In embodiments, the cancer is not a hematopoietic cell cancer. In embodiments, the cancer is breast cancer, melanoma, head and neck cancer, lung cancer, gastric cancer, mesothelioma, glioblastoma, medulloblastoma, cervical cancer, ovarian cancer, pancreatic cancer, prostate cancer, esophageal cancer, skin cancer, brain cancer, colorectal cancer, leukemia, lymphoma, myeloma, or hematological malignancies. In embodiments, the cancer is prostate cancer (e.g. castration-resistant). In embodiments, the cancer is breast cancer (e.g. triple negative). In embodiments, the cancer is glioblastoma. In embodiments, the cancer is ovarian cancer. In embodiments, the cancer is lung cancer. In embodiments, the cancer is head and neck cancer. In embodiments, the cancer is esophageal cancer. In embodiments, the cancer is skin cancer. In embodiments, the cancer is melanoma. In embodiments, the cancer is brain cancer. In embodiments, the cancer is colorectal cancer. In embodiments, the cancer is leukemia (e.g. AML, ALL, or CML). In embodiments, the cancer is lymphoma. In embodiments, the cancer is myeloma (e.g. multiple myeloma). In embodiments, the cancer is squamous cell carcinoma (e.g. head and neck cancer or esophageal cancer). In embodiments, the cancer is metastatic cancer. In embodiments, the cancer is acute myeloid leukemia. In embodiments, the cancer is B cell lymphoma. In embodiments, the cancer is multiple myeloma. In embodiments, the cancer is a drug-resistant cancer. In embodiments, the cancer is therapy-resistant cancer.

In embodiments, the cancer includes an increased level of P2X4 relative to a control (e.g. non-cancerous cell of the same type as the cancer cell). Cancerous cells, (e.g., breast cancer, melanoma, head and neck cancer, lung cancer, gastric cancer, mesothelioma, glioblastoma, medulloblastoma, cervical cancer, ovarian cancer, pancreatic cancer, prostate cancer, or hematological malignancies, or therapy-resistant forms thereof) can express P2X4 a level of at least about 5%, 10%, 15%, 20%, 25%, 30%, 35%, 40%, 45%, 50%, 55%, 60%, 65%, 70%, 75%, 80%, 85%, 90%, 95%, 105%, 110%, 115%, 120%, 125%, 130%, 135%, 140%, 145%, 150%, 155%, 160%, 165%, 170%, 175%, 180%, 185%, 190%, 195%, in comparison to a control such as normal, non-cancerous cells. Cancerous cells can also have at least about a 1-fold, 2-fold, 3-fold, 4-fold, 5-fold, 6-fold, 7-fold, or higher level of P2X4 transcription or translation in comparison to a control such as normal, non-cancerous cells. In certain instances, the cancer cell sample is autologous. In embodiments, the cancer includes an increased level of P2X7 relative to a control (e.g. non-cancerous cell of the same type as the cancer cell). Cancerous cells, (e.g., breast cancer, melanoma, head and neck cancer, lung cancer, gastric cancer, mesothelioma, glioblastoma, medulloblastoma, cervical cancer, ovarian cancer, pancreatic cancer, prostate cancer, hematological malignancies, or therapy-resistant forms thereof) can express P2X7 a level of at least about 5%, 10%, 15%, 20%, 25%, 30%, 35%, 40%, 45%, 50%, 55%, 60%, 65%, 70%, 75%, 80%, 85%, 90%, 95%, 105%, 110%, 115%, 120%, 125%, 130%, 135%, 140%, 145%, 150%, 155%, 160%, 165%, 170%, 175%, 180%, 185%, 190%, 195%, in comparison to a control such as normal, non-cancerous cells. Cancerous cells can also have at least about a 1-fold, 2-fold, 3-fold, 4-fold, 5-fold, 6-fold, 7-fold, or higher level of P2X7 transcription or translation in comparison to normal, non-cancerous cells. In certain instances, the cancer cell sample is autologous. In embodiments, the cancer includes an increased level of P2X purinergic receptors, P2Y purinergic receptors, NOX family members, GABA, or glycine receptors relative to a control (e.g. non-cancerous cell of the same type as the cancer cell).

In an aspect is provided a method of inhibiting the growth of a cancer cell including contacting the cancer cell with a pharmaceutical composition comprising a macrocyclic lactone, or pharmaceutically acceptable salt thereof, a second agent, and a pharmaceutically acceptable excipient as described herein (including in an aspect, embodiment, table, figure, claim, sequence listing, or example).

In an aspect is provided a pharmaceutical composition comprising a macrocyclic lactone, or pharmaceutically acceptable salt thereof, a second agent, and a pharmaceutically acceptable excipient as described herein (including in an aspect, embodiment, table, figure, claim, sequence listing, or example) for use in inhibiting the growth of a cancer cell. The use includes contacting the cancer cell with a pharmaceutical composition described herein. The use may include contacting the cancer cell with an effective amount of a pharmaceutical composition described herein.

In an aspect is provided a pharmaceutical composition comprising a macrocyclic lactone, or pharmaceutically acceptable salt thereof, a second agent, and a pharmaceutically acceptable excipient as described herein (including in an aspect, embodiment, table, figure, claim, sequence listing, or example) for use in the manufacture of a medicament for inhibiting the growth of a cancer cell.

In embodiments, the method or use includes inducing apoptosis of a cancer cell. In embodiments, the method or use includes inducing apoptosis in a cancer cell but not substantially in a non-cancer cell. In embodiments, the method or use includes inducing apoptosis in a cancer cell in a patient but not substantially in a non-cancer cell in the same patient. In embodiments, the method or use includes inducing apoptosis in a cancer cell but not a non-cancer cell of the same cell type as the cancer cell (e.g. lung cell, breast cell, pancreatic cell, colorectal cell, prostate cell, hematopoietic cell). In embodiments, the cancer cell is in an organ. In embodiments, the cancer cell is in a bone. In embodiments, the cancer cell is in bone.

In embodiments, the method or use includes inducing necrosis of a cancer cell. In embodiments, the method or use includes inducing necrosis in a cancer cell but not substantially in a non-cancer cell. In embodiments, the method or use includes inducing necrosis in a cancer cell in a patient but not substantially in a non-cancer cell in the same patient. In embodiments, the method or use includes inducing necrosis in a cancer cell but not a non-cancer cell of the same cell type as the cancer cell (e.g. lung cell, breast cell, pancreatic cell, colorectal cell, prostate cell, hematopoietic cell). In embodiments, the cancer cell is in a bone. In embodiments, the cancer cell is in bone.

In embodiments, the method or use includes inducing necrosis and apoptosis of a cancer cell. In embodiments, the method or use includes inducing necrosis and apoptosis in a cancer cell but not a non-cancer cell. In embodiments, the method or use includes inducing necrosis and apoptosis in a cancer cell in a patient but not substantially in a non-cancer cell in the same patient. In embodiments, the method or use includes inducing necrosis and apoptosis in a cancer cell but not substantially in a non-cancer cell of the same cell type as the cancer cell (e.g. lung cell, breast cell, pancreatic cell, colorectal cell, prostate cell, hematopoietic cell). In embodiments, the cancer cell is in a bone. In embodiments, the cancer cell is in bone.

In embodiments, the method or use includes inducing pyroptosis of a cancer cell. In embodiments, the method or use includes inducing pyroptosis in a cancer cell but not substantially in a non-cancer cell. In embodiments, the method or use includes inducing pyroptosis in a cancer cell in a patient but not a non-cancer cell in the same patient. In embodiments, the method or use includes inducing pyroptosis in a cancer cell but substantially in not a non-cancer cell of the same cell type as the cancer cell (e.g. lung cell, breast cell, pancreatic cell, colorectal cell, prostate cell, hematopoietic cell). In embodiments, the cancer cell is in a bone. In embodiments, the cancer cell is in bone.

Embodiments

Embodiments contemplated herein include embodiments P1 to P48 following.

Embodiment P1. A method of treating cancer in a patient in need thereof, the method comprising administering a therapeutically effective amount of a macrocyclic lactone and a modulator of the ATP/P2X4/P2X7/Pannexin-1/Caspase-1 signaling pathway.

Embodiment P2. The method of embodiment P1, wherein the modulator of the ATP/P2X4/P2X7/Pannexin-1/Caspase-1 signaling pathway is a P2X7 agonist.

Embodiment P3. The method of either embodiments P1 or P2, wherein the modulator of the ATP/P2X4/P2X7/Pannexin-1/Caspase-1 signaling pathway is ATP or an ATP analog.

Embodiment P4. The method of any one of embodiments P1-P3, wherein the modulator of the ATP/P2X4/P2X7/Pannexin-1/Caspase-1 signaling pathway is BzATP.

Embodiment P5. The method of embodiment P1, wherein modulator of the ATP/P2X4/P2X7/Pannexin-1/Caspase-1 signaling pathway is a Liver X receptor ligand.

Embodiment P6. The method of embodiment P5, wherein the Liver X Receptor ligand is T0901317.

Embodiment P7. A method of treating cancer in a patient in need thereof, the method comprising administering a therapeutically effective amount of a macrocyclic lactone, or a pharmaceutically acceptable salt thereof, and a therapy selected from the group consisting of a reactive oxygen species inducing therapy, an ATP releasing therapy, an autophagy inducing therapy, irradiation therapy, cryoablation therapy, and thermal ablation therapy.

Embodiment P8. The method of embodiment P7, wherein the therapy is reactive oxygen species inducing therapy.

Embodiment P9. The method of embodiment P7, wherein the therapy is ATP releasing therapy.

Embodiment 10. The method of embodiment 7P, wherein the therapy is autophagy inducing therapy.

Embodiment P11. The method of embodiment P7, wherein the therapy is irradiation therapy.

Embodiment P12. The method of embodiment P7, wherein the therapy is cryoablation therapy.

Embodiment P13. The method of embodiment P7, wherein the therapy is thermal ablation therapy.

Embodiment P14. A method of treating cancer in a patient in need thereof, the method comprising administering a therapeutically effective amount of a macrocyclic lactone, or a pharmaceutically acceptable salt thereof, and an anti-cancer agent.

Embodiment P15. The method of embodiment P14, wherein the anti-cancer agent is doxorubicin.

Embodiment P16. The method of embodiment P14, wherein the anti-cancer agent is taxol.

Embodiment P17. The method of embodiment P14, wherein the anti-cancer agent is a proteasome inhibitor.

Embodiment P18. The method of embodiments P14 or P17, wherein the anti-cancer agent is bortezomib or carfilizomib.

Embodiment P19. A method of treating cancer in a patient in need thereof, the method comprising administering a therapeutically effective amount of a macrocyclic lactone, or a pharmaceutically acceptable salt thereof, and a protein inhibitor selected from the group consisting of an mTOR inhibitor, an ER inhibitor, or an EGFR tyrosine kinase inhibitor.

Embodiment P20. The method of embodiment P19, wherein the protein inhibitor is a mTOR inhibitor.

Embodiment P21. The method of embodiment P19, wherein the protein inhibitor is a ER inhibitor.

Embodiment P22. The method of embodiment P19, wherein the protein inhibitor is a EGFR tyrosine kinase inhibitor.

Embodiment P23. The method of any one of embodiments P19-P22, wherein the protein inhibitor is an antibody.

Embodiment P24. A method of treating cancer in a patient in need thereof, the method comprising administering a therapeutically effective amount of a macrocyclic lactone, or a pharmaceutically acceptable salt thereof, and a bacterial agent.

Embodiment P25. A method of treating cancer in a patient in need thereof, the method comprising administering a therapeutically effective amount of a macrocyclic lactone, or a pharmaceutically acceptable salt thereof, and an oncolytic virus.

Embodiment 26. A method of treating cancer in a patient in need thereof, the method comprising administering a therapeutically effective amount of a macrocyclic lactone, or a pharmaceutically acceptable salt thereof, and an immunostimulant.

Embodiment P27. The method of embodiment P26, wherein the immunostimulant comprises a Toll-like receptor agonist or a RIG-I-like receptor agonist.

Embodiment 28. The method of embodiment P26, wherein the immunostimulant comprises a CD39 antagonist or a CD73 antagonist.

Embodiment 29. The method of embodiment P26, wherein the immunostimulant comprises a PD-1, PD-L1, PD-L2, CTLA-4, TIGIT, BTLA, LAG-3, TIM-3, 2B4, CD160, or LIGHT/HVEM inhibitor.

Embodiment P30. The method of embodiment P26, wherein the immunostimulant comprises a GITR, OX40, 41BB, ICOS, or CD27 agonist.

Embodiment P31. The method of embodiment P26, wherein the immunostimulant reduces the level of regulatory T cells.

Embodiment P32. The method of embodiment P26, wherein the immunostimulant reduces the level of myeloid derived suppressor cells.

Embodiment 33. The method of any one of embodiments P1-P26, wherein the cancer is breast cancer, melanoma, head and neck cancer, lung cancer, gastric cancer, mesothelioma, glioblastoma, medulloblastoma, cervical cancer, ovarian cancer, pancreatic cancer, prostate cancer, or hematological malignancies.

Embodiment P34. The method of any one of embodiments P1-P26, wherein the cancer is triple negative breast cancer.

Embodiment P35. The method of any one of embodiments P1-P34, wherein the macrocyclic lactone is an avermectin or a milbemycin.

Embodiment P36. The method of any one of embodiments P1-P35, wherein the macrocyclic lactone is ivermectin, abamectin, doramectin, eprinomectin, selamectin, moxidectin, milbemycin oxime, nemadectin, or milbemectin.

Embodiment P37. A pharmaceutical composition comprising a macrocyclic lactone, or pharmaceutically acceptable salt thereof, a second agent, and a pharmaceutically acceptable excipient, wherein the second agent is a modulator of the ATP/P2X4/P2X7/Pannexin-1/Caspase-1 signaling pathway, an anti-cancer agent, an mTOR inhibitor, an ER inhibitor, an EGFR tyrosine kinase inhibitor, a Toll-like receptor agonist, an RIG-I-like receptor agonist, a CD39 antagonist, a CD73 antagonist, a PD-1 inhibitor, a PD-L1 inhibitor, a PD-L2 inhibitor, a CTLA-4 inhibitor, a TIGIT inhibitor, a BTLA inhibitor, a LAG-3 inhibitor, a TIM-3 inhibitor, a 2B4 inhibitor, a CD160 inhibitor, a LIGHT/HVEM inhibitor, a GITR activator, an OX40 activator, a 41BB activator, an ICOS activator, a CD27 activator, a regulatory T cell depleting agent, or myeloid derived suppressor cell depleting agent.

Embodiment P38. The pharmaceutical composition of embodiment P37, wherein the second agent is a modulator of the ATP/P2X4/P2X7/Pannexin-1/Caspase-1 signaling pathway.

Embodiment P39. The pharmaceutical composition of embodiment P37, wherein the second agent is an anti-cancer agent.

Embodiment P40. The pharmaceutical composition of embodiment P37, wherein the second agent is an mTOR inhibitor.

Embodiment P41. The pharmaceutical composition of embodiment P37, wherein the second agent is an ER inhibitor.

Embodiment P42. The pharmaceutical composition of embodiment P37, wherein the second agent is an EGFR tyrosine kinase inhibitor.

Embodiment P43. The pharmaceutical composition of embodiment P37, wherein the second agent is a Toll-like receptor agonist or RIG-I-like receptor agonist.

Embodiment P44. The pharmaceutical composition of embodiment P37, wherein the second agent is a CD39 antagonist or CD73 antagonist.

Embodiment P45. The pharmaceutical composition of embodiment P37, wherein the second agent is a PD-1 inhibitor, a PD-L1 inhibitor, a PD-L2 inhibitor, a CTLA-4 inhibitor, a TIGIT inhibitor, a BTLA inhibitor, a LAG-3 inhibitor, a TIM-3 inhibitor, a 2B4 inhibitor, a CD160 inhibitor, a LIGHT/HVEM inhibitor.

Embodiment P46. The pharmaceutical composition of embodiment P37, wherein the second agent is a GITR activator, an OX40 activator, a 41BB activator, an ICOS activator, a CD27 activator.

Embodiment P47. The pharmaceutical composition of embodiment P37, wherein the second agent is a regulatory T cell depleting agent.

Embodiment P48. The pharmaceutical composition of embodiment P37, wherein the second agent is myeloid derived suppressor cell depleting agent.

EXAMPLES

The following examples are offered to illustrate, but not to limit the claimed invention.

Example 1

Figure 1B:
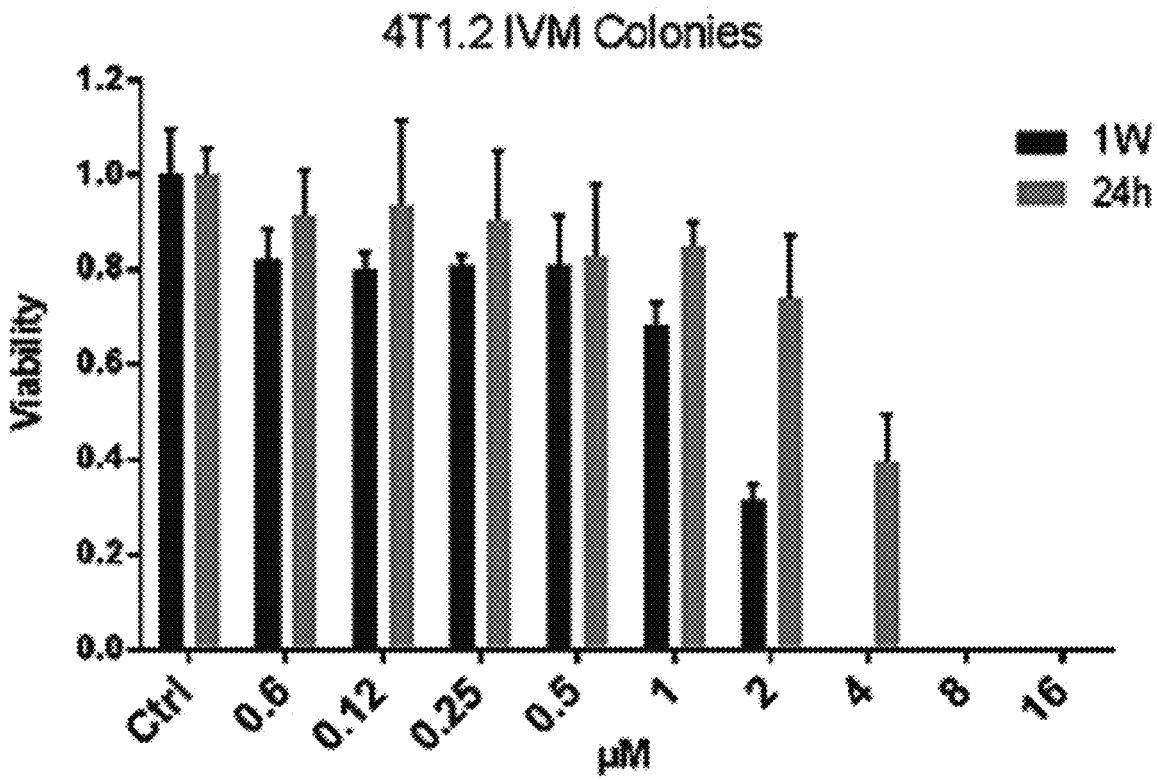
Figure 1C:
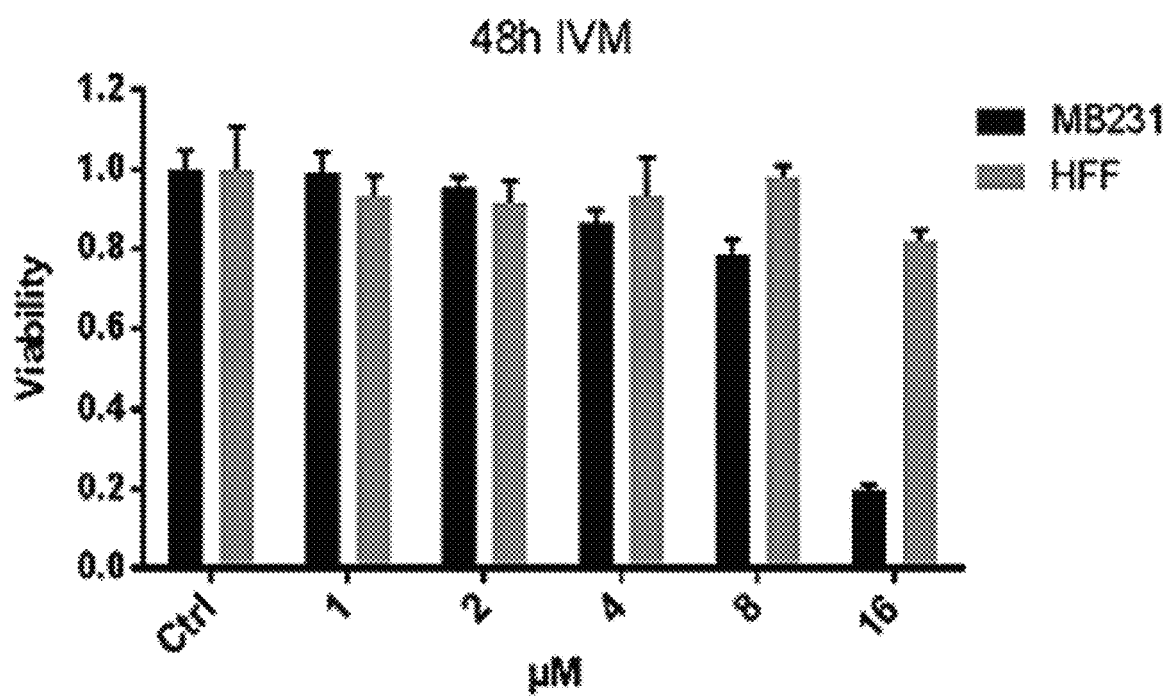
Figure 1D:
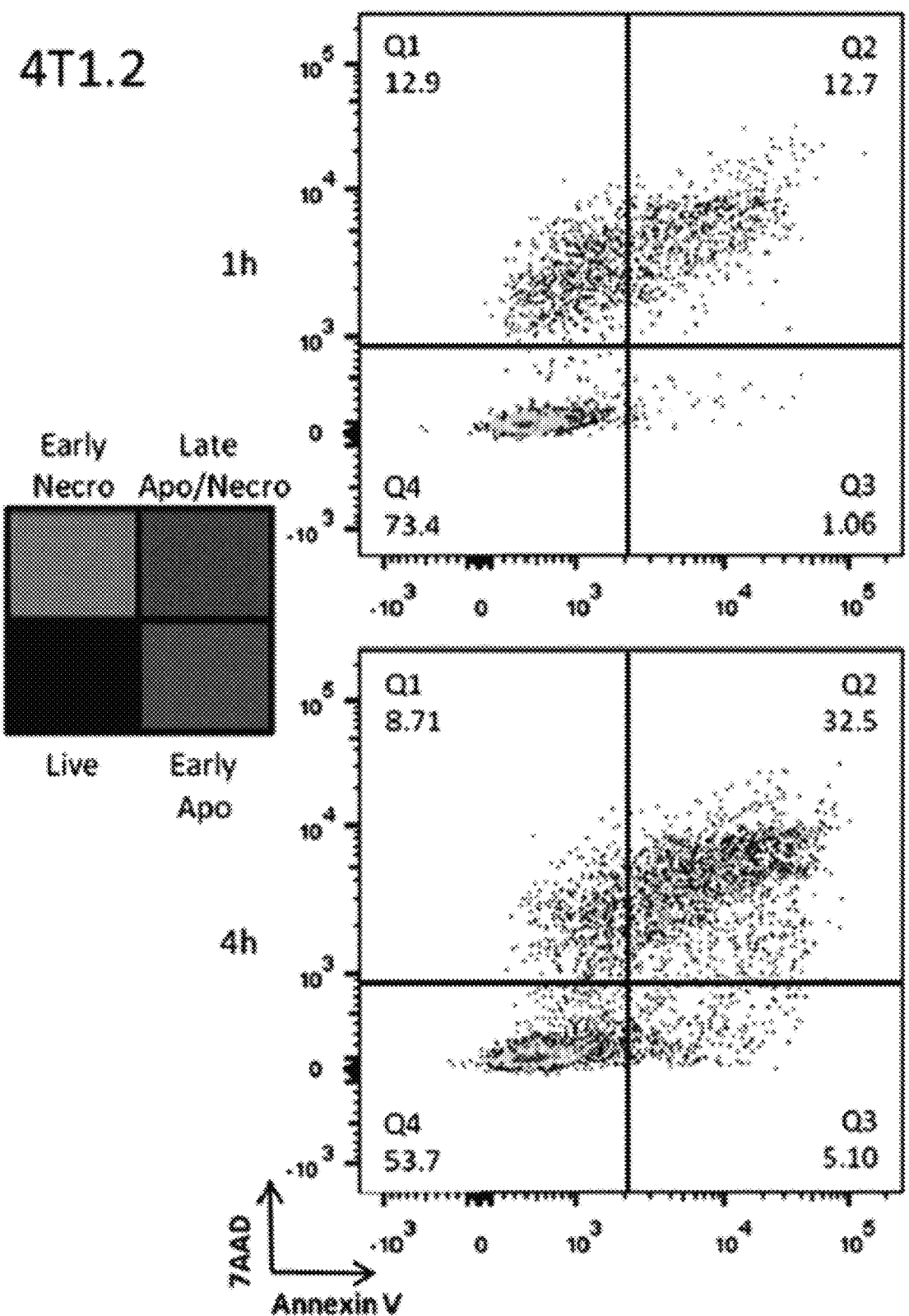
Figure 1E:
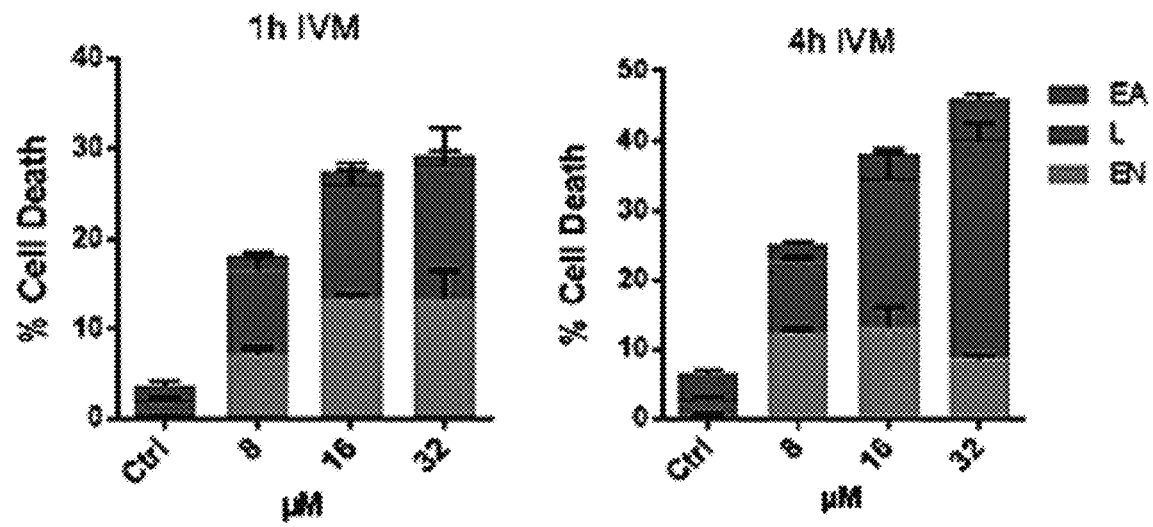

Ivermectin Kills Breast Cancer Cells Through a Mixed Apoptotic and Necrotic Mechanism Applicants investigated Ivermectin as a prototype agent to modulate purinergic signaling in breast cancer cells. Mouse and human triple negative breast cancer (TNBC) cells are sensitive to Ivermectin (FIG. 1A), which exhibited IC50 values as low as 2 µM with extended exposure time (FIG. 1B). Breast cancer cells manifested higher sensitivity than normal cells to Ivermectin (FIG. 1C). Despite being equivalent at 24 h, the kinetics of Ivermectin killing appears to be faster and more synchronized in mouse compared to human cancer cells. Rapid killing of mouse and human breast cancer cells occurred with Ivermectin doses of 8 µM (and higher), which were used for mechanistic studies in vitro. More than 90% of dying cancer cells became directly necrotic (7AAD-positive). The remainder went through an Annexin V/phosphatidylserine (PS) single-positive apoptotic phase that quickly progressed to secondary necrosis (FIGS. 1D-1E).

Figure 1F:
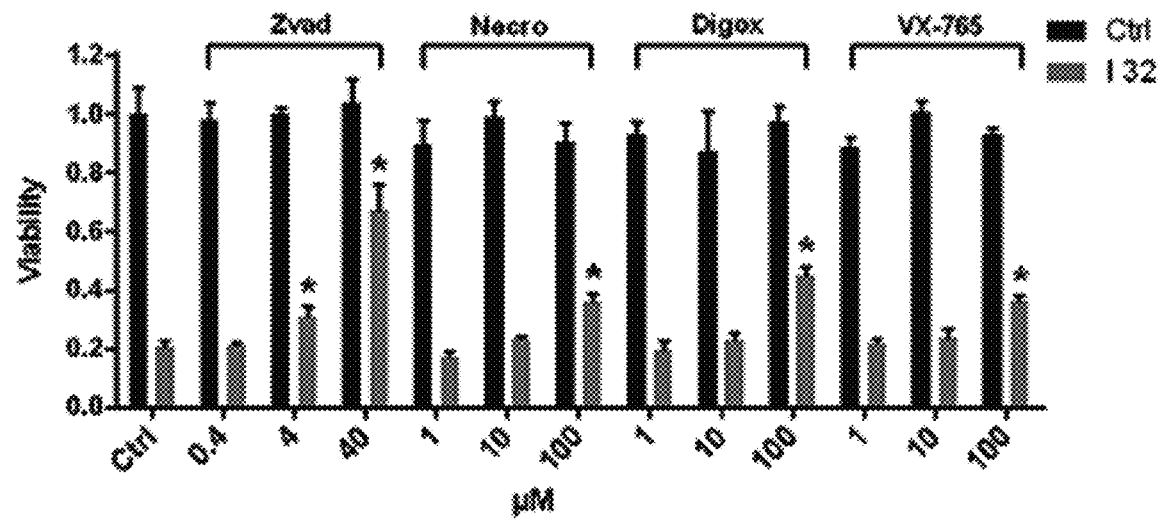
Figure 8A:
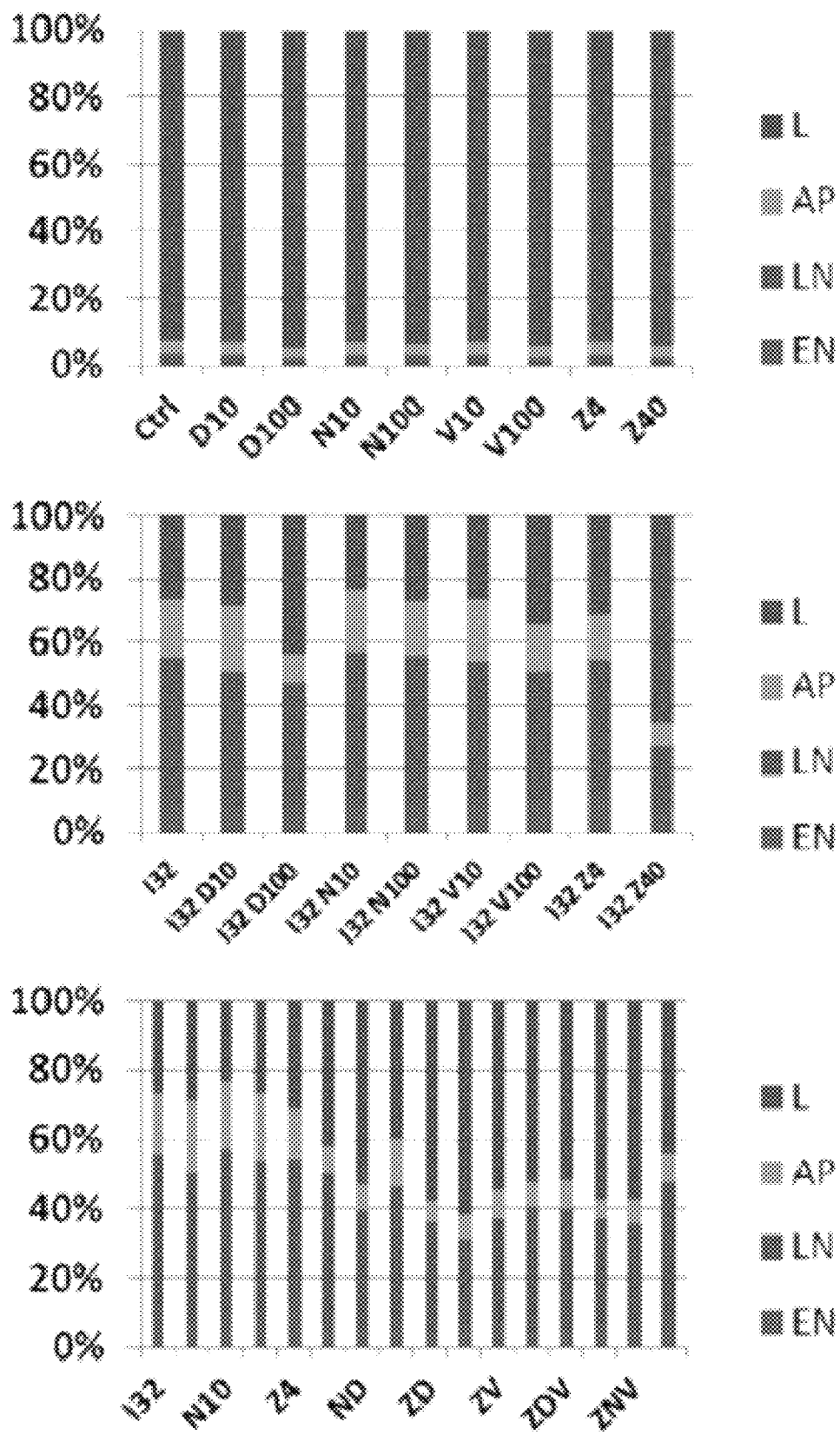
FIGS. 8A-8B. Ivermectin kills breast cancer cells through a mixed apoptotic and necrotic mechanism.

Necrosis appears predominant during the first 4 h of treatment, at which point the slower progressing apoptosis gains prominence. The pan-caspase inhibitor Z-vad-fmk inhibited cell death very effectively. The inhibitors of caspase-1 (VX-765), necroptosis (Necrostatin), and autosis (Digoxin) also demonstrated some protection (FIG. 1F). Combinations of inhibitors enhanced protection, which supports the involvement of multiple death pathways (FIG. 8A). To clarify, we investigated the downstream mediators of cell death.

Figure 1G:
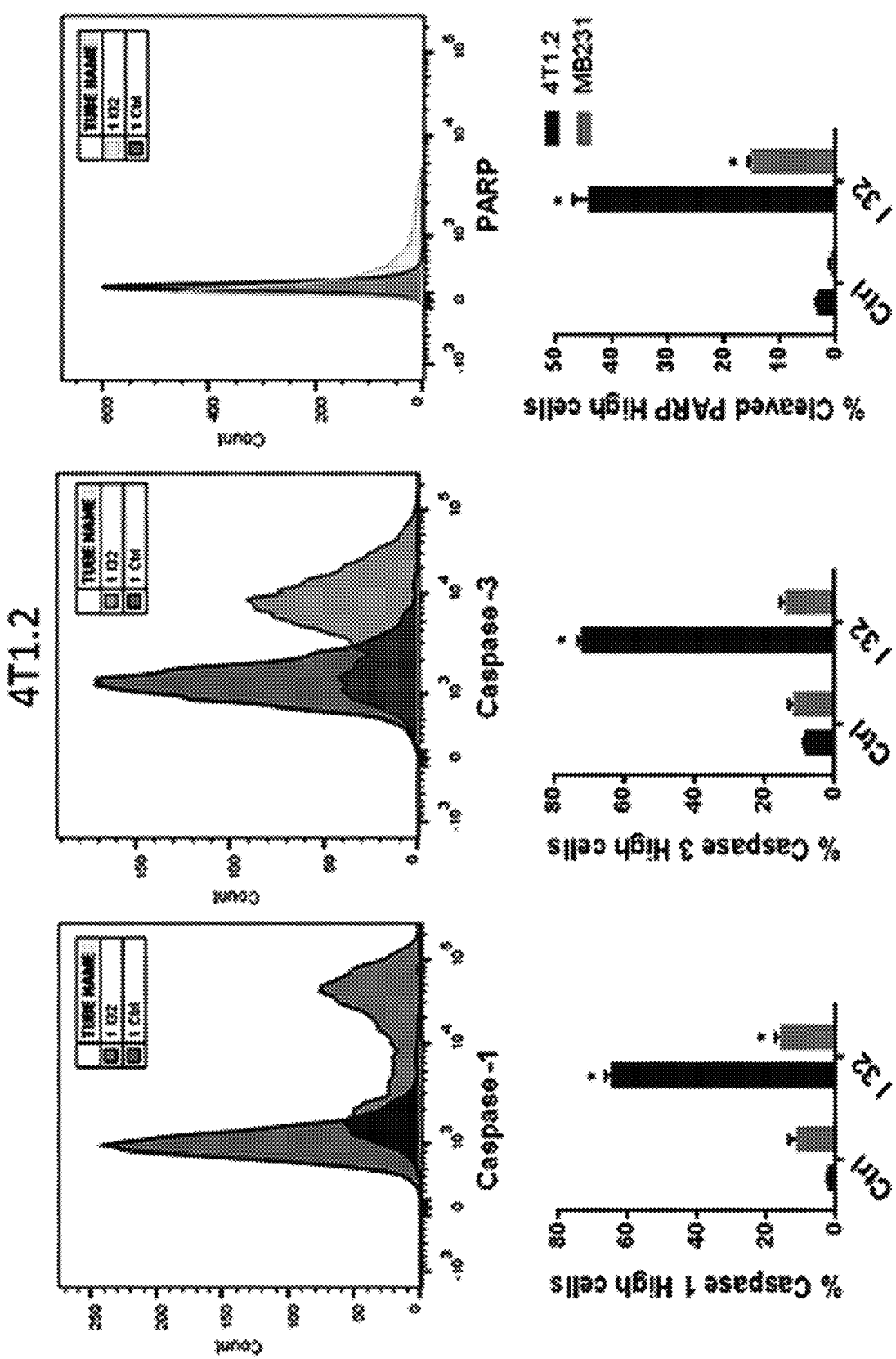
Figure 1H:
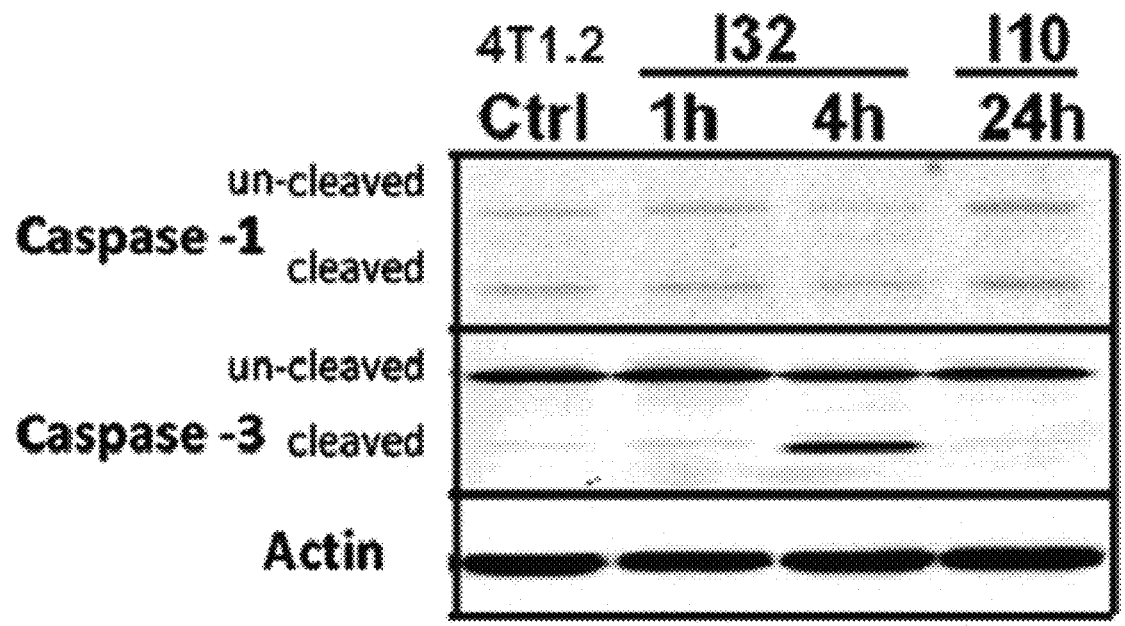
Figure 1H:
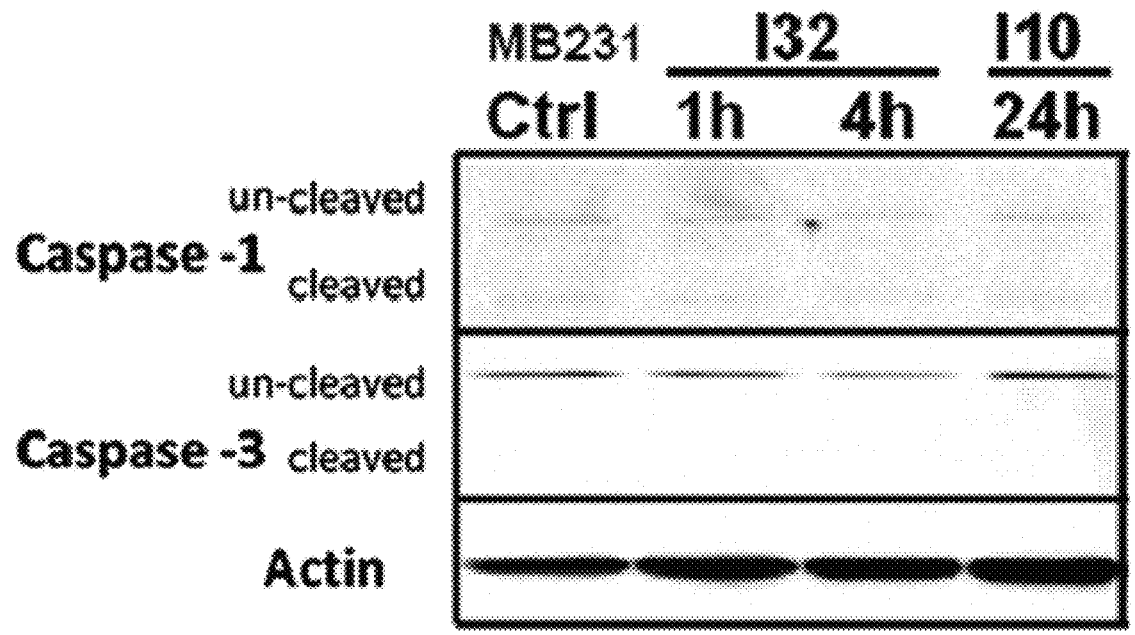
Figure 8B:
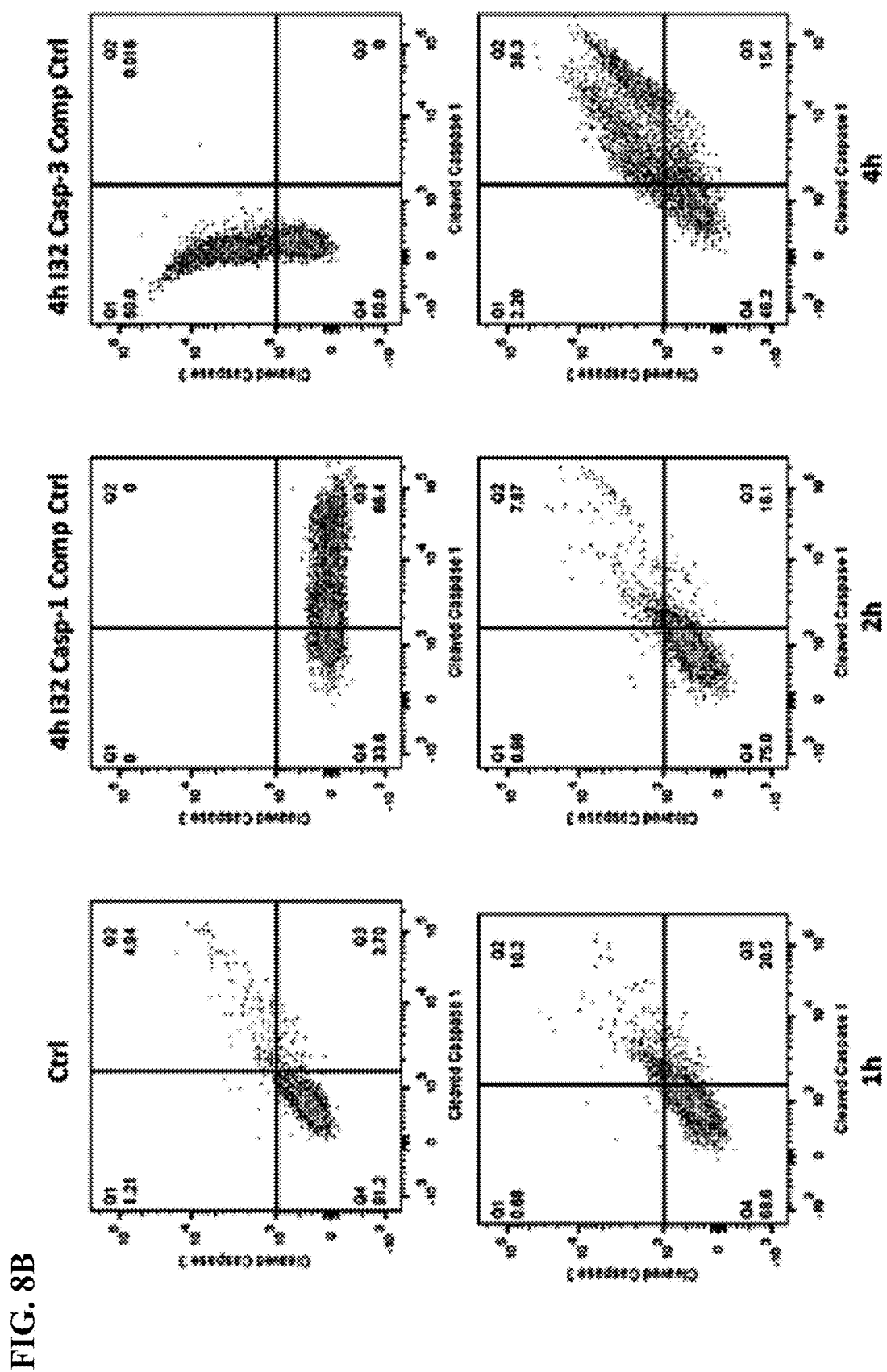

Cancer cells were treated with Ivermectin and analyzed for 1) PARP cleavage; 2) activation of caspase-1-a characteristic feature of the pyroptotic cell death pathway; and 3) caspase-3 activity typically observed in classical apoptosis. Ivermectin treatment results in rapid cleavage of PARP that occurs in the context of potent caspase-1 and caspase-3 activation (FIG. 1G). While dying cancer cells ultimately manifest cleavage of both caspases, activation of caspase-1 appears to precede that of caspase-3, favoring the necrotic/pyroptotic mechanism of killing (FIG. 8B). Interestingly, western blot analysis shows that caspase-1 is constitutively activated/cleaved in breast cancer cells (FIG. 1H). Our flow data based on fluorescently labeled caspase-1 substrate-specific probe, however, suggest the existence of another level of regulation of caspase-1 activity that can be further enhanced by Ivermectin. Overall, these findings indicate that Ivermectin kill cancer cells though a mechanism combining apoptosis and necrosis/pyroptosis.

Role of NADPH oxidases-generated ROS

Figure 9A:
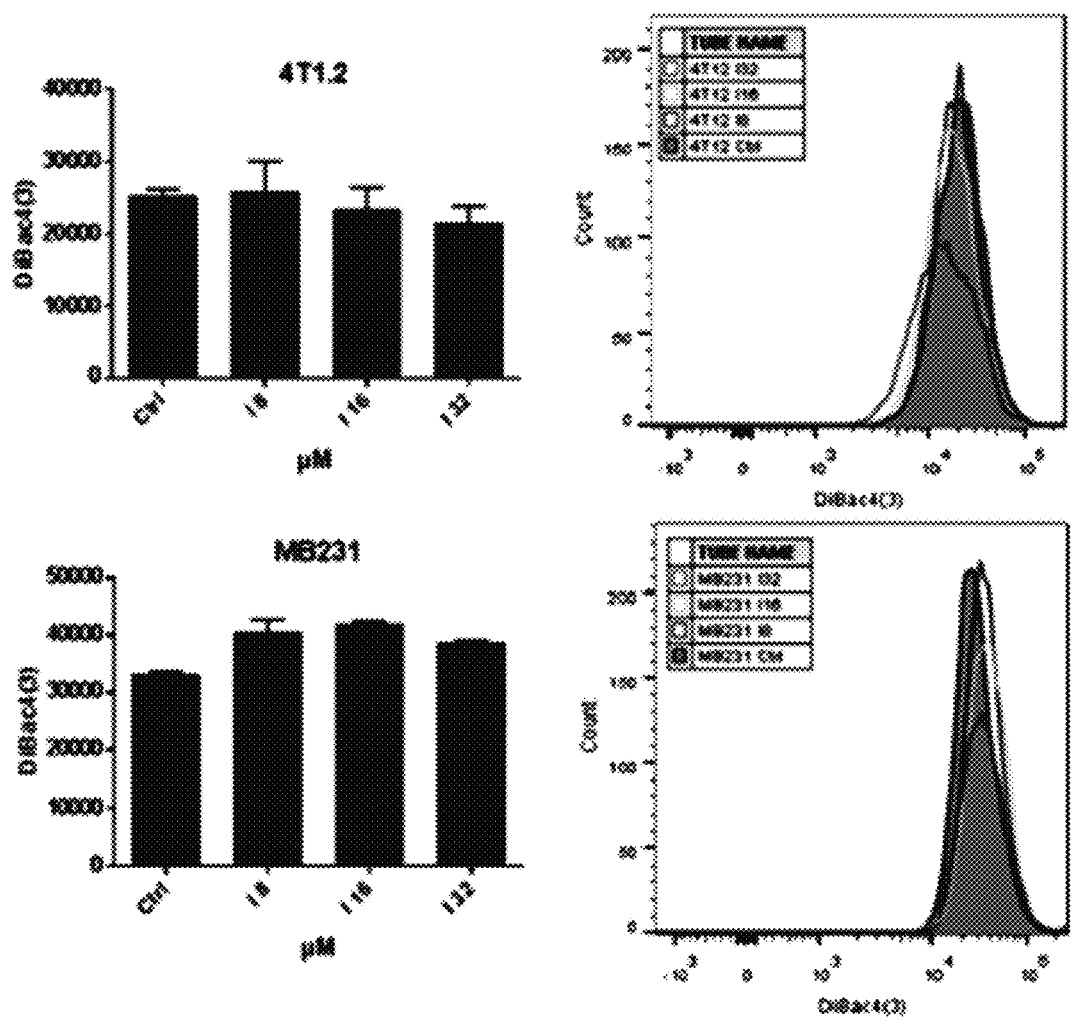
FIGS. 9A-9H. Role of NADPH oxidase-generated ROS.
Figure 9B:
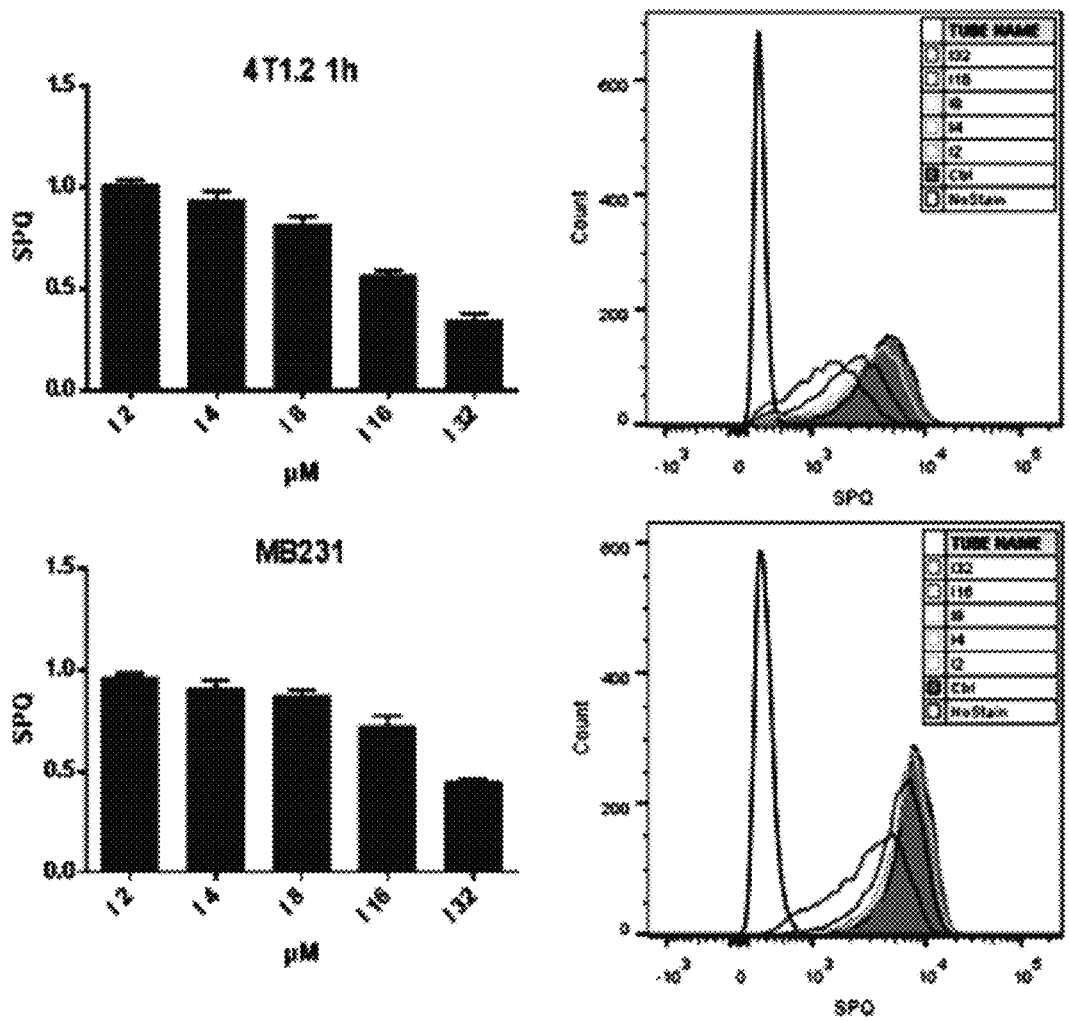
Figure 9C:
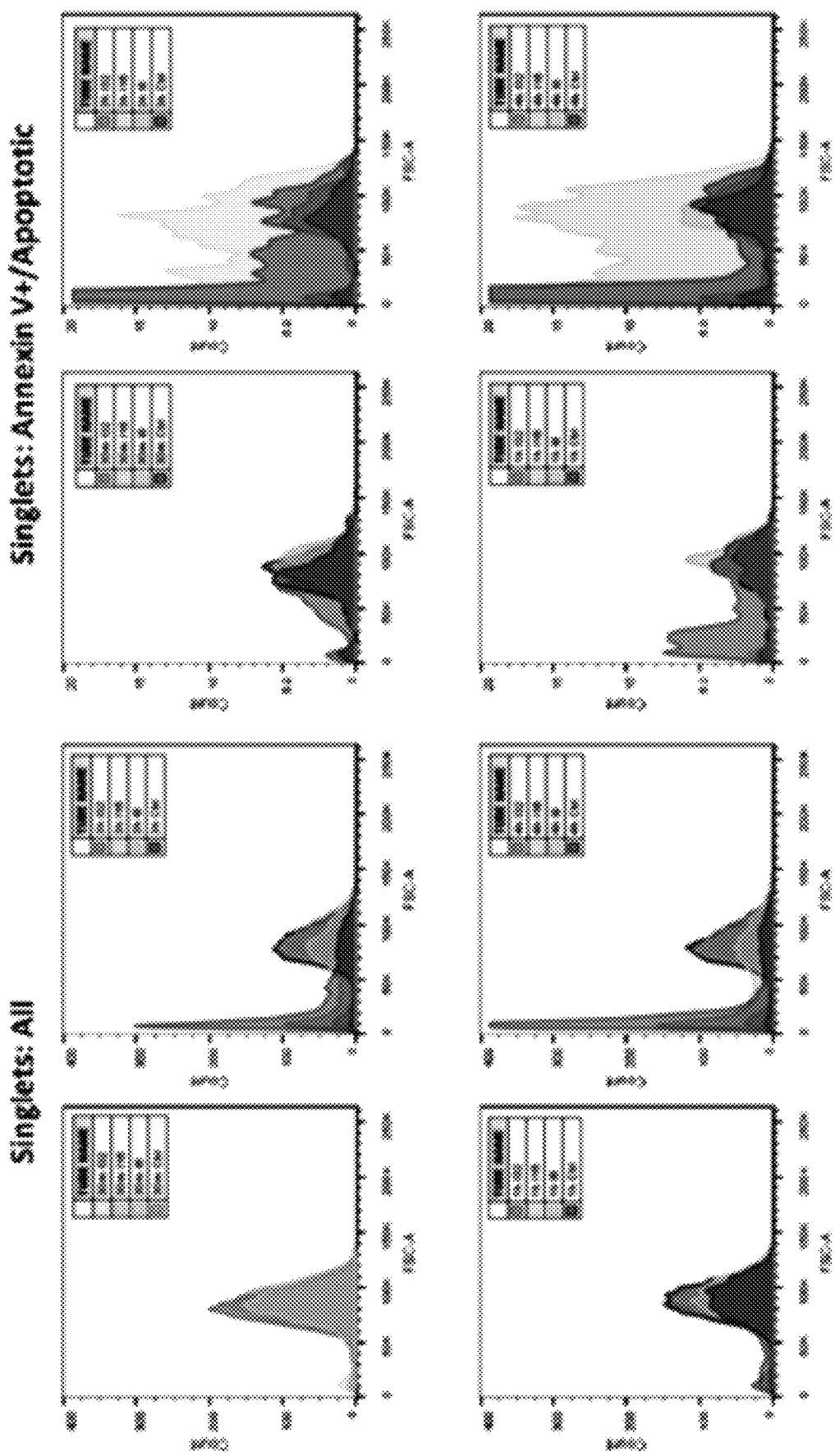
Figure 9D:
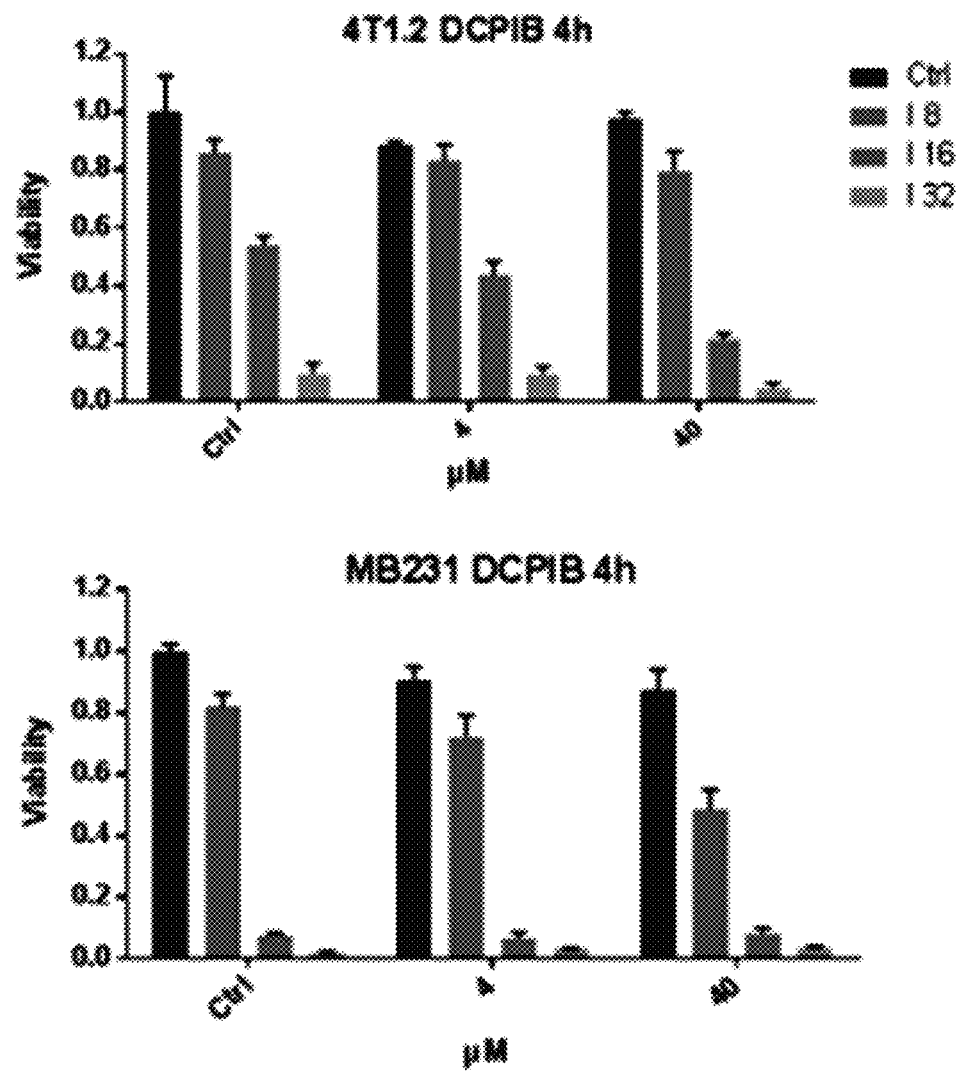

According to these results, treatment of mouse 4T1.2 breast cancer cells with Ivermectin resulted in plasma membrane hyper-polarization associated with Cl⁻ influx but modest cell swelling (FIGS. 9A-9C). Cell swelling appeared to be masked by rapid progression to necrotic cell death: the associated loss of membrane integrity and cytosolic content resulted in apparent cell shrinking. Analysis of both PS-positive apoptotic cells and cells surviving the initial killing suggest that death may be preceded by a brief swelling phase. Swelling appears unlikely to be the direct cause of cell death. Osmotic swelling initiates export of Cl⁻ from the cytosol. Specifically, outwardly rectifying I (swell) Cl⁻ channels can be activated by an NADPH oxidases-ROS-$H_2O_2$ mechanism in an ATP release- and P2X4-dependent manner[19-21]. Inhibition of these channels with DCPIB exacerbates Ivermectin killing, indicating that these defensive volume control mechanisms may be indirectly involved in cytotoxicity (FIG. 9D).

Figure 9E:
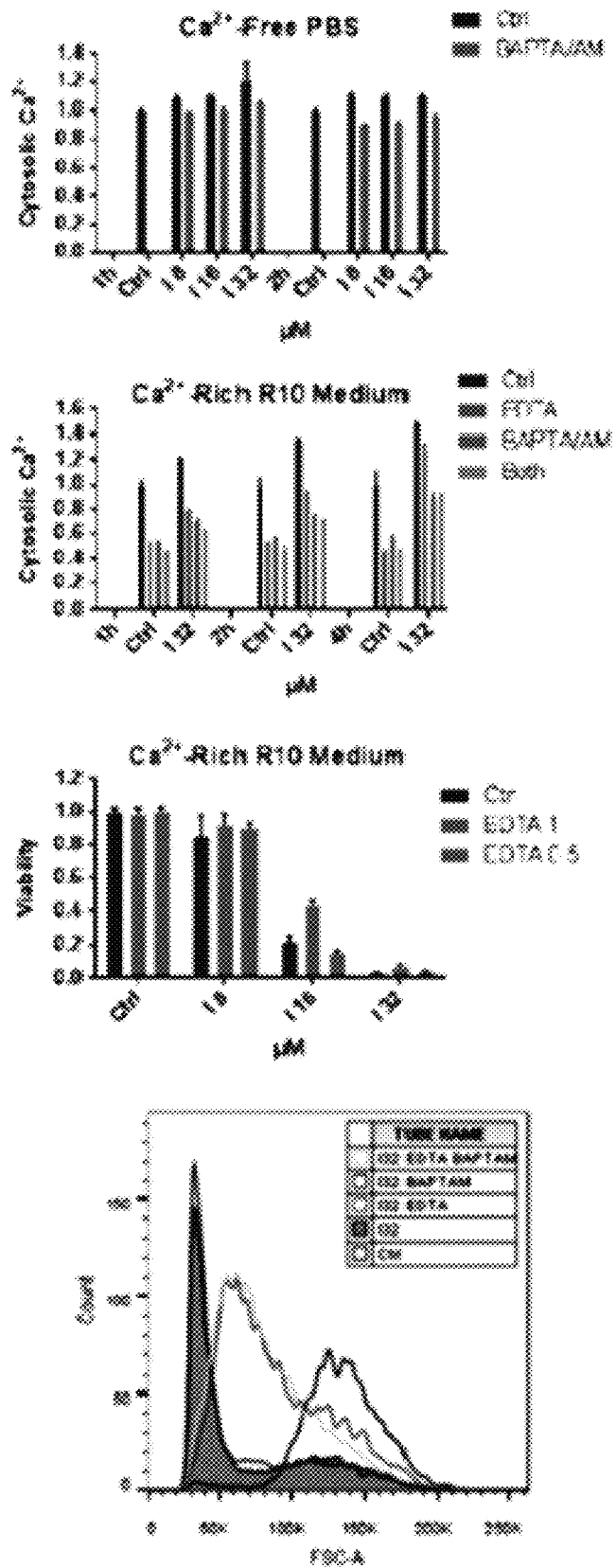
Figure 9F:
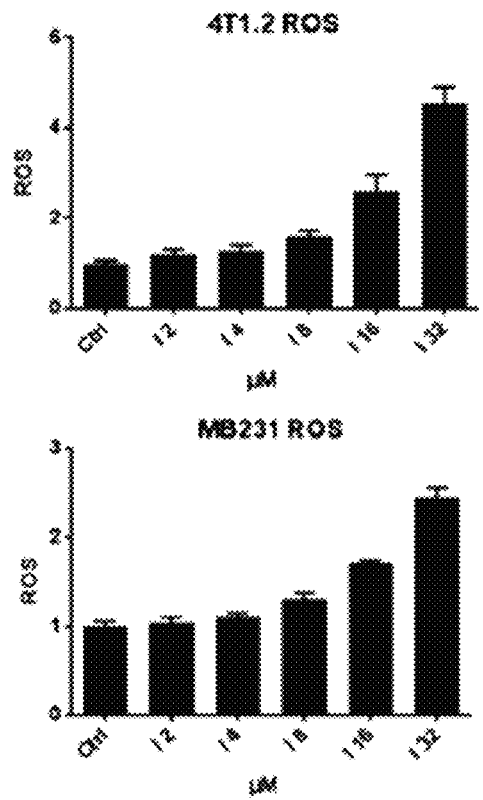
Figure 9G:
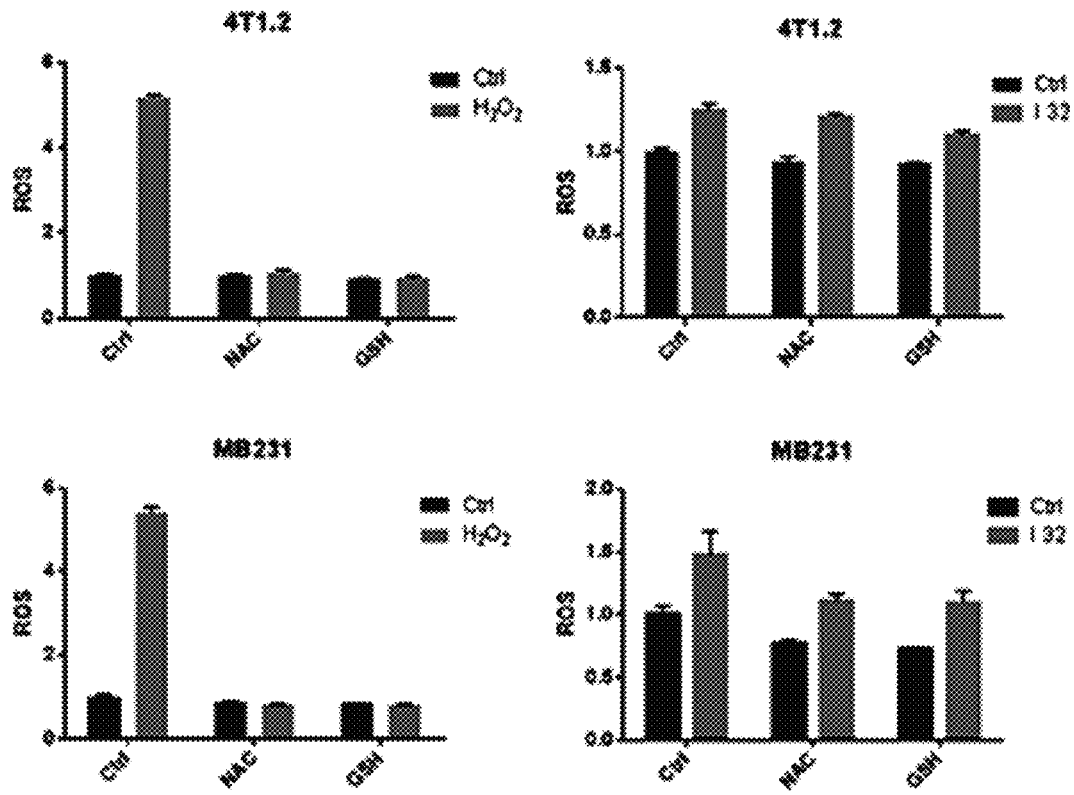
Figure 9H:
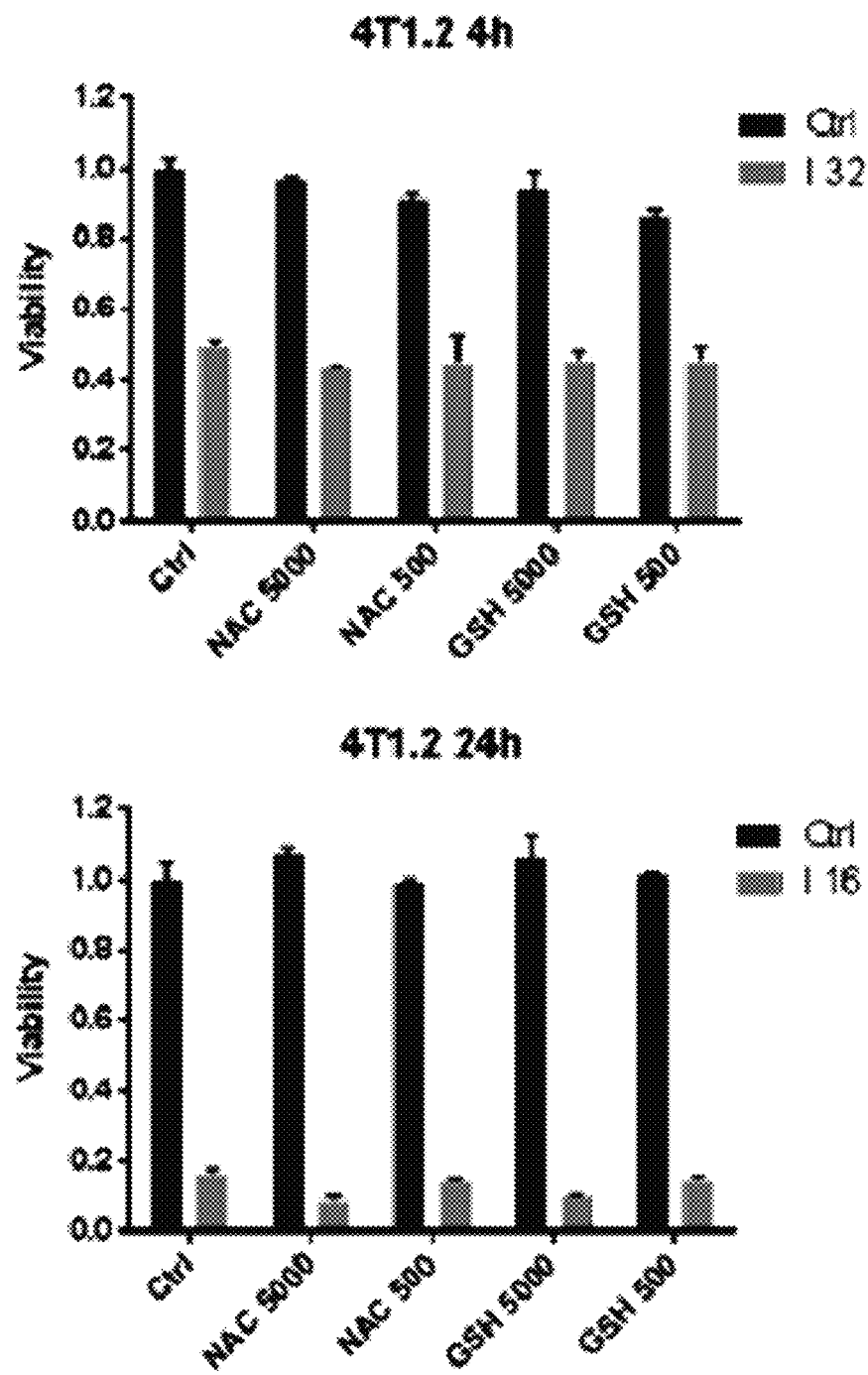

Maintenance of cell volume is regulated by ATP-, $Ca^{2+}$- and ROS-dependent mechanisms. Ivermectin induces sustained increases in cytosolic $Ca^{2+}$ that may originate from both extracellular and ER sources and cell death can be suppressed by chelating extracellular $Ca^{2+}$ with EDTA (FIG. 9E). In previous studies in leukemic cells, reactive oxygen species (ROS) were described as direct mediators of cytotoxicity. In contrast, our findings in breast cancer cells indicate that Ivermectin-induced ROS (FIG. 9F) are not the direct cause of cell death. The ROS scavengers, NAC and GSH, effectively blocked $H_2O_2$-generated ROS (FIG. 9G) but were less effective against Ivermectin-induced ROS and completely failed to prevent, or even delay, Ivermectin-induced killing (FIG. 9H).

Figure 2A:
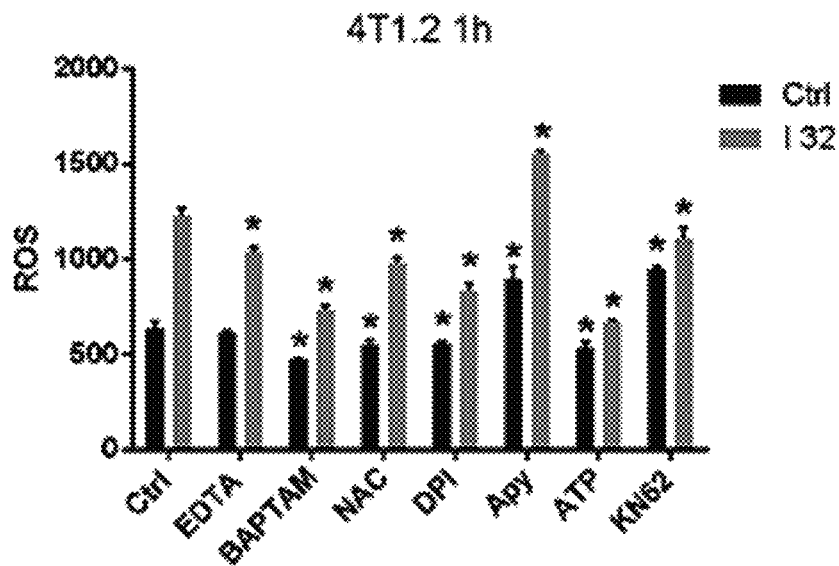
FIGS. 2A-2C. Role of NADPH oxidases-generated ROS.
Figure 2B:
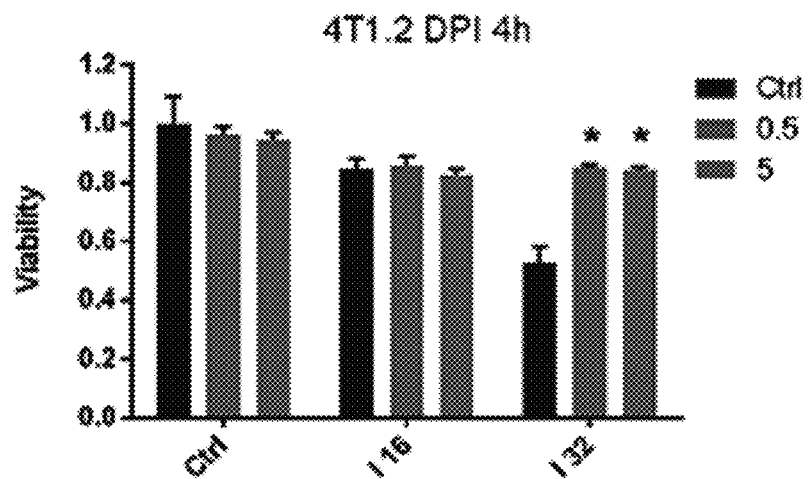
Figure 2B:
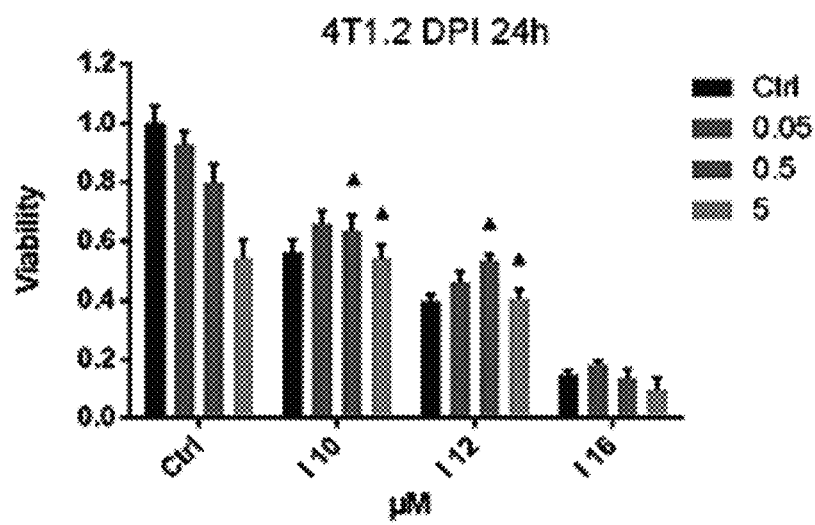

It is not solely the magnitude of Ivermectin-induced ROS that kills cancer cells. Unlike ROS of mitochondrial origin, NADPH oxidases-generated ROS are known to play important signaling roles and some NADPH oxidases are also $Ca^{2+}$-dependent. Applicants demonstrated that Ivermectin-induced ROS are regulated partially by $Ca^{2+}$, NADPH oxidases, ATP and P2X7 (FIG. 2A). Of note, an inhibitor of NADPH oxidases, Diphenyleneiodonium (DPI), is able to transiently block Ivermectin-induced killing (FIG. 2B). Short-term exposure to DPI and high doses of Ivermectin were found to be more informative since NADPH oxidases are essential for tumor cell growth and prolonged exposure to DPI exacerbates oxidative stress and becomes directly toxic. These data suggest that $Ca^{2+}$/NADPH/ROS signaling is directly involved in the mechanism of killing.

Figure 2C:
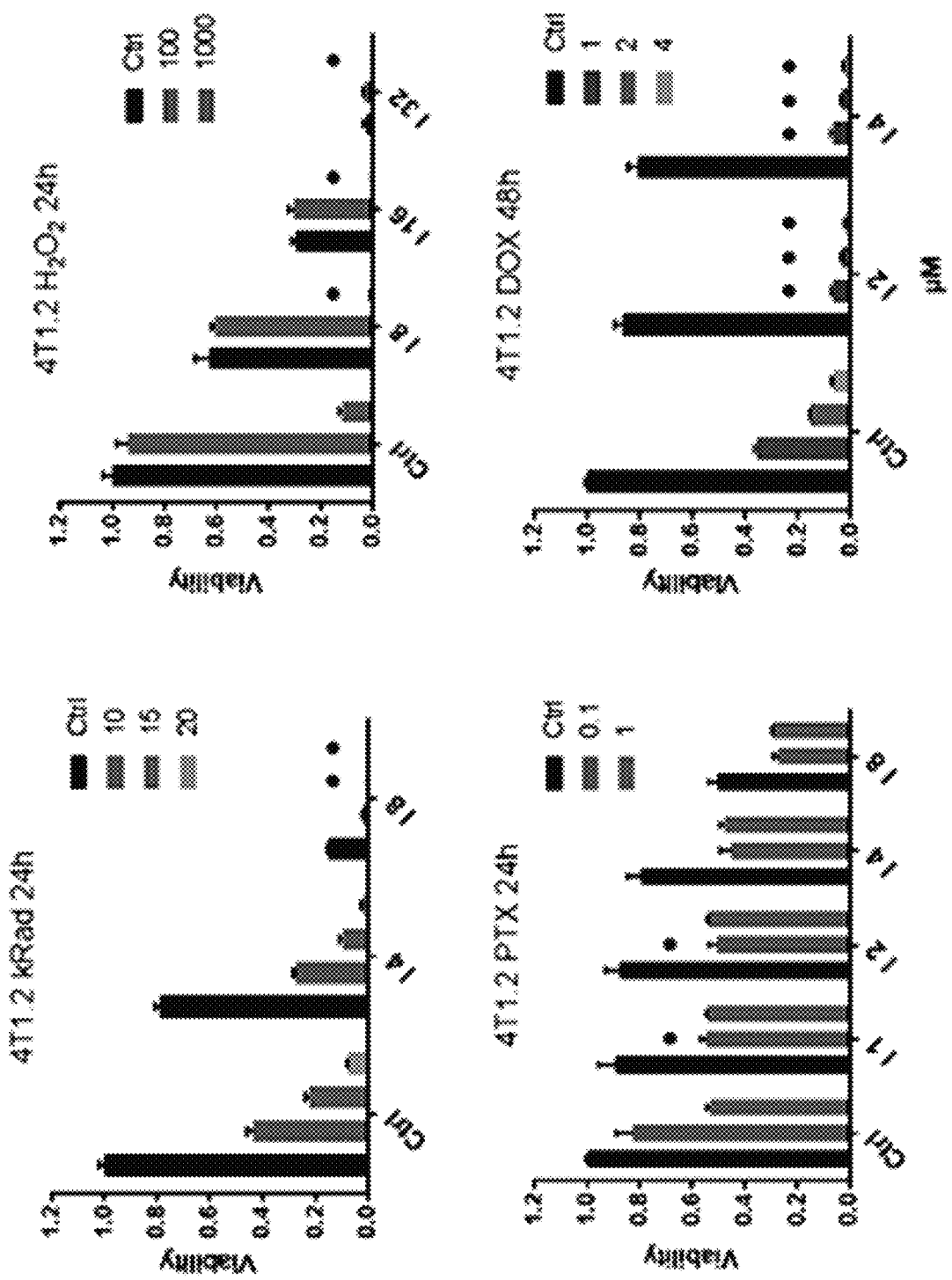

Ivermectin was found to be synergistic with irradiation, $H_2O_2$-generated ROS, and chemotherapeutic agents that are known inducers of ROS stress such as doxorubicin and paclitaxel (FIG. 2C, Table 1).

TABLE 1

Synergy between Ivermectin and ROS.

| | CompuSyn CI values: | | | | |
|---|---|---|---|---|---|
| | <0.8 Synergistic | 0.8-1.2 Additive | | >1.2 Antagonistic | |
| | 4 | 8 | | 8 | 16 |
| kRad 15 | .16 | .75 | $H_2O_2$ 100 | .46 | .39 |
| kRad 20 | .94 | .63 | $H_2O_2$ 1000 | .24 | .20 |
| | 1 | 2 | | 2 | 4 |
| PTX 0.1 | .35 | .52 | DOX 1 | .43 | .61 |
| PTX 1 | .30 | .51 | DOX 2 | .42 | .56 |

Although NADPH oxidases-generated ROS can contribute to ROS imbalance and ROS-mediated killing, the magnitude of Ivermectin-induced ROS does not appear to be directly cytotoxic. Therefore, we hypothesized that cell death is driven by ROS-dependent signaling pathways.

Dual Roles of ATP and Purinergic Signaling in Ivermectin's Killing

Figure 3A:
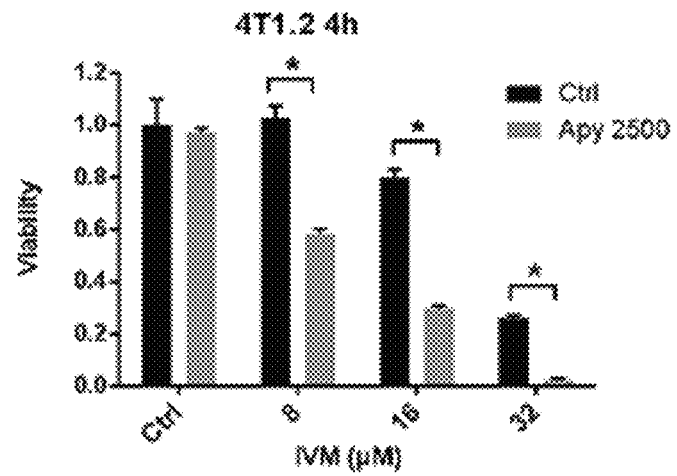
FIGS. 3A-3G. Dual roles of ATP and purinergic signaling in Ivermectin's killing.
Figure 3B:
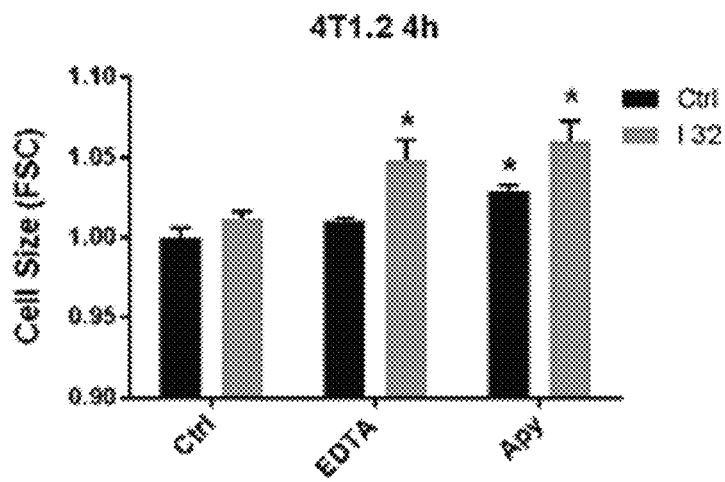
Figure 10A:
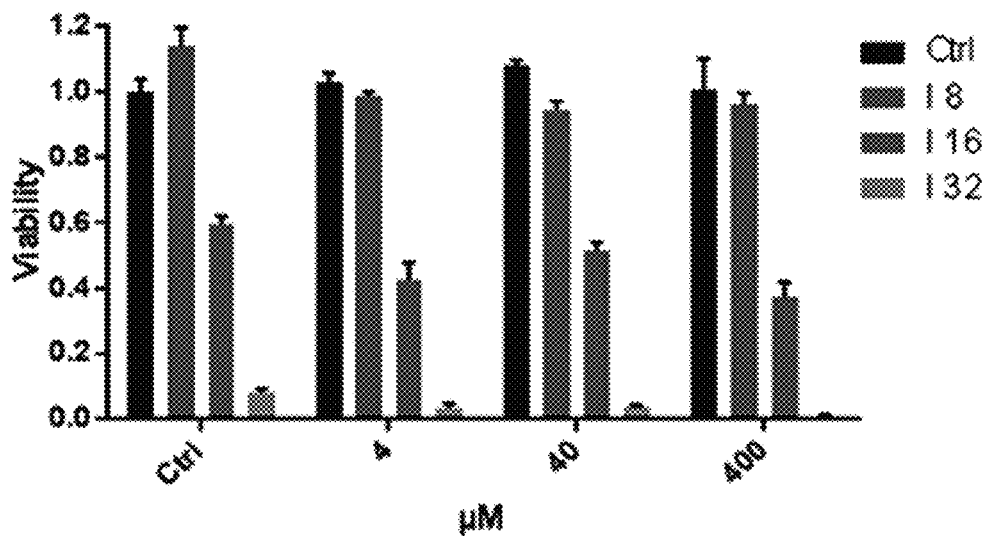
Figure 10B:
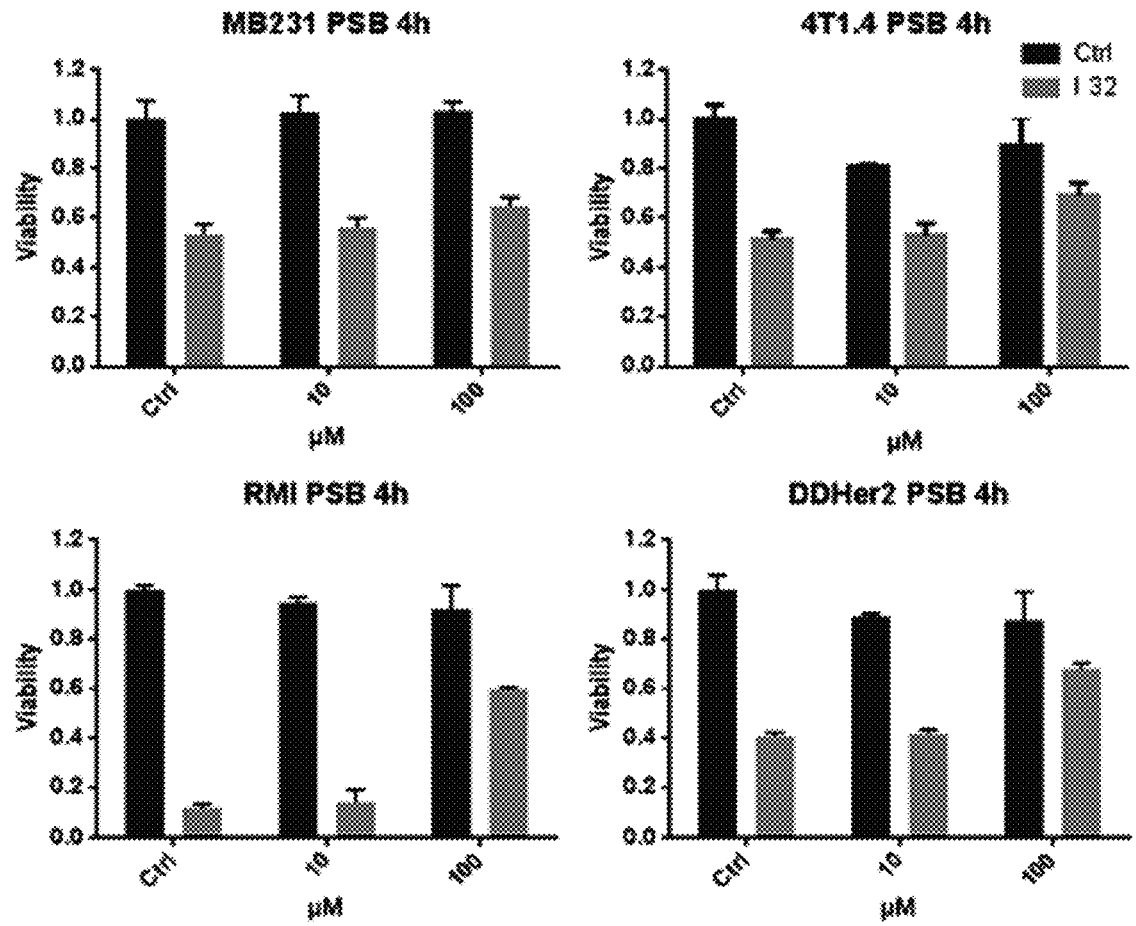

Ivermectin killing was initially enhanced by both depleting extracellular ATP with Apyrase (FIG. 3A) and blocking purinergic signaling with a non-specific inhibitor of P2 receptors (Suramin) (FIG. 10A). Ivermectin-induced cytotoxicity was suppressed in multiple cancer cell lines by blocking extracellular ATPases (CD39 and CD73) with PSB 069 (FIG. 10B). This confirms an initial protective role of extracellular ATP and implicates ATP and ATP-dependent $Ca^{2+}$/ROS signaling in the early defense mechanisms that contain Ivermectin-induced killing. It was found that extracellular $Ca^{2+}$ and ATP prevent Ivermectin-induced cell swelling, thus providing a mechanistic explanation for their initial protective role (FIG. 3B).

Figure 3C:
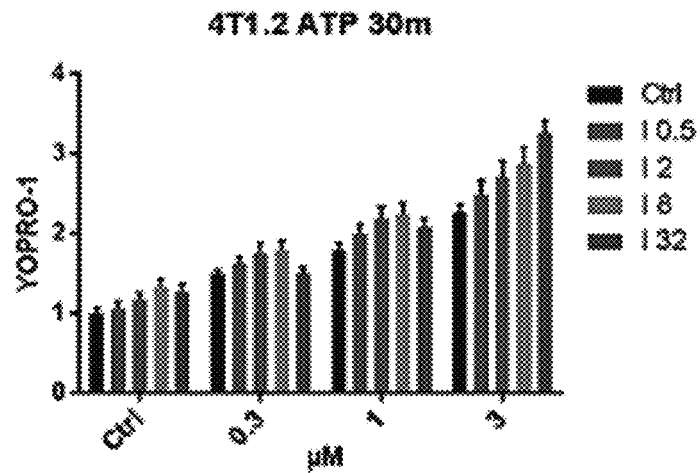
Figure 10C:
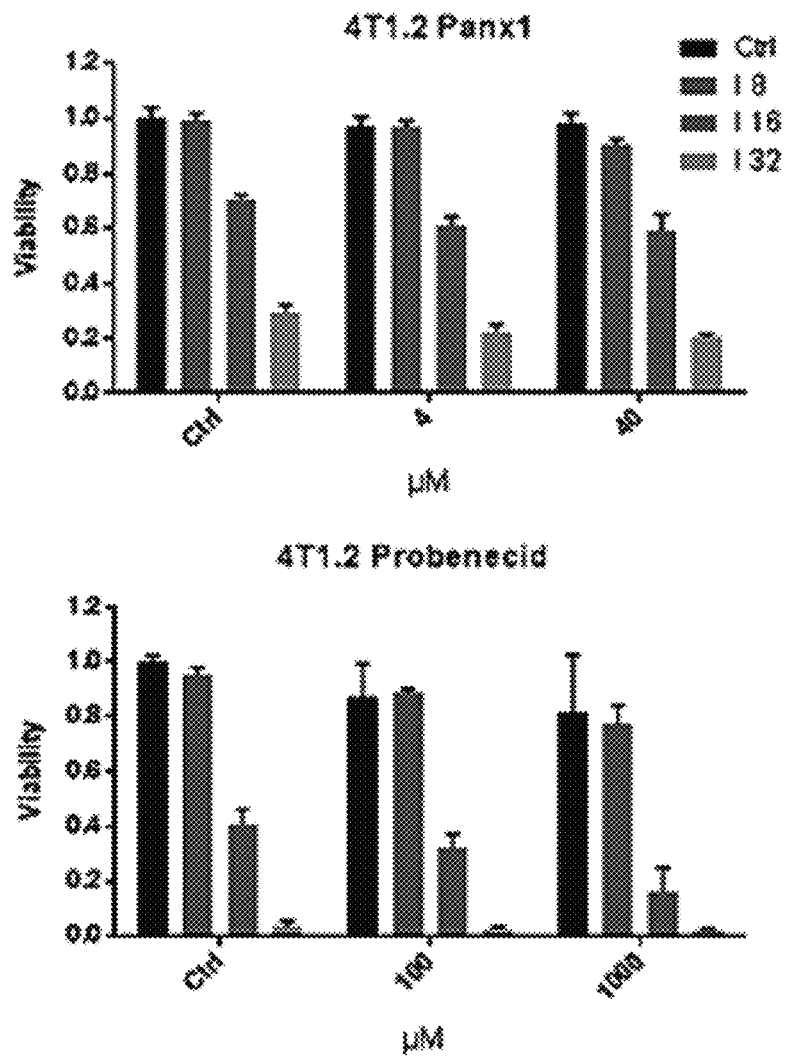

The protective effect of the ATP/$Ca^{2+}$/ROS-pathway is, however, only transient: extended exposure to either high concentrations of ATP or sustained elevation of cytosolic $Ca^{2+}$ is cytotoxic to both mouse and human cancer cells. We decided to investigate whether the sustained increase in cytosolic $Ca^{2+}$ levels described earlier was preceded by extracellular ATP release from non-necrotic viable cells. ATP release from the P2X4/P2X7-gated Pannexin-1 channels is a potent feed-forward mechanism operating in autophagic cancer cells and activated leukocytes. Ivermectin synergized with ATP in opening P2X4/P2X7/Pannexin-1 channels resulting in partial permeabilization of the plasma membrane of 4T1.2 cells to YOPRO-1 without compromising cell viability (FIG. 3C). Blocking Pannexin-1 channels with either a Panx-1 mimetic peptide or Probenecid enhanced Ivermectin cytotoxicity validating the initial protective role of ATP release (FIG. 10C).

Figure 3D:
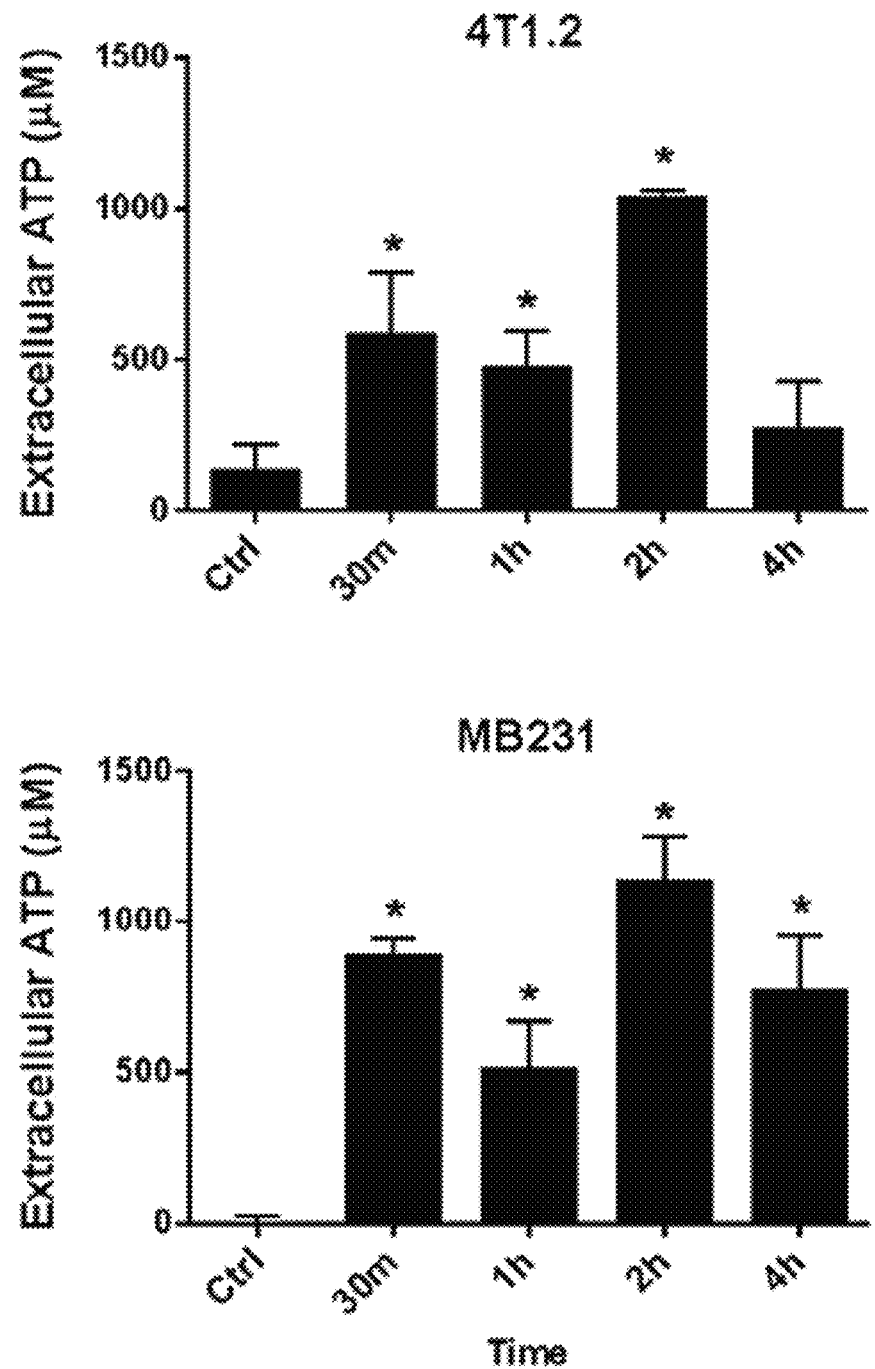
Figure 3E:
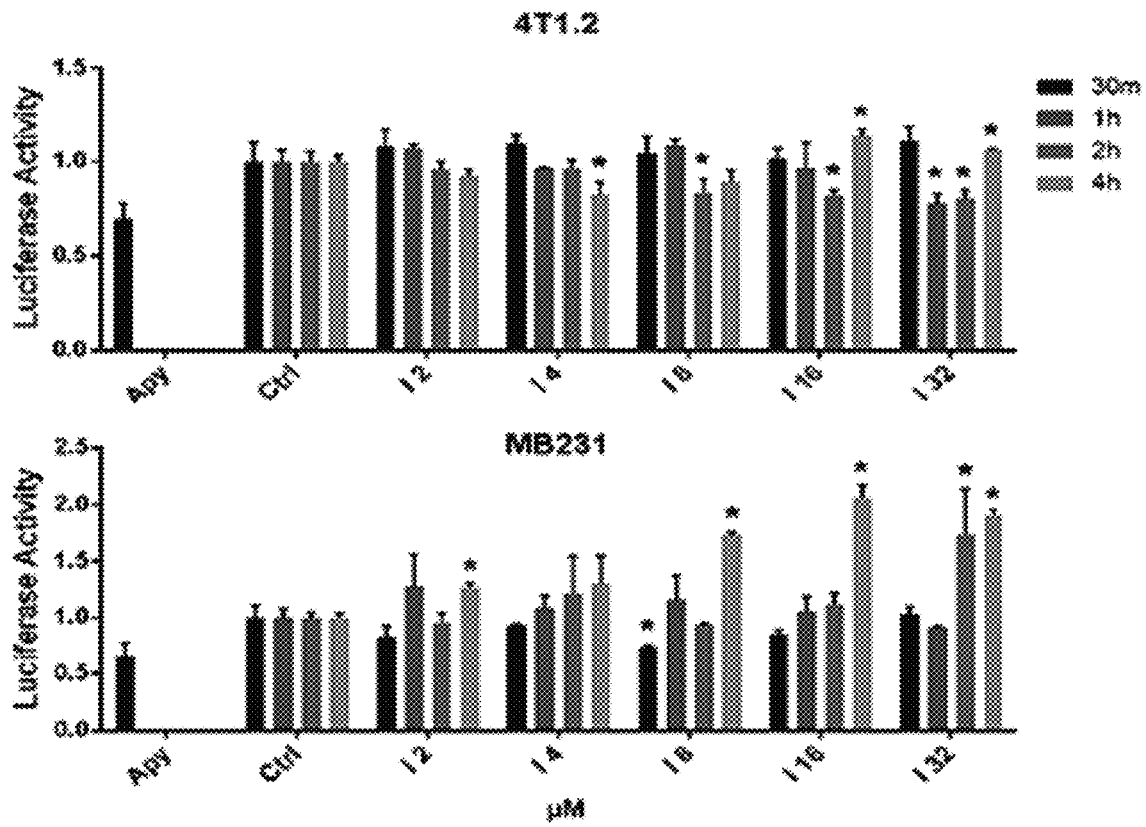
Figure 10D:
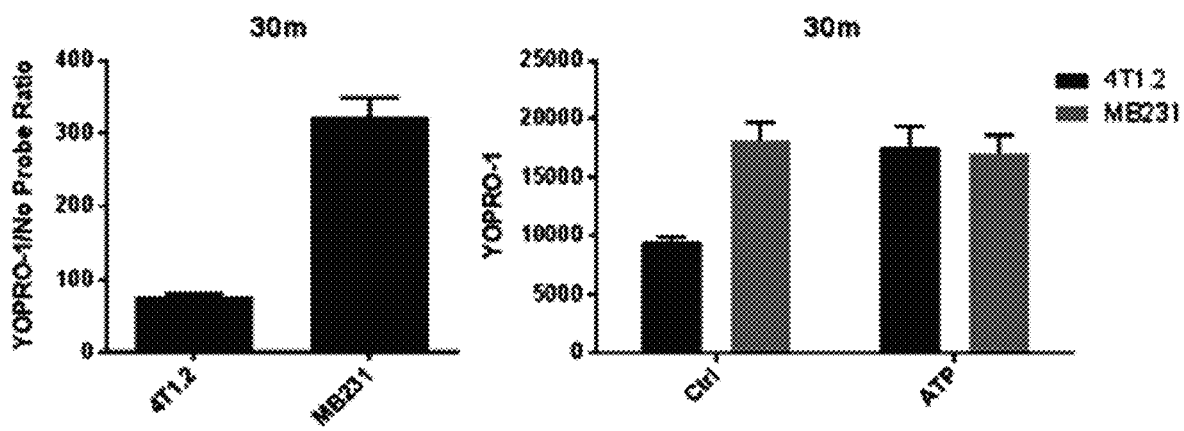
Figure 10E:
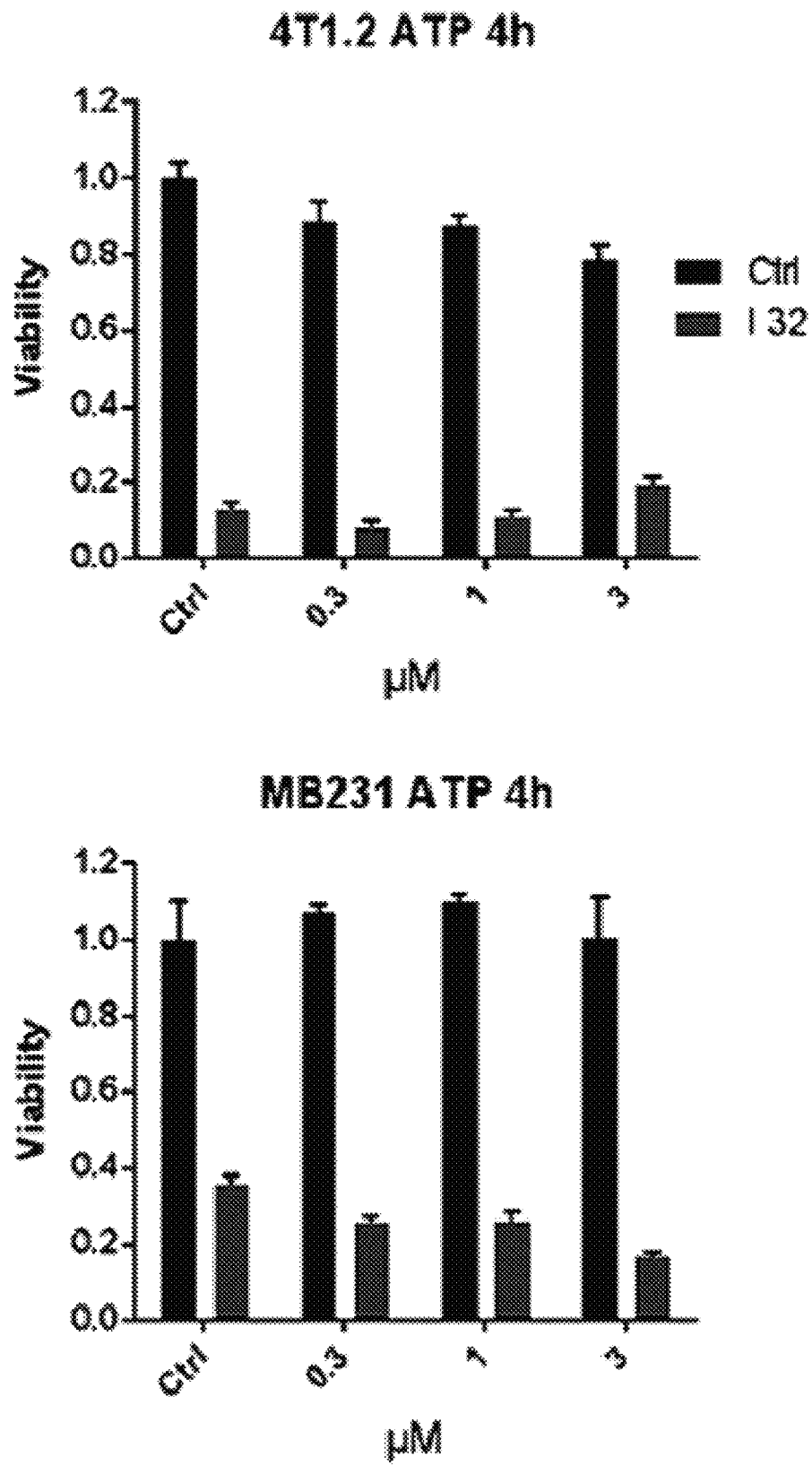

Analysis of supernatants from TNBC cells demonstrated an immediate increase in extracellular ATP levels in response to Ivermectin, followed by a period of its transient depletion (FIG. 3D). Using cells engineered to express a membrane-bound form of Luciferase, similar results were obtained by measuring plasma membrane-proximal extracellular ATP levels (FIG. 3E). These findings suggest that ATP release is necessary to balance an increased demand/consumption of extracellular ATP. Following the transient decline during the protective phase, ATP levels are restored and continue to rise. This is consistent with a possible switch to a cytotoxic role for ATP during Ivermectin-mediated killing (FIGS. 10D-10E).

Figure 3F:
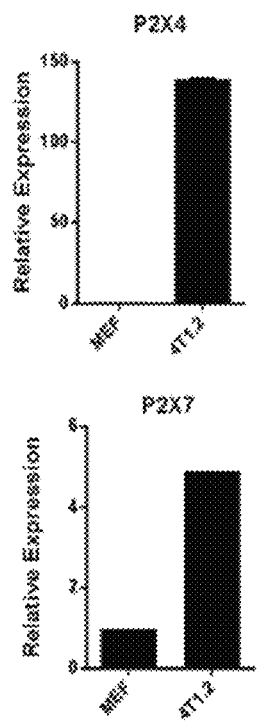
Figure 3G:
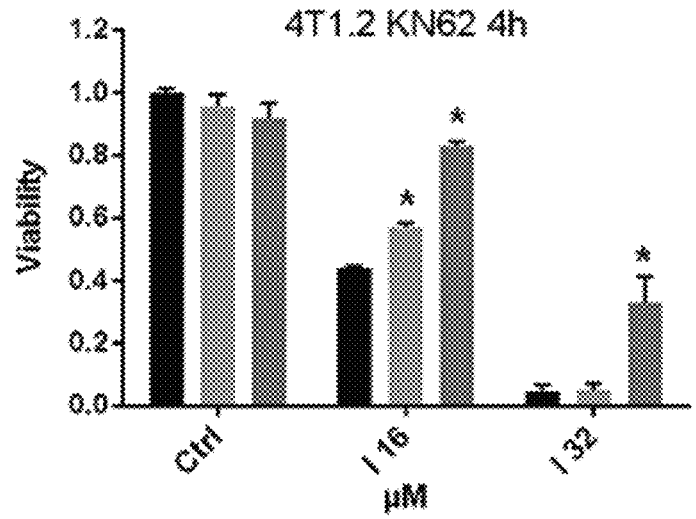
Figure 3G:
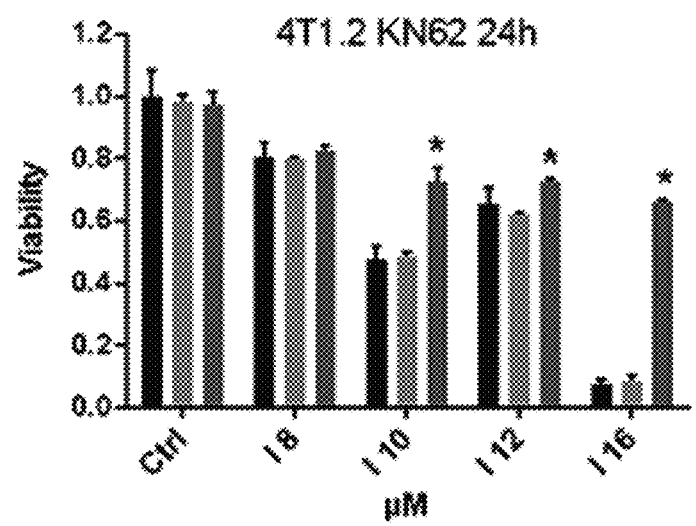
Figure 3G:
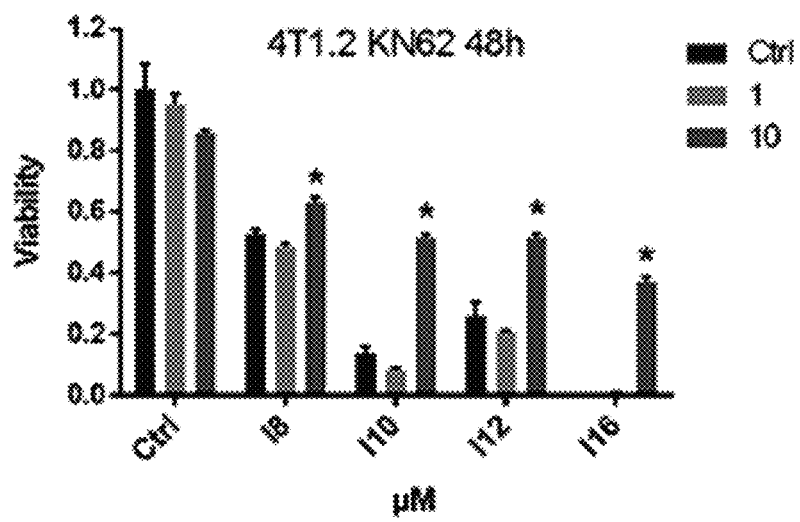
Figure 10F:
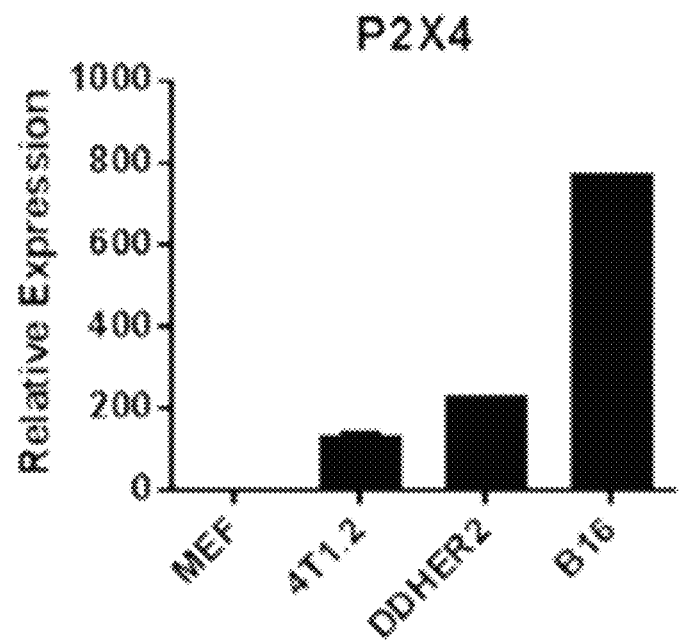
Figure 10F:
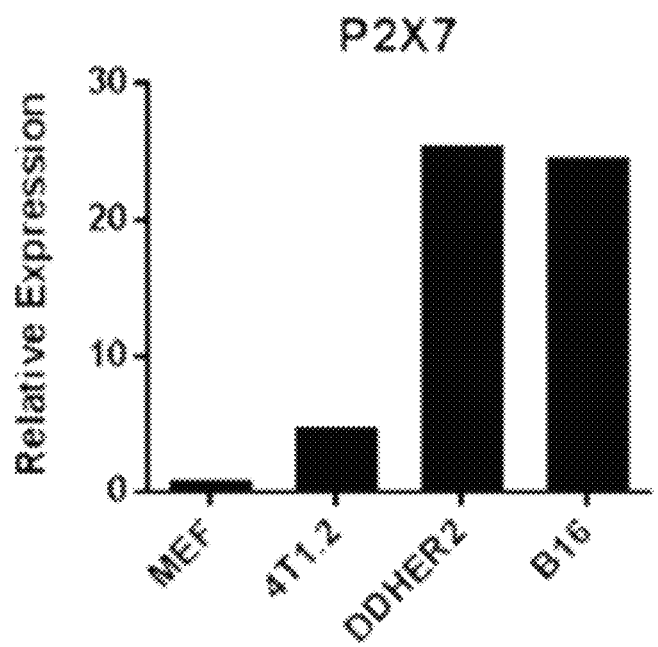
Figure 10H:
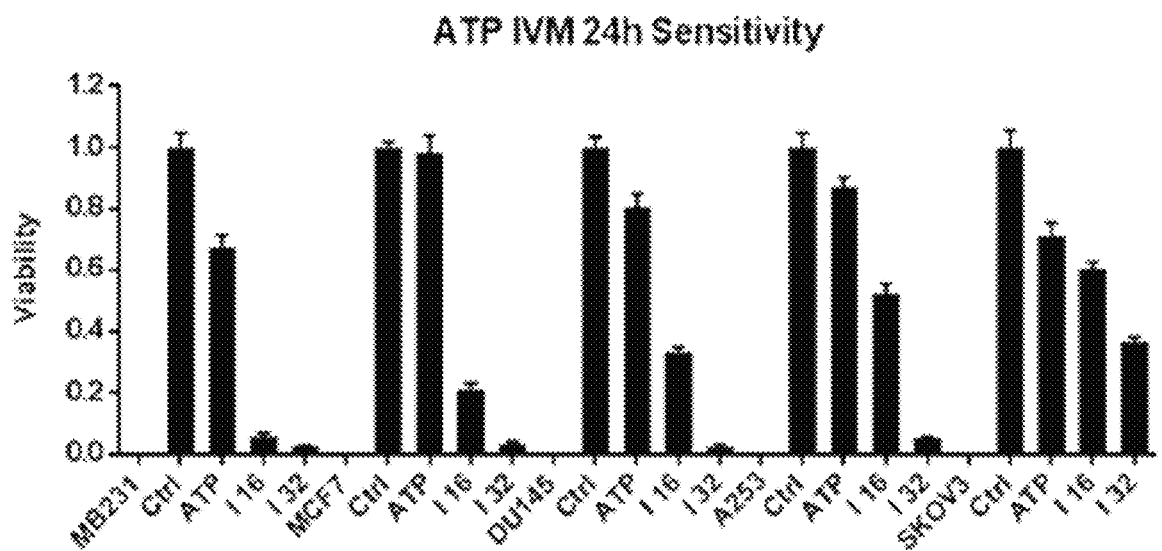
Figure 10I:
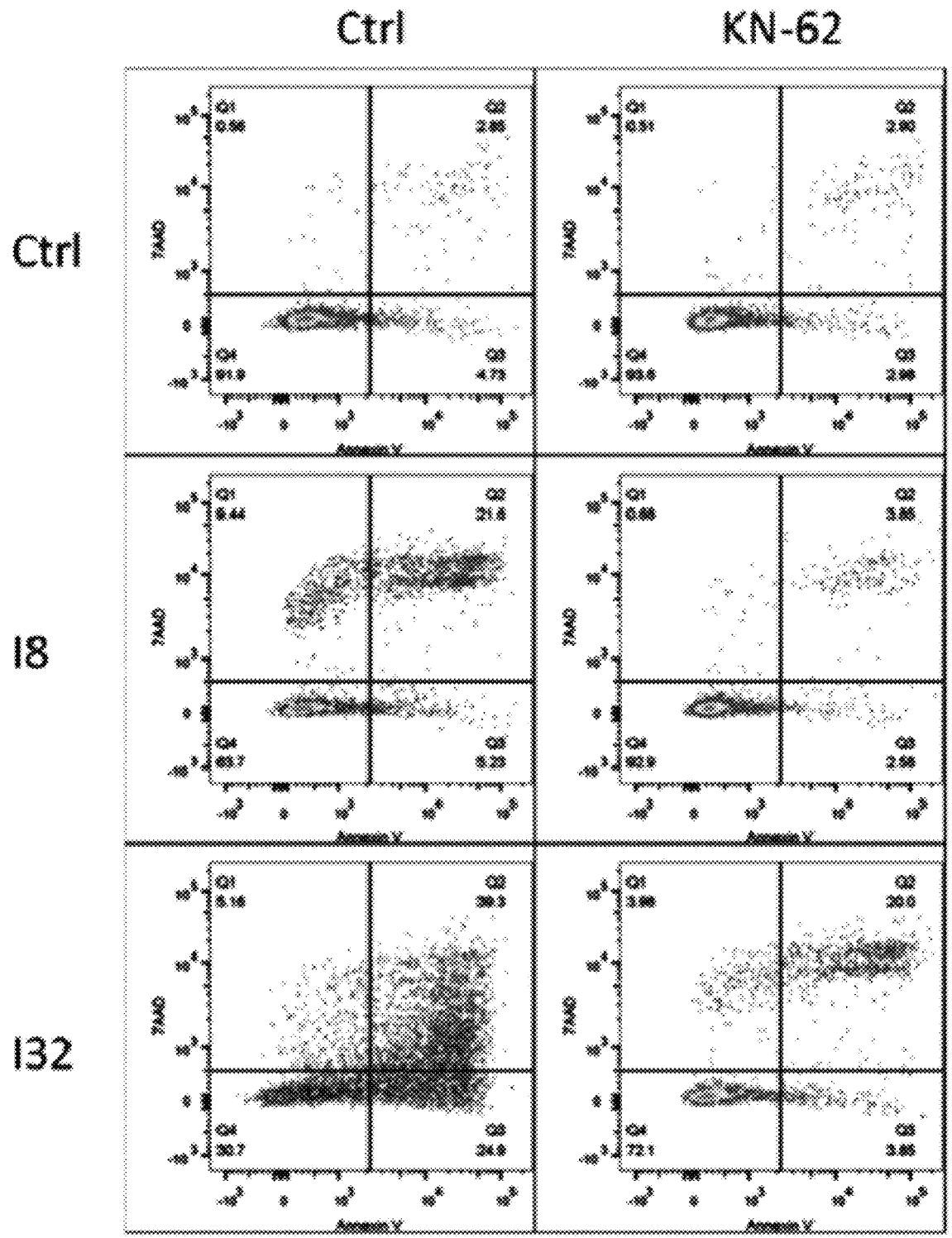

Ivermectin can enhance signaling of the P2X4 receptor, which can complex with both pannexin-1 and death-mediating P2X7 receptors [27, 28]. Applicants demonstrated up-regulation of P2X7 and Ivermectin-sensitive P2X4 receptors in 4T1.2 cells (FIG. 3F) as well as in other murine cancer cell lines (FIG. 10F). We also validated over-expression of the P2X4 and P2X7 receptors as a characteristic feature of human breast cancer lines (FIG. 10G). The sensitivity of different human cancer cell lines to Ivermectin was found to correlate with their sensitivity to ATP (FIG. 10H). The semi-specific P2X7 inhibitor KN-62 was effective at blocking Ivermectin-induced necrotic and apoptotic cell death (FIG. 3G and FIG. 10I).

Figure 10J:
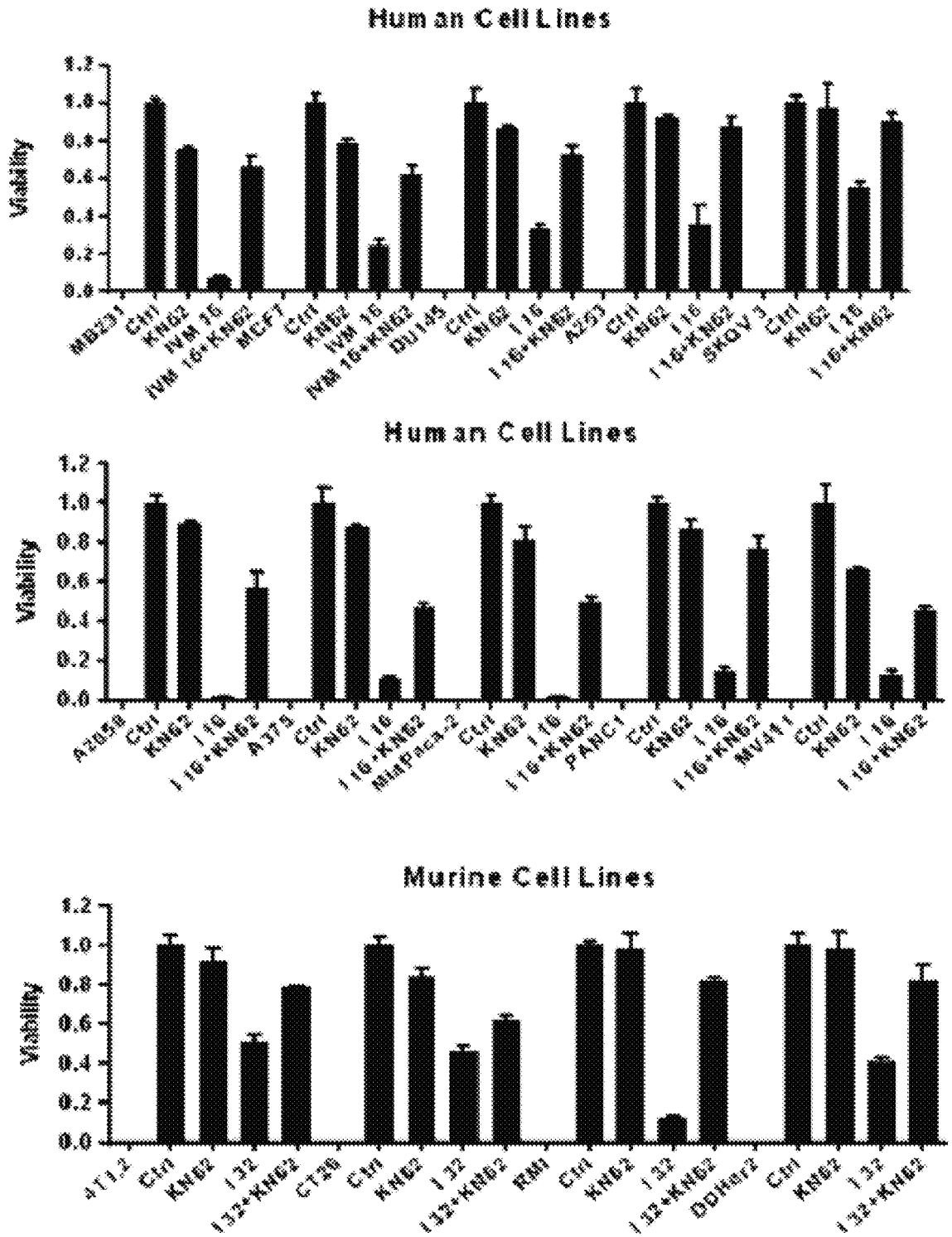
Figure 10K:
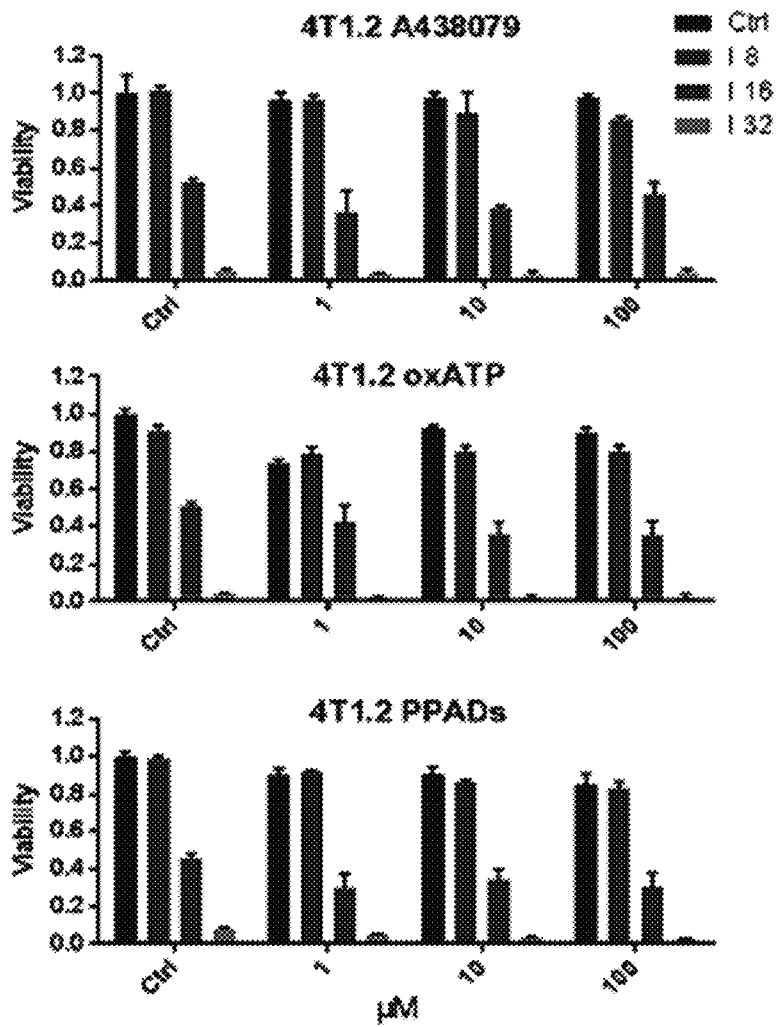
Figure 10L:
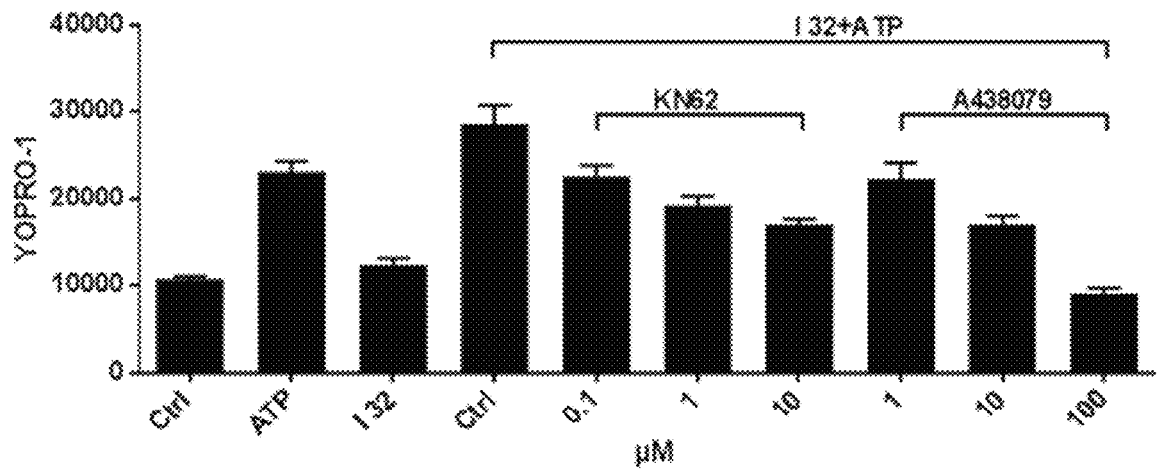

Ivermectin induced a P2X7-dependent death pathway in a broad spectrum of murine and human cancer cell types (FIG. 10J). We did not observe any protection using other P2X7 receptor-specific inhibitors such as PPADs, OxATP, and A438079 (FIG. 10K). The ATP-gated P2X7 receptors possess three independent activities: 1) opening of intrinsic $Ca^{2+}$ channels; 2) modulation of Pannexin-1 channel activity and 3) activation of a cell death pathway. These appear to be mediated by different parts of the molecule and may be modulated by different inhibitors. To test whether the P2X7-specific inhibitors are in fact affecting P2X7-dependent mechanisms (rather than working through off-target effects), we evaluated their ability to block membrane permeabilization. Both KN-62 and A4308079 suppressed permeabilization to YOPRO-1 in a dose-dependent fashion (FIG. 10L). Moreover, the doses of KN-62 required to effectively block the pannexin-1 channel were consistent with doses required to protect against Ivermectin-induced killing.

Excessive CaMKII Signaling and MPTP Contribute to Cell Death

Figure 4A:
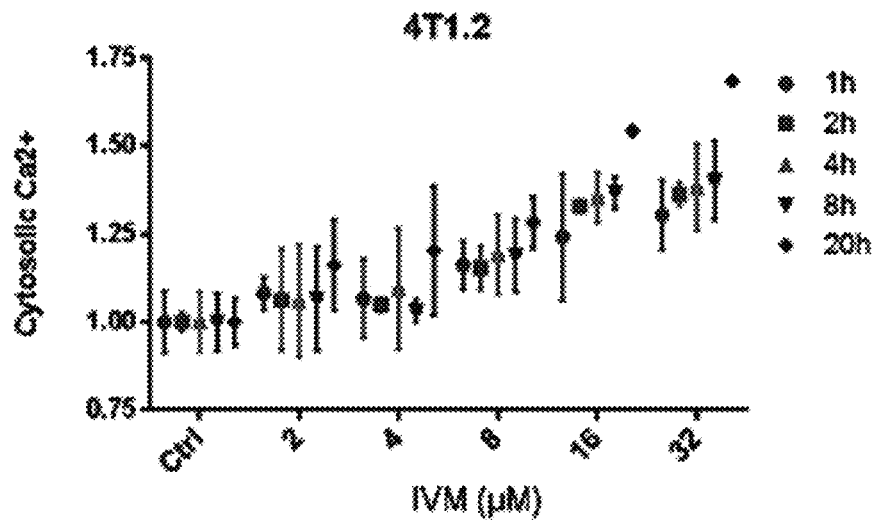
FIGS. 4A-4D. Excessive $Ca^{2+}$/CaMKII signaling and MPTP contribute to cell death.
Figure 4B:
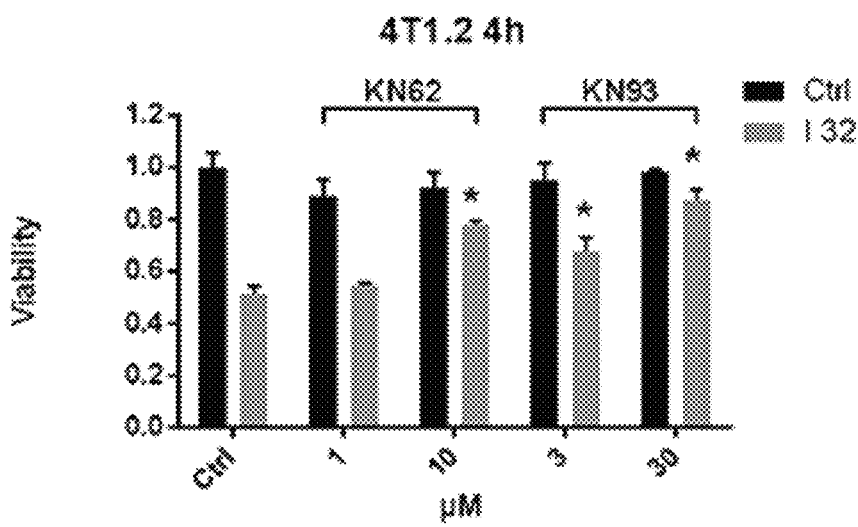
Figure 4C:
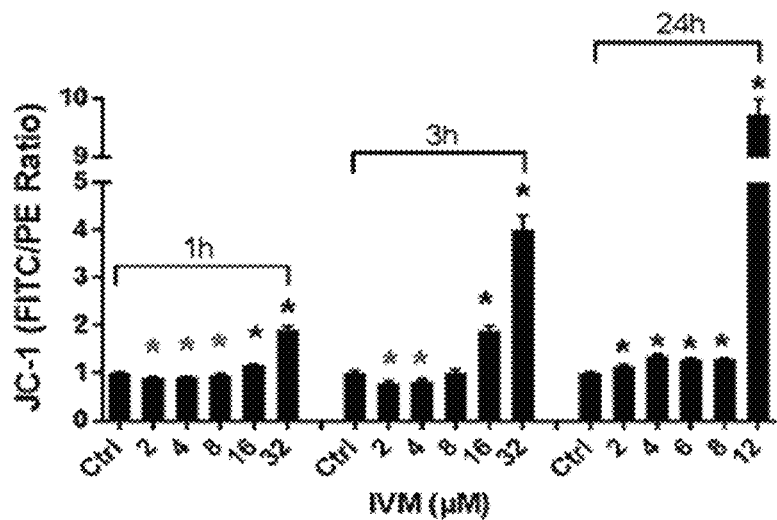
Figure 4D:
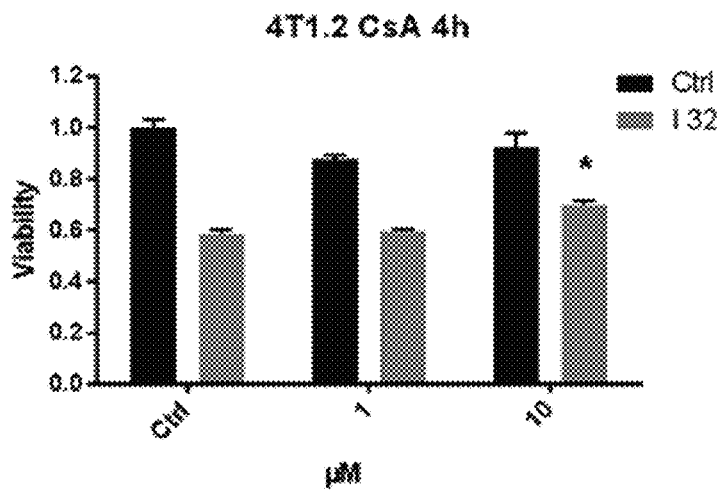
Figure 11A:
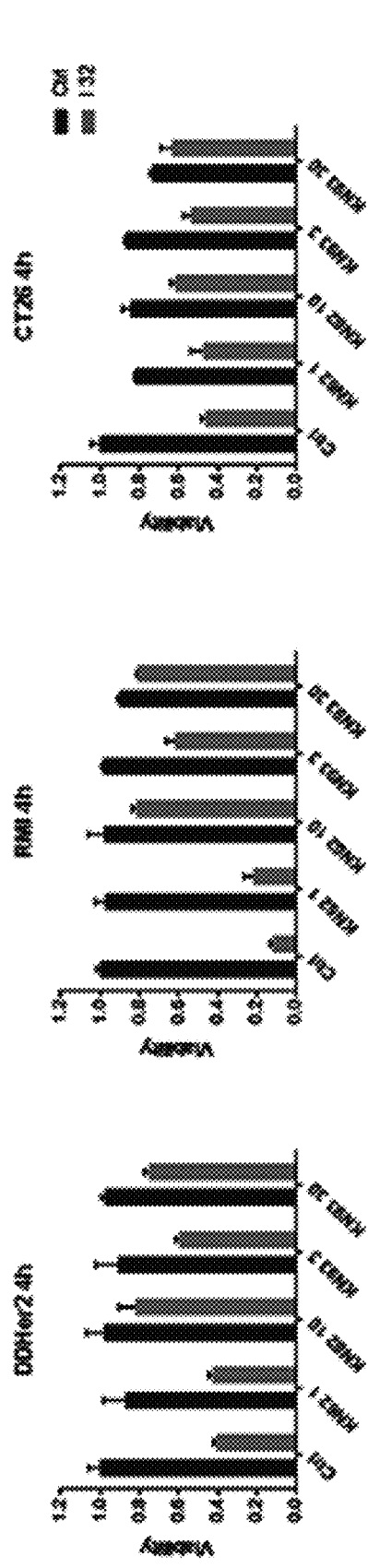
FIGS. 11A-11B. Excessive $Ca^{2+}$/CaMKII signaling and MPTP contribute to cell death.
Figure 11B:
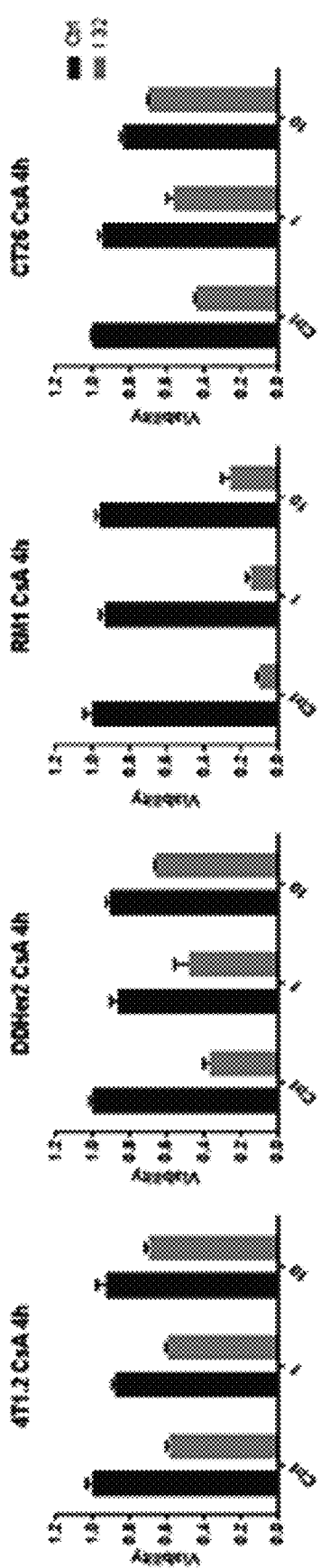

KN-62 is not completely specific for the P2X7 receptor and also weakly inhibits $Ca^{2+}$/Calmodulin-dependent protein kinase II (CaMKII). More than 1 μM of KN-62 is needed to protect against Ivermectin-induced cell death; and this value is consistent with KN-62's inhibition of CAMKII. CaMKII activity correlates with sustained increase in cytosolic $Ca^{2+}$ (FIG. 4A) and is known to be a downstream target of P2X7 receptor signaling and to mediate neuronal cytotoxicity in the context of FR, stroke and neurodegenerative diseases, pathologic conditions where ATP-mediated excitotoxicity is known to play a prominent role. We investigated whether Ivermectin-induced cell death was mediated by P2X7, CaMKII, or a combination of both. To this end, we used a CaMKII-specific inhibitor (KN-93) while knocking down the P2X7 receptor with shRNA. KN-93 effectively blocked Ivermectin-induced cell death, confirming that over-activation of the CaMKII underlies the initial wave of cell death in many Ivermectin-sensitive cancer cell lines (FIG. 4B and FIG. 11A). We also demonstrated that while lower doses of Ivermectin cause mitochondrial hyperpolarization, massive cancer cell death occurs in the context of a sudden depolarization of mitochondria (FIG. 4C) and that blockade of mitochondrial permeability transition pore (MPTP), the downstream effector of this cell death pathway, is able to confer partial protection against Ivermectin (FIG. 4D, and FIG. 11B).

CaMKII-Independent P2X7-Mediated Killing

Figure 5A:
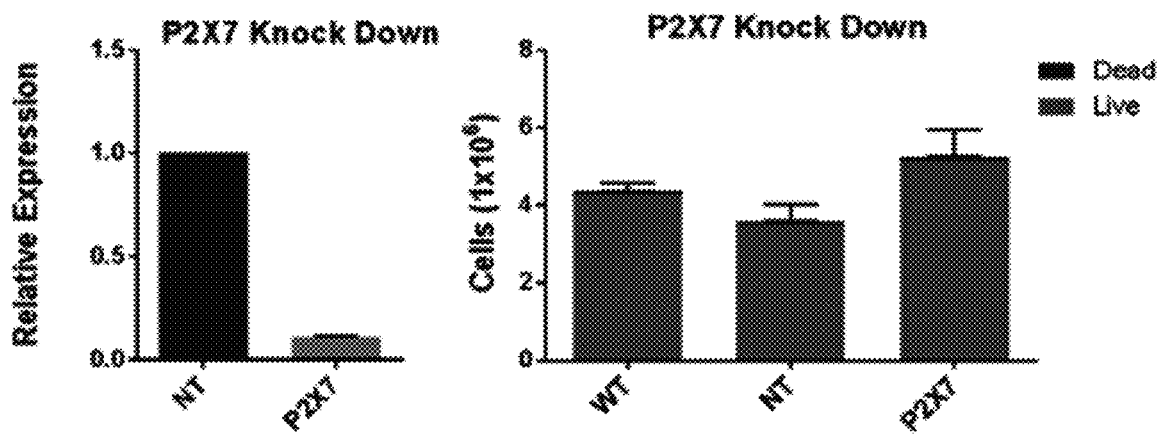
FIGS. 5A-5E. CaMKII-independent P2X7-mediated killing.
Figure 5B:
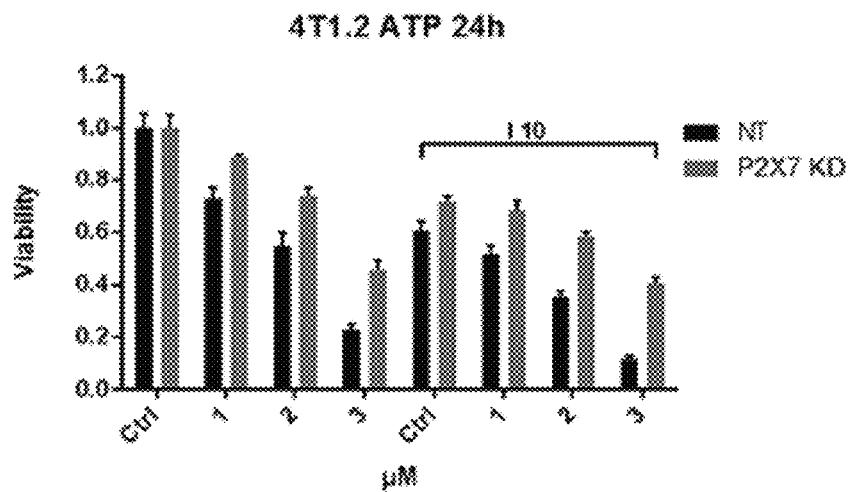

Given the low affinity of P2X7 for ATP, high extracellular ATP concentrations are needed for P2X7 receptors to deliver death signals. As extracellular ATP is transiently depleted and protective during Ivermectin-induced cell death, we sought to clarify the way in which the P2X7 pathway is activated and involved in cytotoxicity. To this end, we compared the ability of Ivermectin to kill wild type and P2X7-knockdown 4T1.2 cells (FIG. 5A). Overall, P2X7 knockdown cells were more resistant to ATP and ATP/Ivermectin cytotoxicity (FIG. 5B and Table 2), which is consistent with a pivotal role for the P2X7 receptor in ATP-mediated cytotoxicity.

TABLE 2

Effect of P2X7 knockdown on the synergy between Ivermectin and ATP.

| | CI values: | | |
|---|---|---|---|
| | <0.8 Synerg I 6 | 0.8-1.2 Addit I 8 | >1.2 Antag I 10 |
| | 4T1.2 shRNA (P2X7) | | |
| ATP 1 | 1.49 | 1.39 | 1.35 |
| ATP 2 | 1.18 | 1.03 | 1.11 |
| ATP 3 | 0.96 | 0.91 | 0.86 |
| | 4T1.2 shRNA (NT) | | |
| ATP 1 | 1.18 | 1.01 | 1.24 |
| ATP 2 | 1.17 | 1.01 | 1.10 |
| ATP 3 | 0.67 | 0.64 | 0.63 |

Figure 5C:
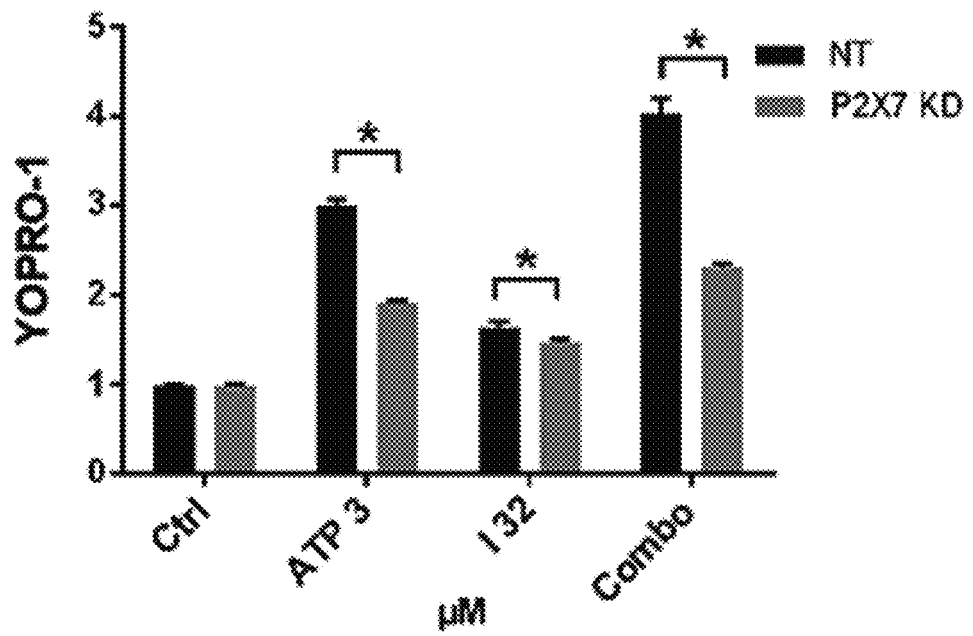

In addition, the P2X7 knockdowns were more resistant to ATP- and ATP/Ivermectin-induced membrane permeabilization to YOPRO-1 (FIG. 5C), suggesting that over-activation of this protective mechanism might lead to cytotoxicity. High concentrations of extracellular ATP kill cancer cells in a P2X7-dependent fashion but with much slower kinetics compared to Ivermectin. Therefore, in addition to targeting ATP/P2X4/P2X7 signaling, the drug likely affects other pathways.

Figure 5D:
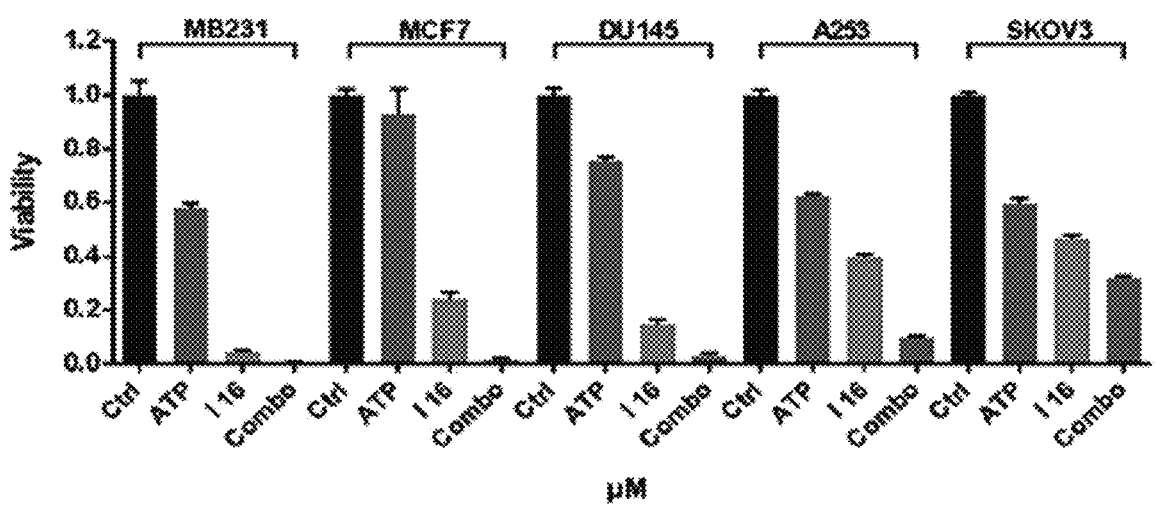
Figure 5E:
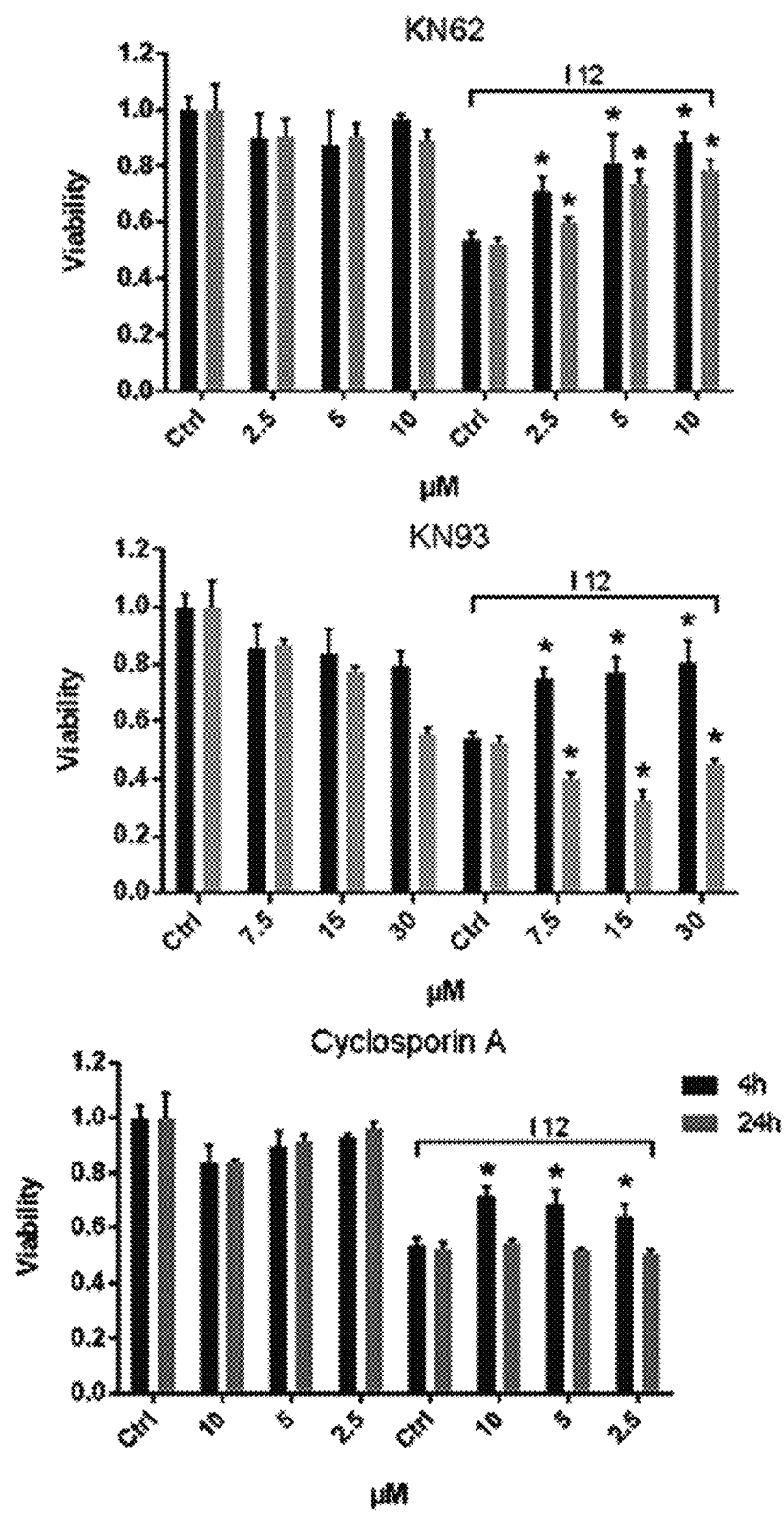
Figure 12A:
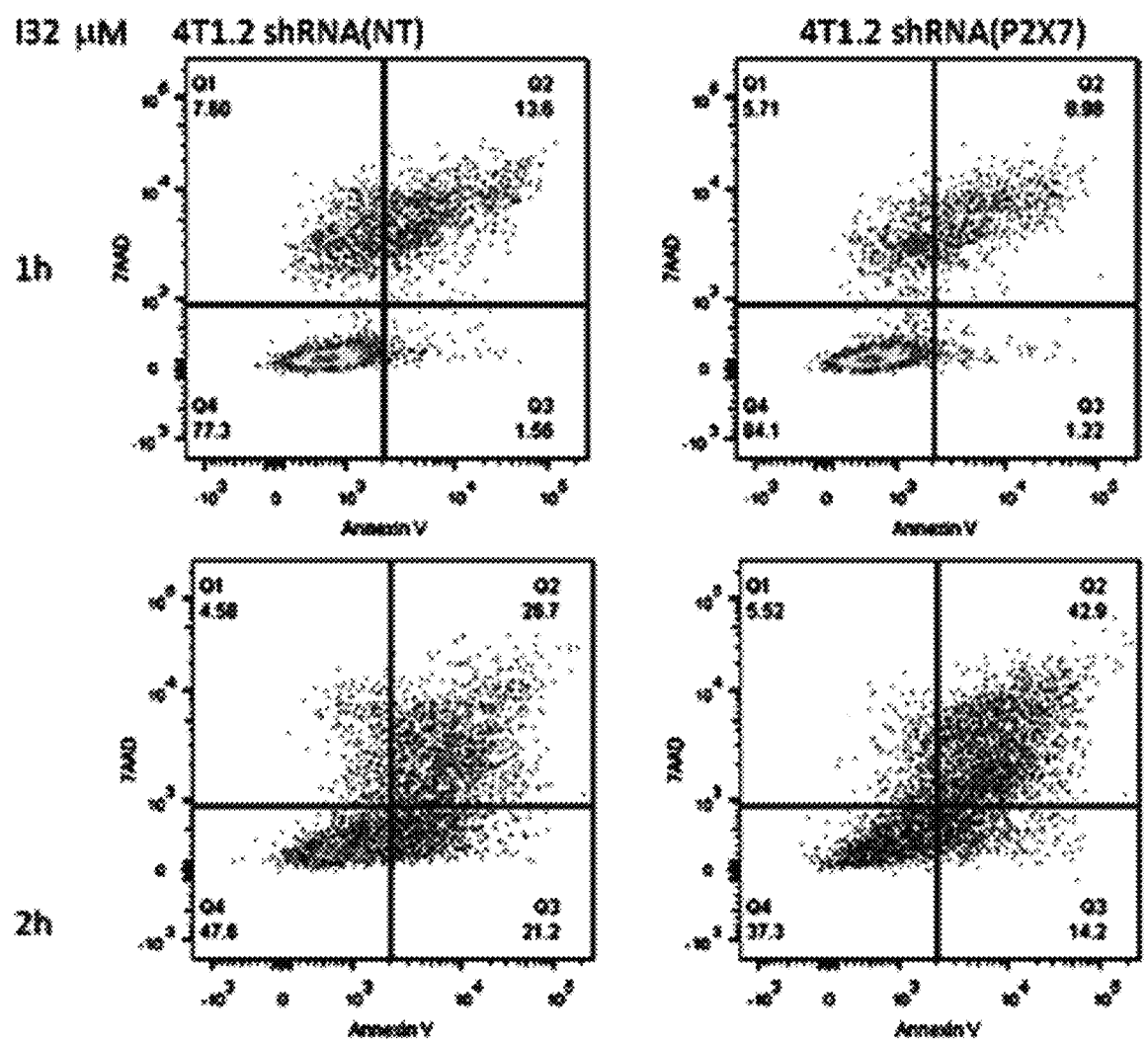
FIGS. 12A-12E. CaMKII-independent P2X7-mediated killing.
Figure 12B:
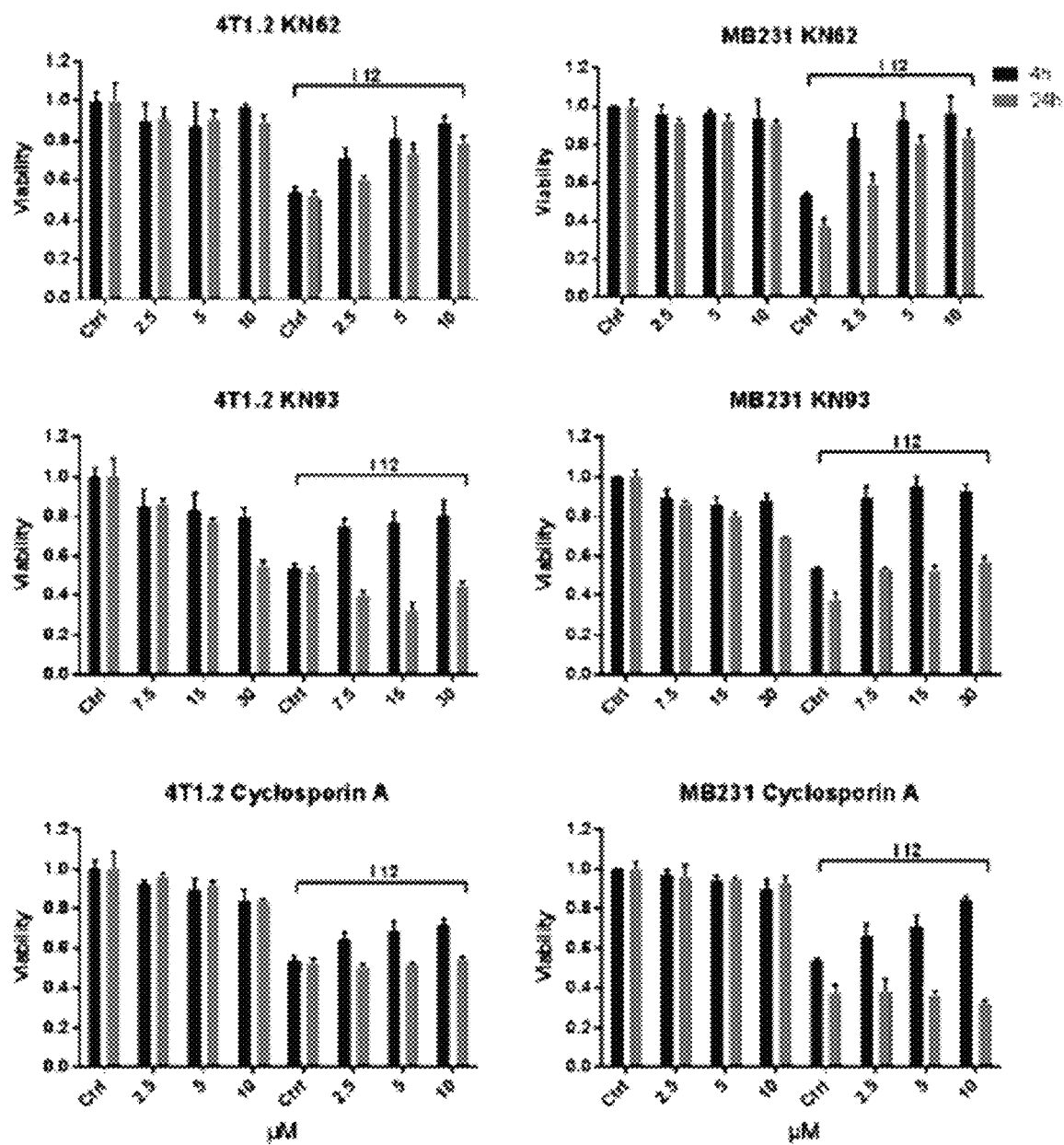
Figure 12C:
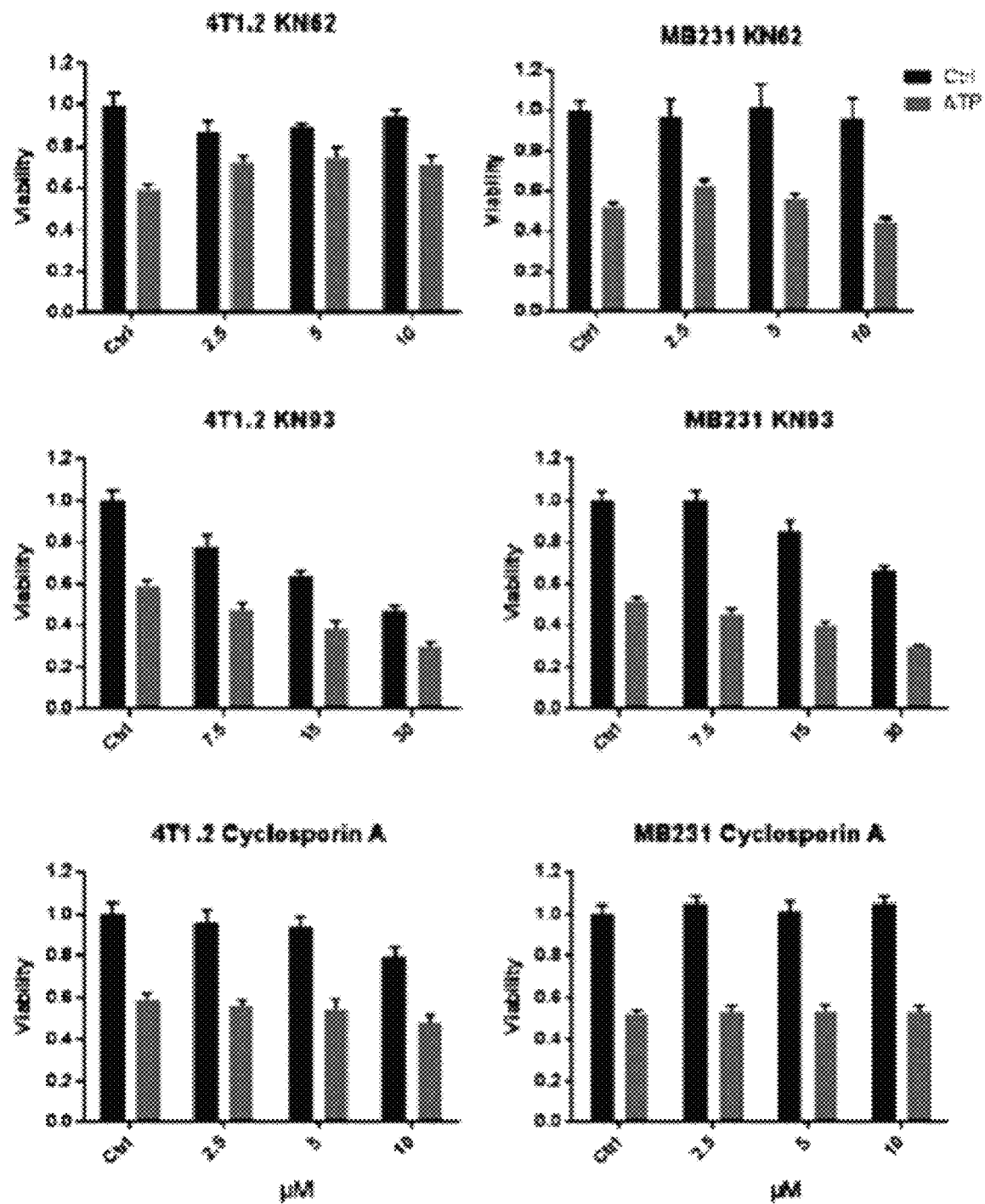

Applicants show that Ivermectin and ATP can synergistically kill even ATP- and Ivermectin-resistant human cancer cell lines (FIG. 5D). Interestingly, the P2X7 receptors appear to be involved in both the early necrotic and later apoptotic mechanisms of killing (FIG. 12A). We further compared the ability of CaMKII/MPTP and P2X7 inhibition to provide short-term (4 h) versus long-term (24 h) protection against Ivermectin. While inhibition of NADPH oxidases, CaMKII, and MPTP provided significant protection against Ivermectin cytotoxicity within the first 4 h, only KN-62 was able to provide long-term protection against Ivermectin and ATP that extended up to 24 h (FIG. 5E and FIGS. 12B-12C). At this time point, NADPH oxidases, CaMKII and MPTP inhibitors were not only ineffective but could even enhance cell death. Thus the P2X7/CaMKII inhibitor KN-62 rather uniquely confers long-term protection by blocking both the initial CaMKII-mediated cell death as well as the later P2X7-mediated killing. The early necrotic pathway induced by Ivermectin appears to progress within the first few hours of treatment and is effectively blocked by inhibitors of NADPH oxidases, CaMKII, and MPTP, consistent with massive $Ca^{2+}$ overload. This fast death pathway is likely initiated by early ATP release and P2X7-dependent caspase-1 activation, but can be transiently delayed by depletion of extracellular ATP, which allows for the slower progressing caspase-3-dependent apoptotic pathway to become prominent. The transiently protective functions of extracellular ATP during this phase can be mediated by the P2X4/P2X7/Pannexin-1-dependent ATP release or by other P2X/P2Y receptors, particularly those involved in osmotic cell volume control.

Figure 12D:
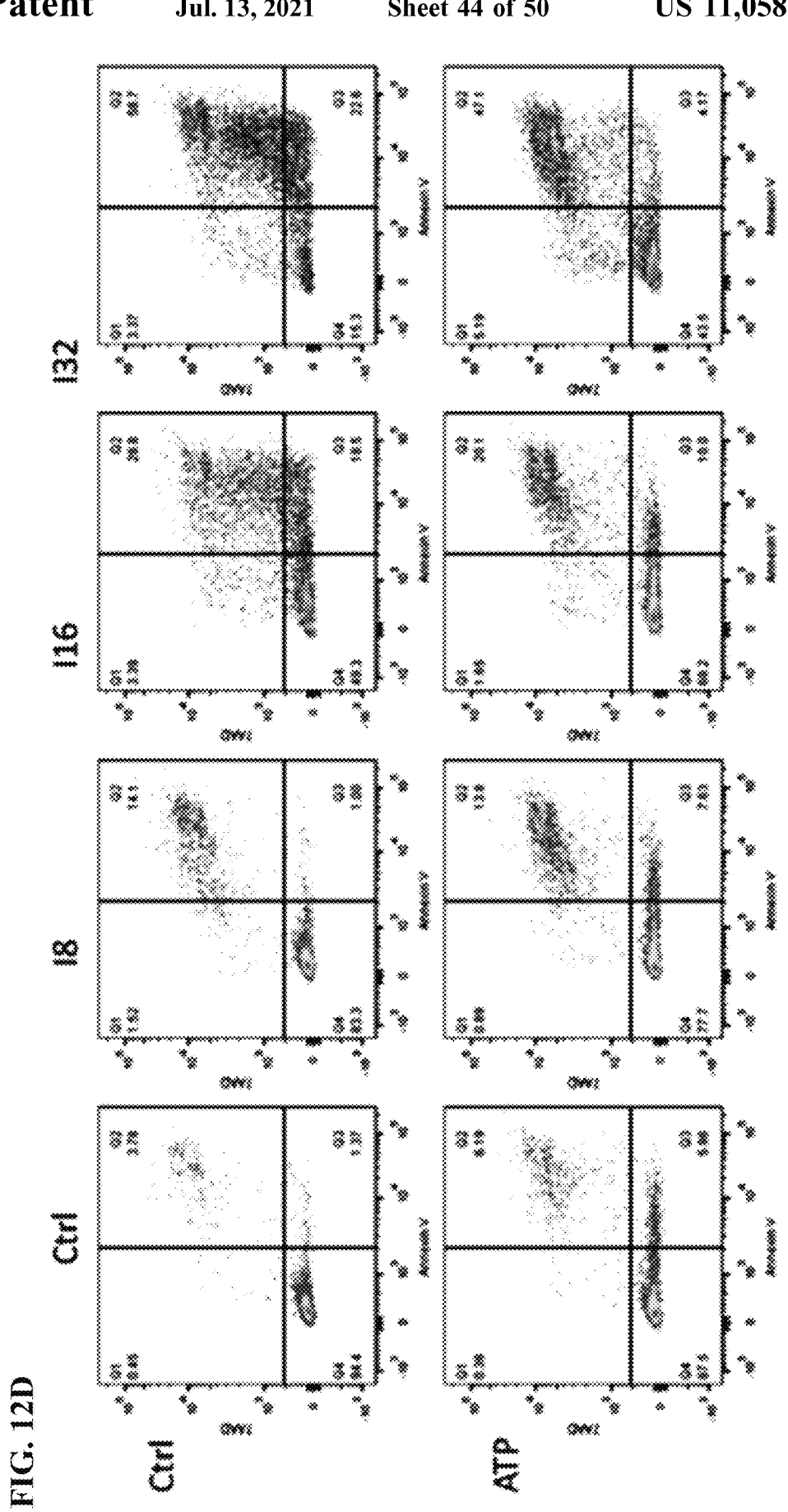
Figure 12E:
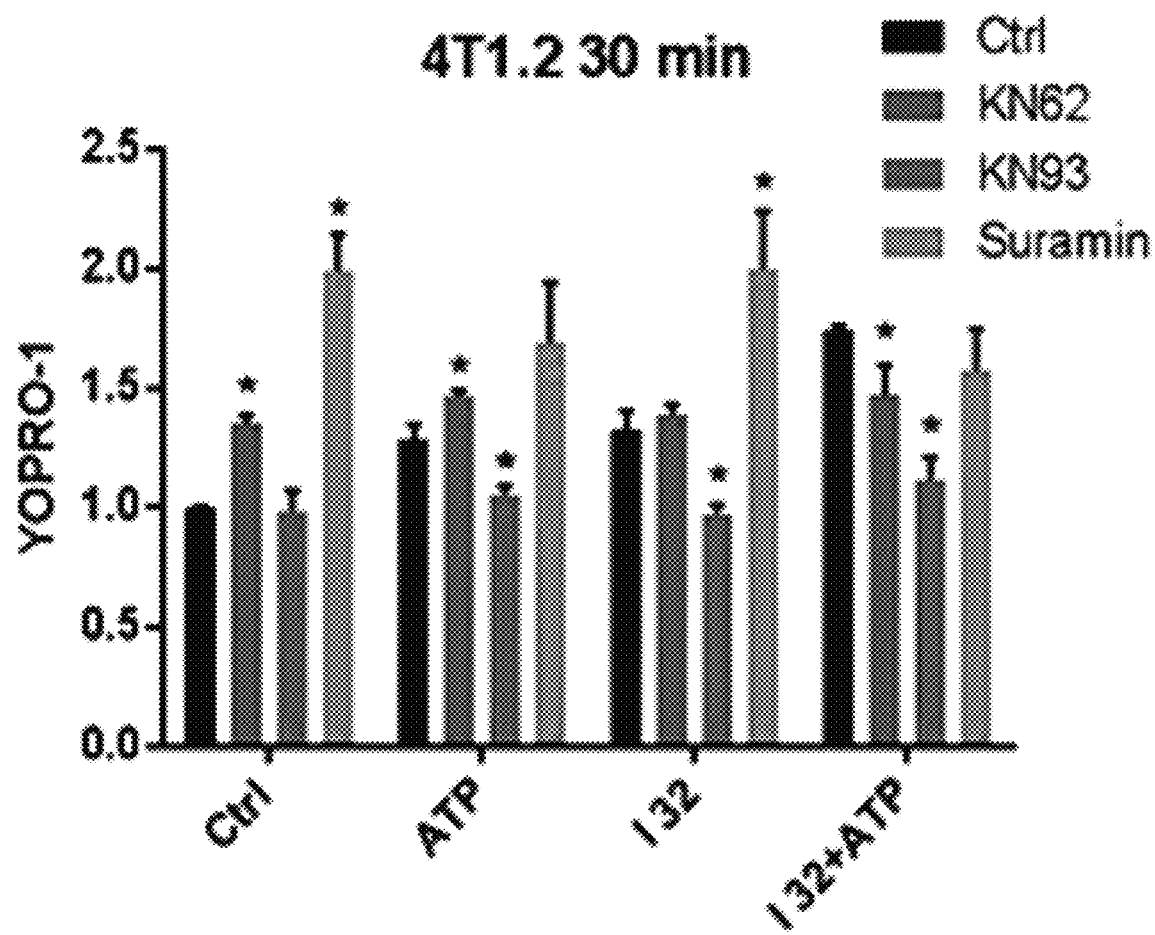

While ATP is transiently protective, the combination of ATP and Ivermectin seems to favor the necrotic over apoptotic mechanism of killing (FIG. 12D), further implicating ATP/P2X7 signaling in both the early necrotic and delayed apoptotic cell death. Consistent with the hypothesis that the P2X7 and CaMKII death pathways partially overlap is our finding that CaMKII appears to be critically important for ATP and ATP/Ivermectin-induced membrane permeabilization (FIG. 12E). Thus the balance between the apoptotic and necrotic death pathways downstream of the P2X7 receptor appears to be regulated by the complex interplay between extracellular ATP, ROS levels, and CaMKII activation.

Ivermectin Induces Autophagy and Discussion

Figure 6A:
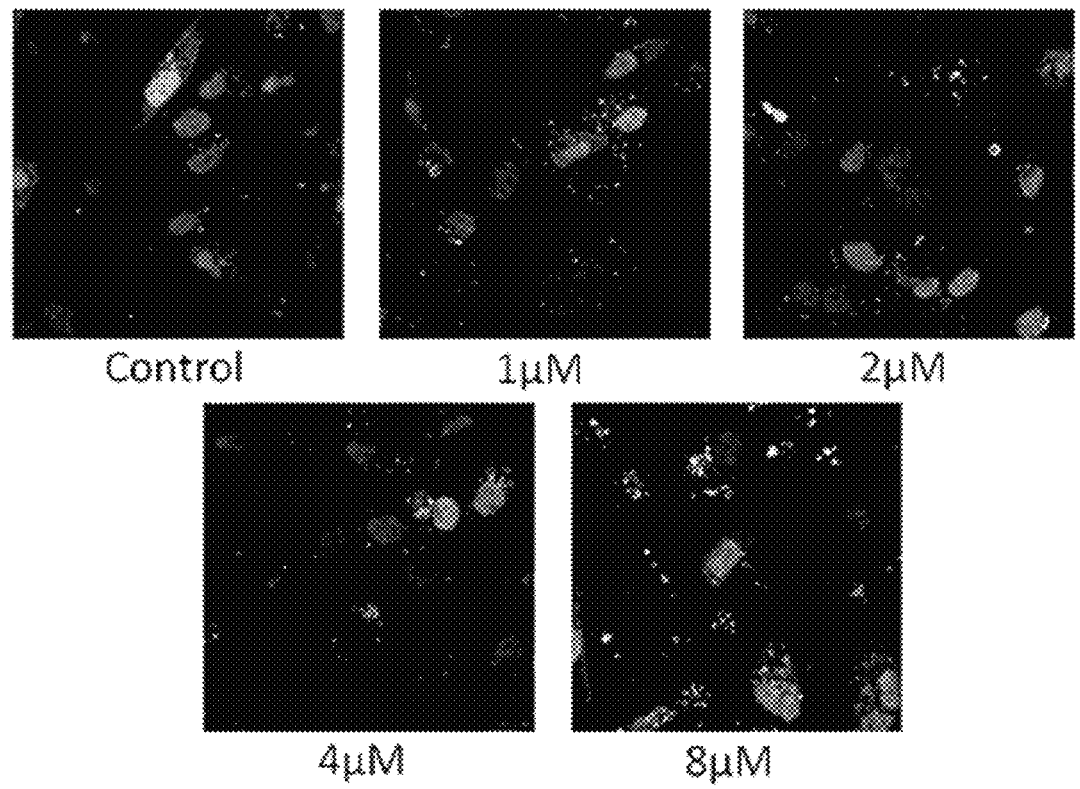
FIGS. 6A-6E. Ivermectin induces autophagy.
Figure 6B:
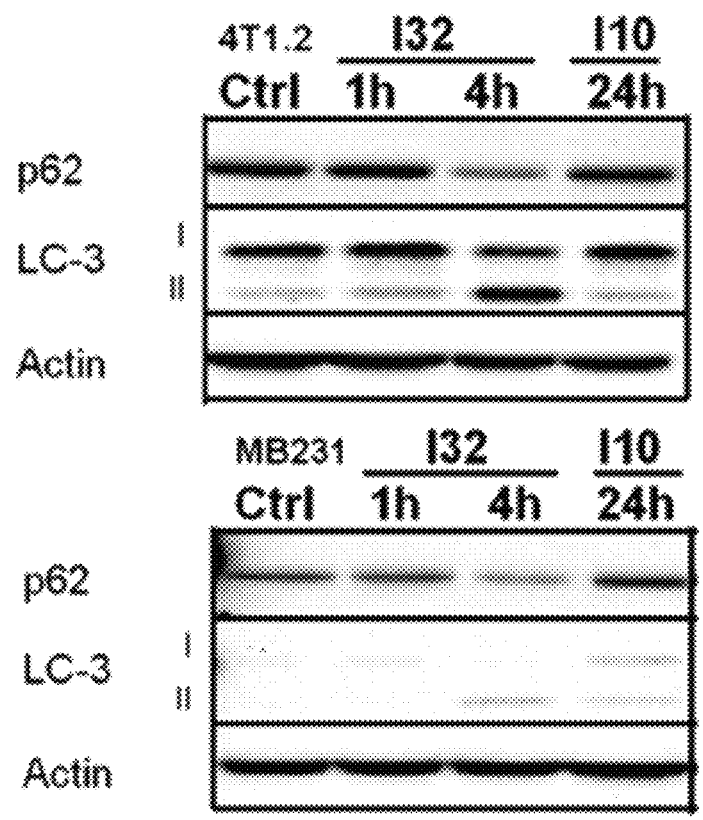
Figure 6C:
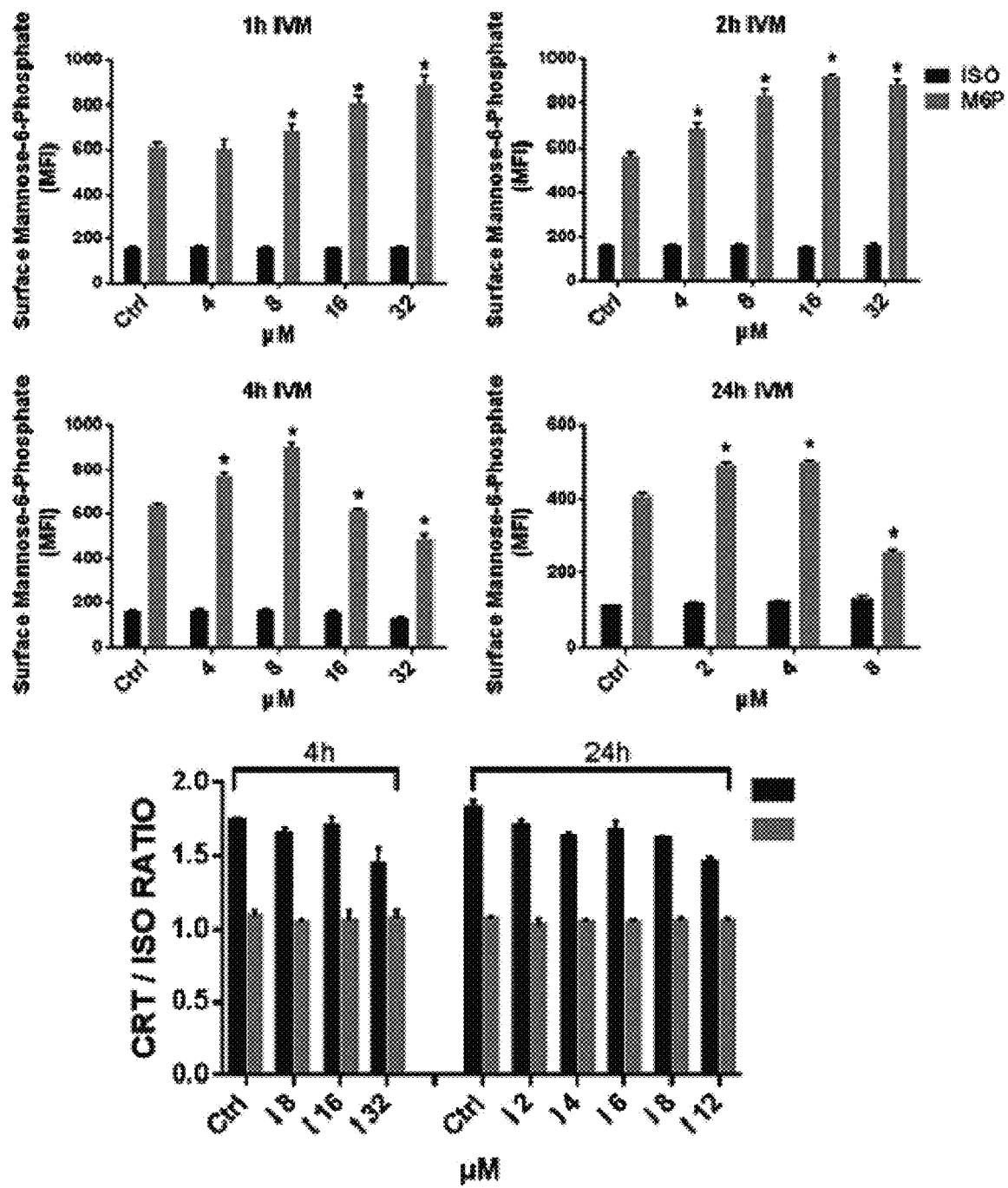
Figure 6D:
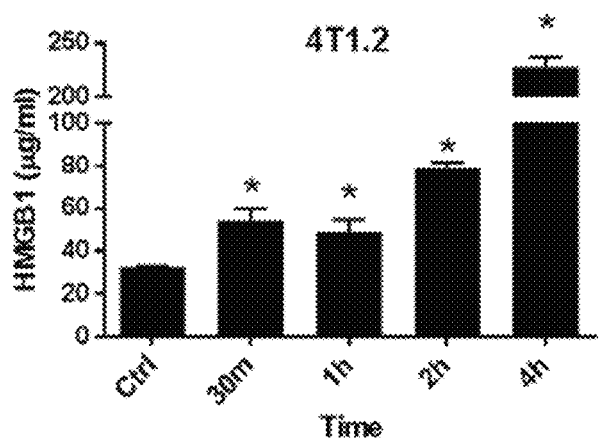
Figure 6D:
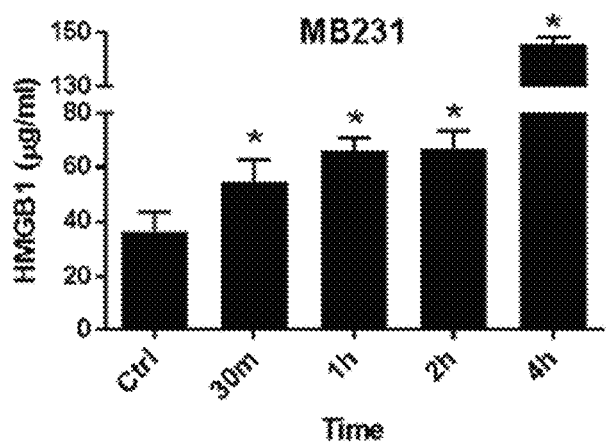
Figure 6E:
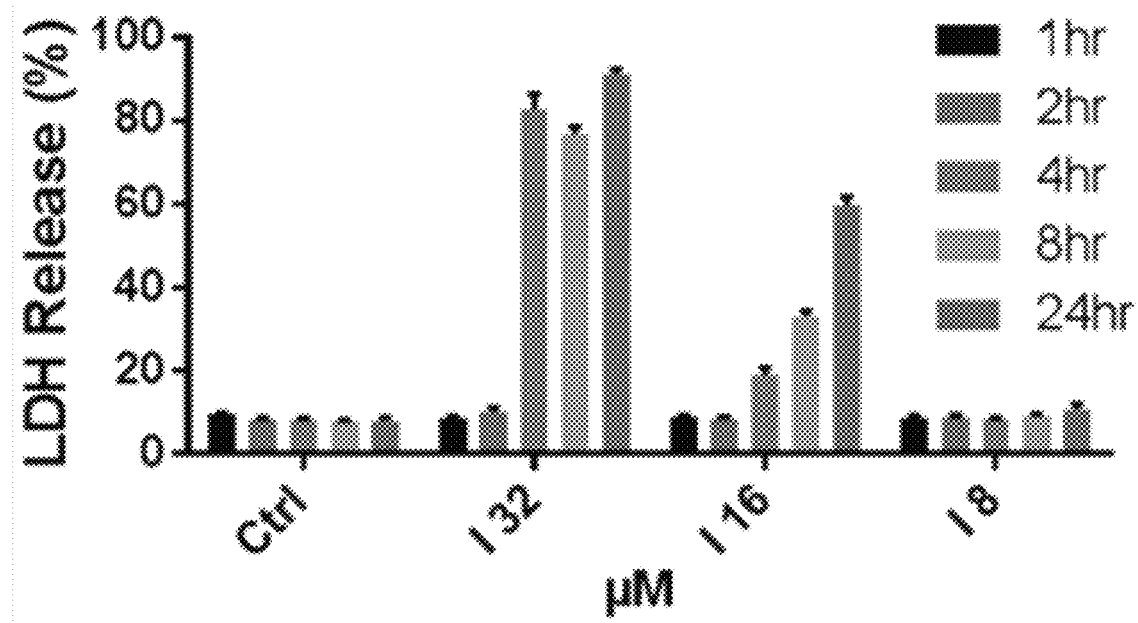
Figure 13A:
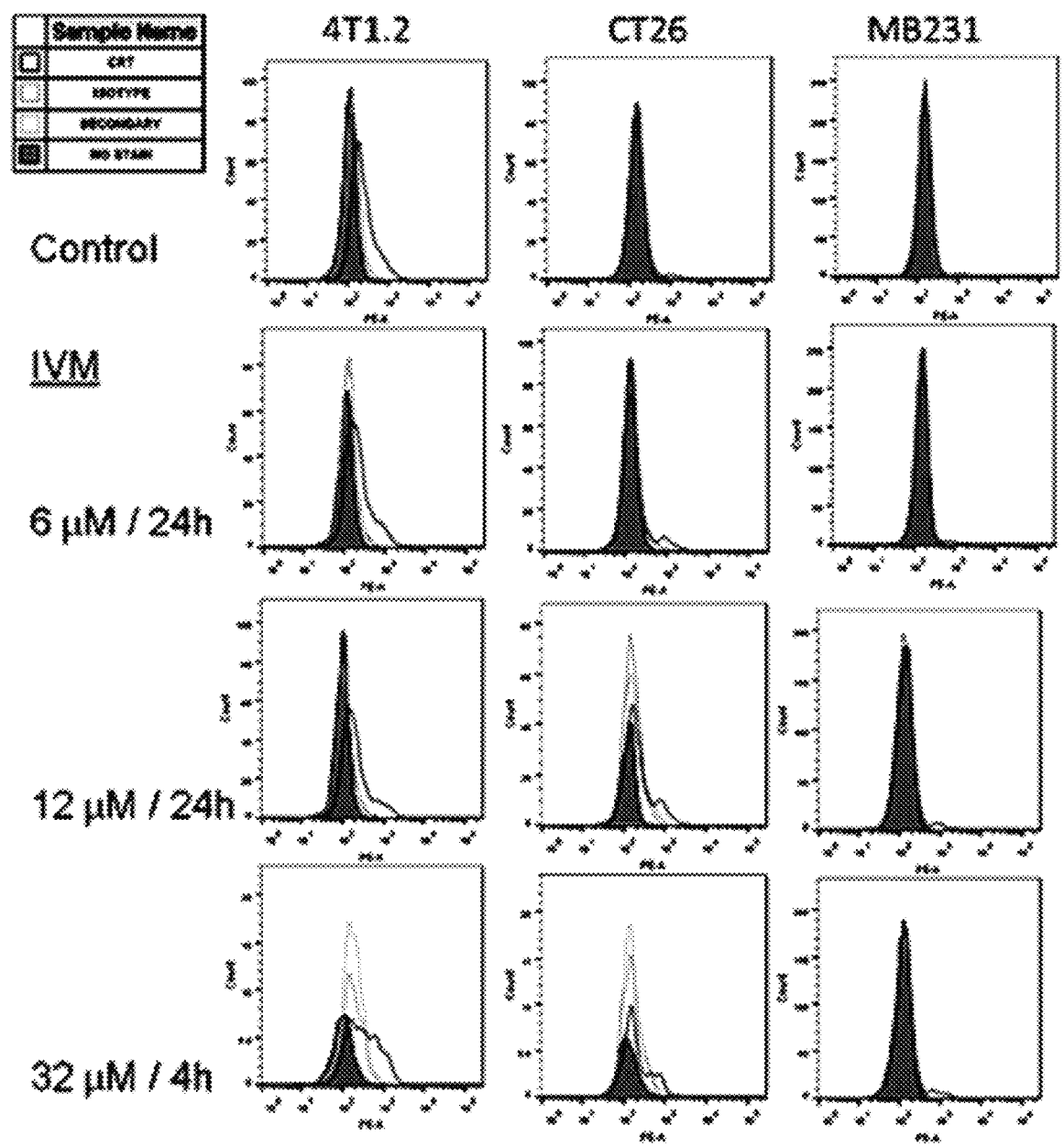
FIGS. 13A-13B. Ivermectin induces autophagy.
Figure 13B:
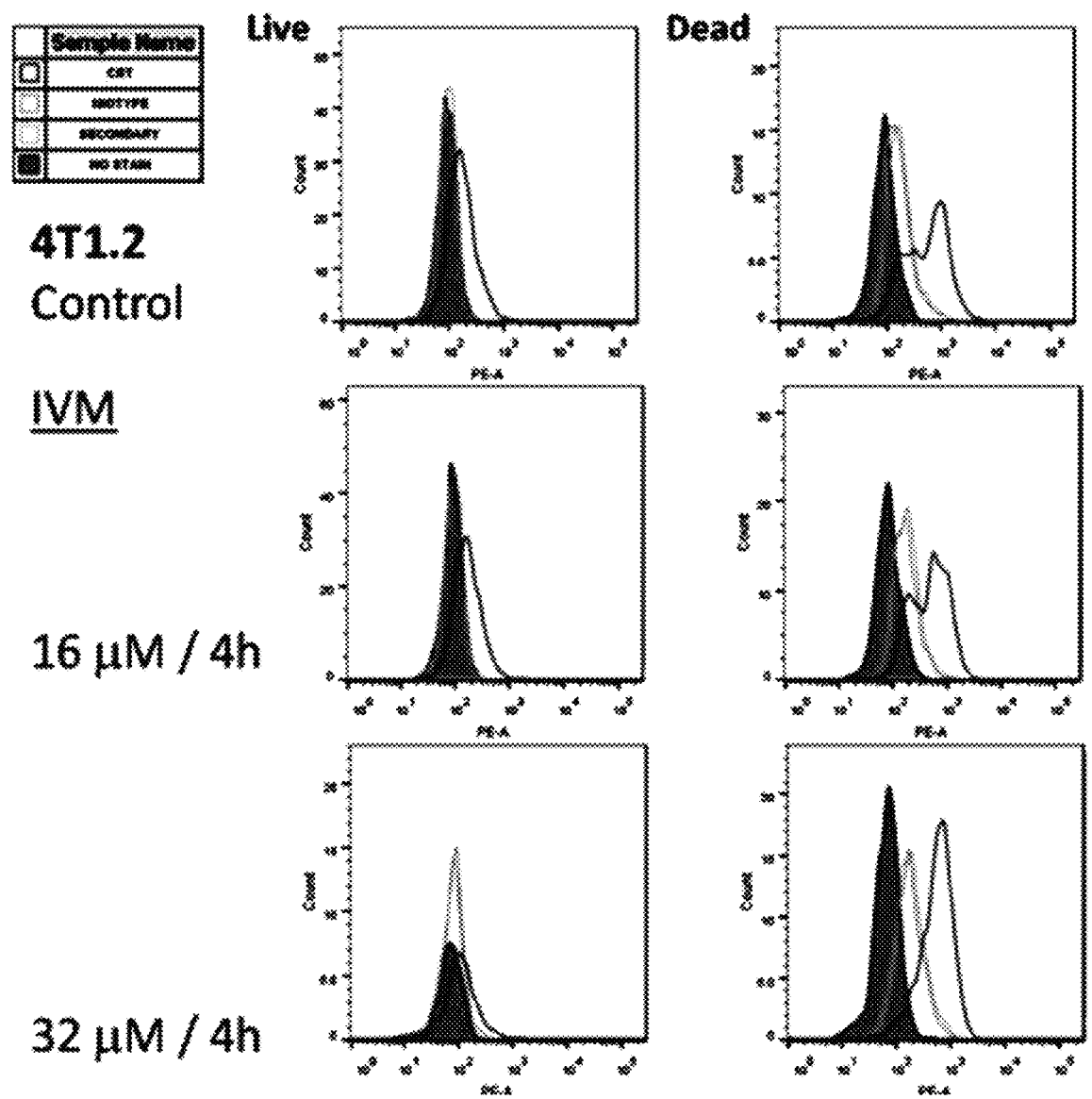
Figure 13B:
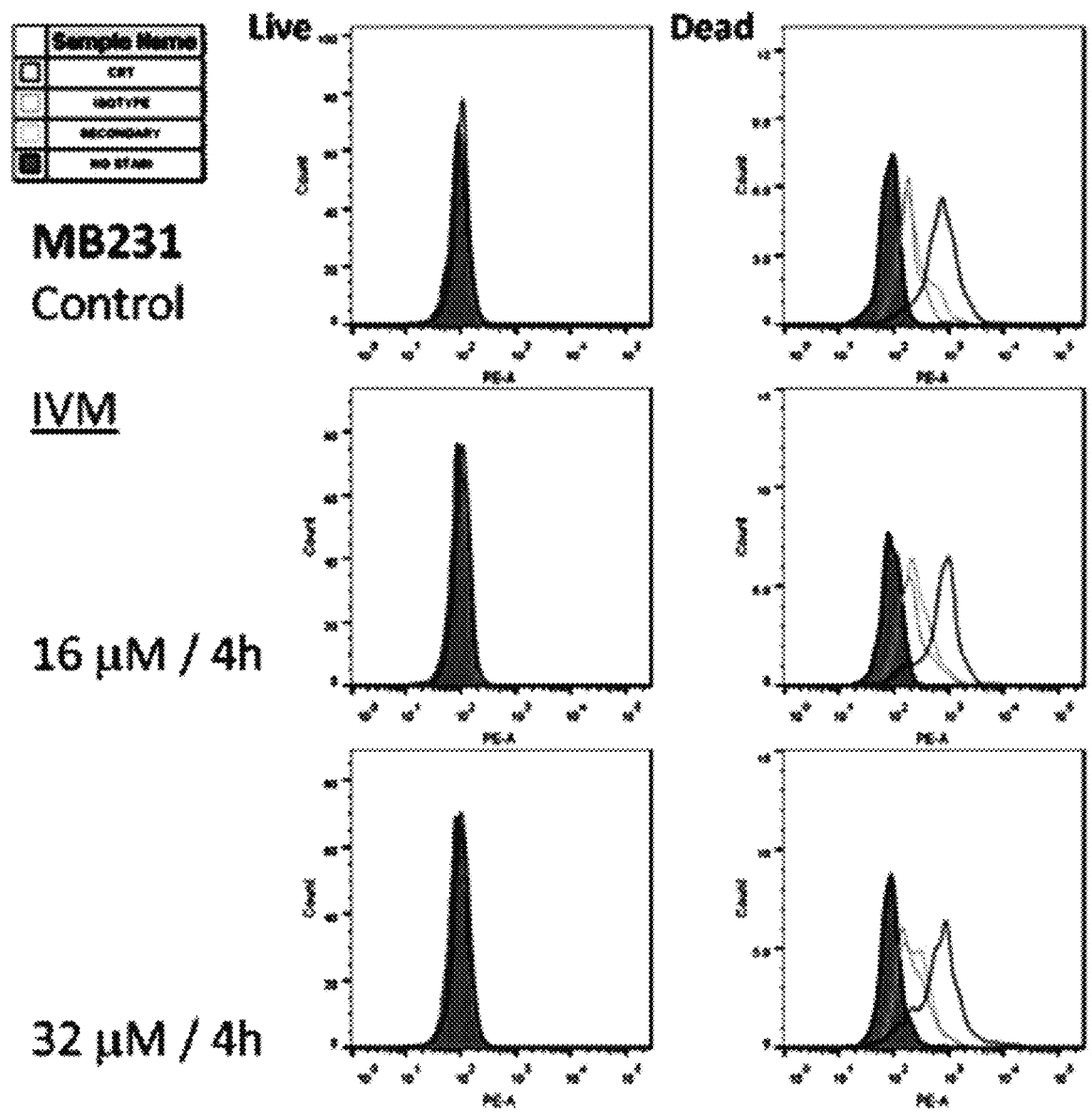
Figure 13B:
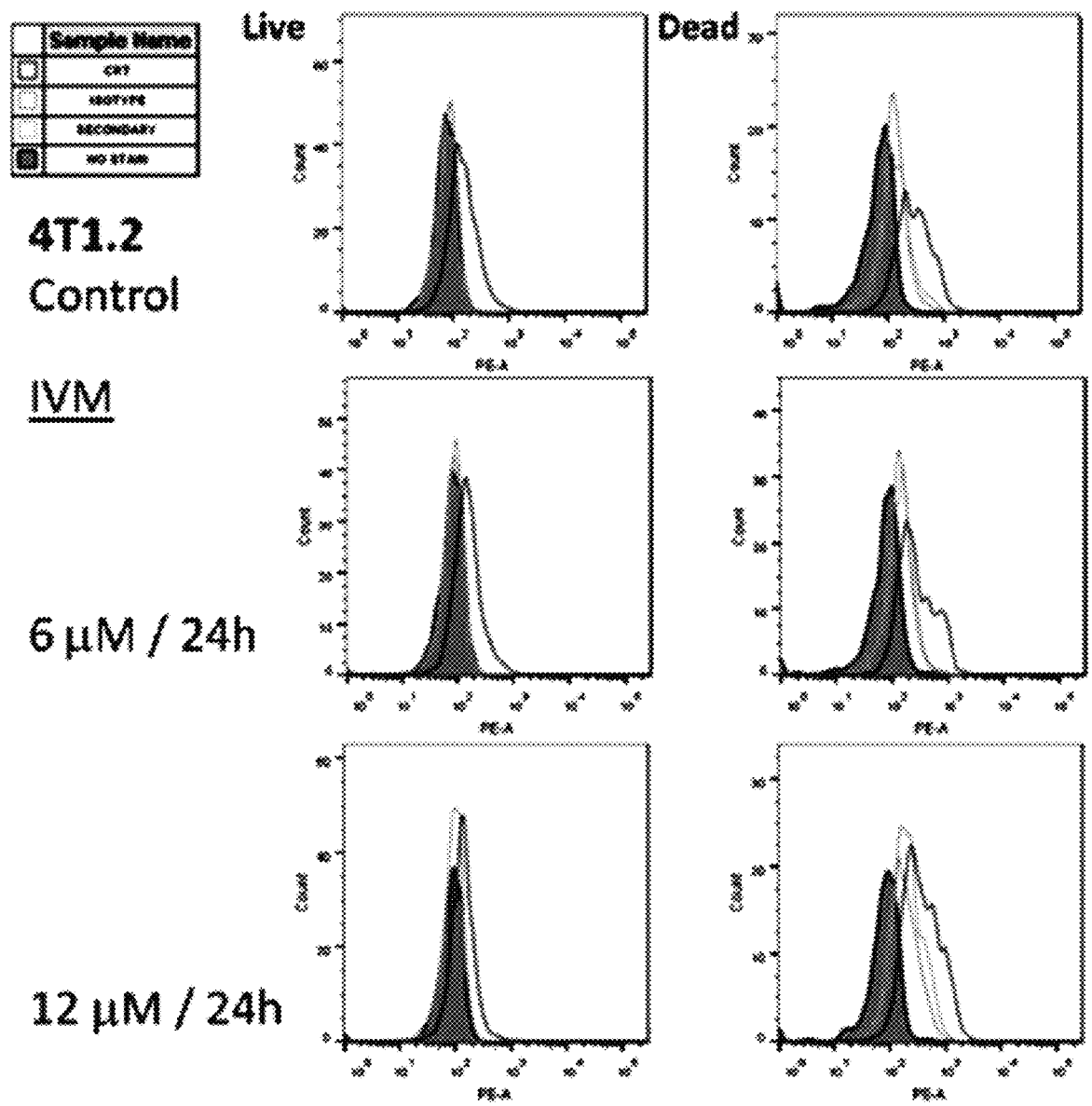
Figure 13B:
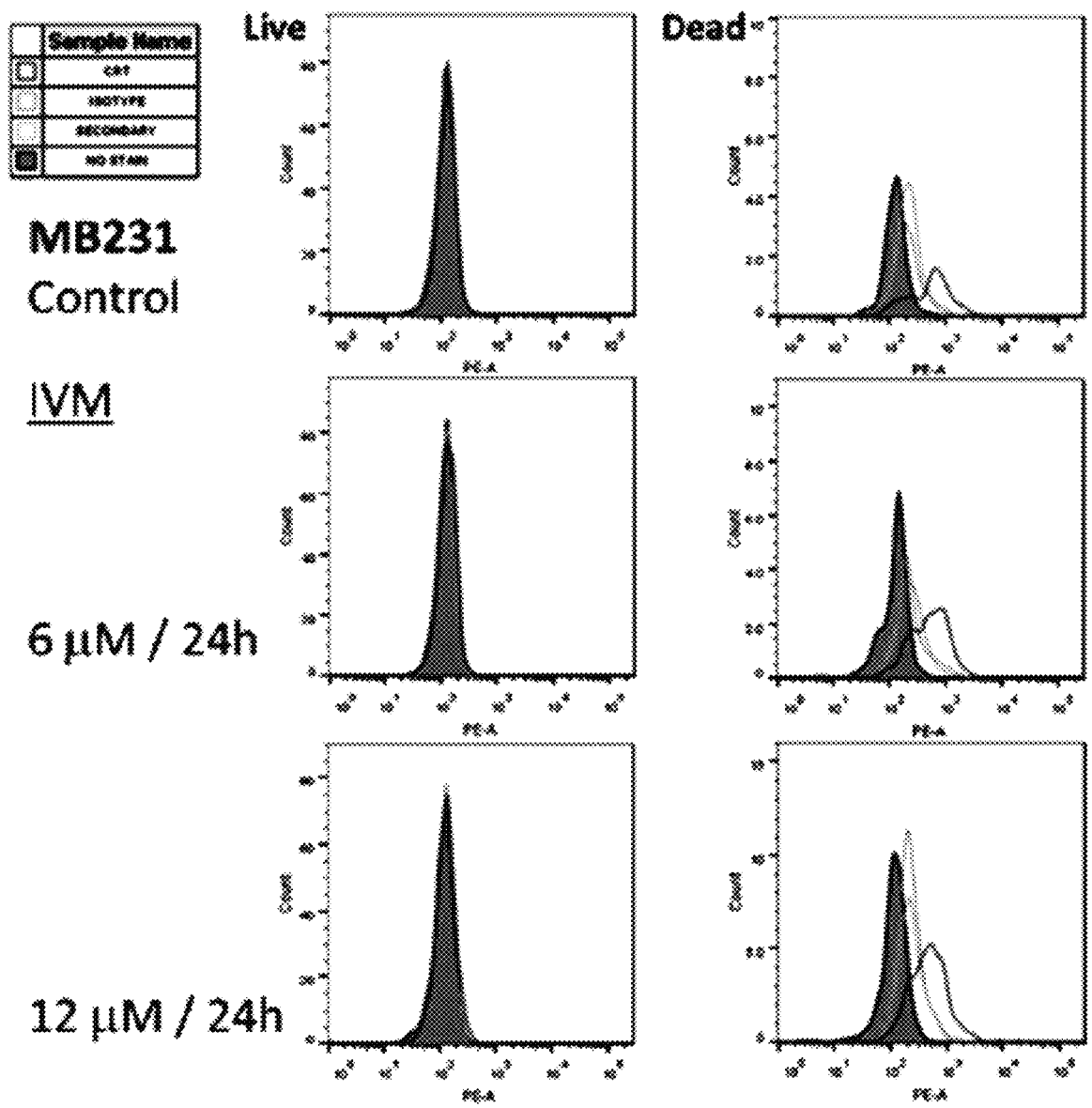

The mixed apoptotic and necrotic mechanism of killing prompted us to analyze Ivermectin's ability to modulate some features associated with immunogenic cell death: HMGB1/ATP release and the surface exposure of Calreticulin (CRT). We demonstrate that Ivermectin is a potent inducer of autophagy (FIGS. 6A-6B), consistent with its ability to stimulate ATP release and P2X4/P2X7/Pannexin-1 membrane permeabilization. Moreover, while Ivermectin does not significantly impact surface CRT (FIGS. 13A-13B and FIG. 6C, bottom panel), its ability to up-regulate plasma membrane exposure of mannose-6-phosphate (M6P) receptors could potentially render cancer cells susceptible to bystander CTL/NK cell-mediated killing (FIG. 6C, top panel). Ivermectin also appears to be a potent inducer of HMGB1 release (FIG. 6D), preceding that of LDH (FIG. 6E), consistent with both necrosis and reports describing the key role of caspase-1 in regulating non-classical secretion of HMGB1[38, 39].

Long-term clinical responses in some patients after chemotherapy involve host anti-cancer immune responses; one mechanism is the induction of immunogenic cell death (ICD) by several chemotherapeutic agents including doxorubicin and oxaliplatin. ICD is characterized by surface exposure of calreticulin and the release of ATP and HMGB1. These hallmarks of ICD have been linked to ROS-related ER stress and the induction of autophagy[40, 41]. ATP and HMGB1 mediate immunostimulatory functions in cardiac infarction and brain stroke, where ischemia/reperfusion (I/R) injury is associated with massive inflammatory responses and necrotic cell death through P2X7-dependent purinergic signaling and NLRP3/caspase-1-dependent pyroptosis. Pyroptosis is an important defense mechanism that might have evolved to protect myeloid and epithelial cells against certain intracellular parasites including viruses and bacteria (e.g. *Salmonella* and *Listeria*)[42, 43]. Components of activated inflammasomes can be secreted and re-captured by other myeloid cells, providing a potent amplification step stimulating protective immunity.

Caspase-1 has also been reported to regulate non-classical secretion of HMGB1 and serves as a link between HMGB1 and purinergic signaling[39]. ATP and HMGB1 function as prototypic danger signals that can promote immune mediated destruction as well as inflammatory-reparative responses. The interplay between ATP and HMGB1 appears to be essential for tumor growth, angiogenesis and metastasis.

Hypoxia and the maintenance of elevated levels of extracellular ATP and HMGB 1 are characteristics shared between the tumor microenvironment and sites of I/R injury. However, it is still unclear how tumors manage to effectively utilize the tumor promoting functions of the ATP/HMGB1/caspase-1 system while successfully evading immune-mediated destruction. Cancer cells of diverse origin are known to be very sensitive to high concentrations of extracellular ATP. This is likely due to the expression of higher levels of P2X7 receptors that have been correlated with tumor survival, progression and metastasis[7, 8, 49] and can be potentially linked to the constitutive activation of the inflammasome pathway in cancer[17]. Apart from being directly cytotoxic, high extracellular ATP concentrations can break local immunosuppression and promote inflammation, which is prevented by extracellular ATPases (CD39/CD73) degrading ATP to immunosuppressive adenosine. Tumor growth and survival is therefore critically dependent on an optimal balance between the pro-survival and cytotoxic functions of purinergic signaling and caspase-1.

The sensitivity of tumors to ATP and agonistic analogues has been extensively investigated but the therapeutic window for such systemic approaches might be limited by toxicity and lack of tumor specificity[1]. To circumvent this issue, we proposed to modulate purinergic signaling with agents that enhance the sensitivity of the P2X4/P2X7/Pannexin-1 complex to ATP. Such an approach capitalizes on the high levels of extracellular ATP characteristic of the tumor microenvironment, thus minimizing availability and systemic toxicity issues.

Ivermectin potentiates P2X4/P2X7 purinergic signaling in cancer cells correlates to the ATP rich tumor microenvironment, thus providing a mechanistic explanation for this phenomenon.

Figure 7:
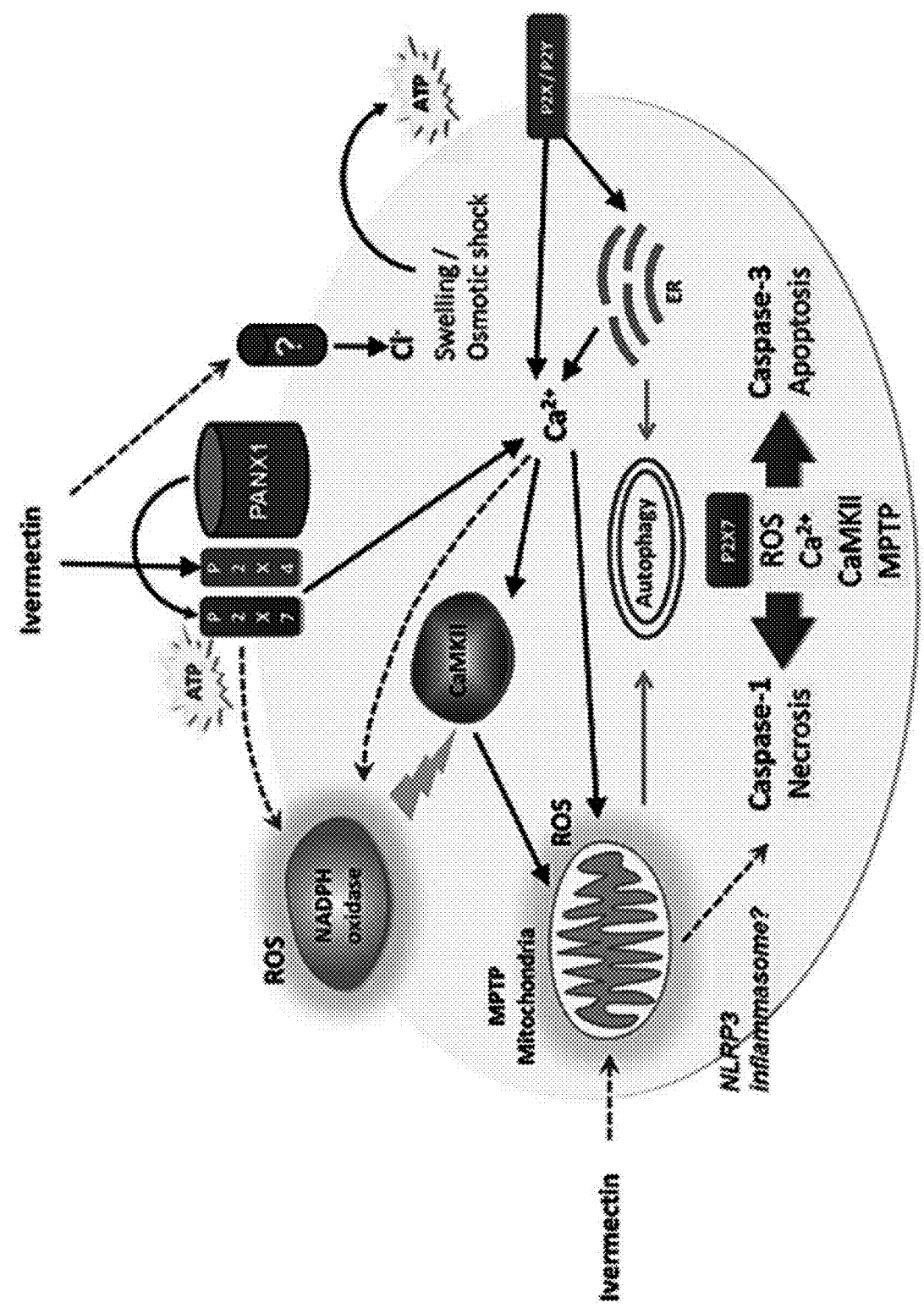
FIG. 7. Cartoon depicting model of P2X4/P2X7/Pannexin-l-induced cancer cell death. Ivermectin induces P2X4/P2X7-dependent activation of Pannexin-1 channels and release of ATP. The release of ATP might be transiently protective, but only in cell types that are highly sensitive to Ivermectin-induces cell swelling when ATP and $Ca^{2+}$ signaling are essential for control of cell volume. In cancer cells where no cell size changes can be observed (for example human TNBC MDA-MB-231 cells), high concentrations of ATP (1-3 mM) immediately enhance Ivermectin cytotoxicity. Potentiated P2X7 receptor signaling drives a fast progressing necrotic/pyroptotic mechanism driven by NADPH oxidases-generated ROS, cytosolic $Ca^{2+}$/CaMKII activation, and MPTP, and characterized by caspase-1 cleavage, due to possible NLRP3 inflammasome activation. Necrotic killing is followed by a slower progressing apoptotic cell death program mediated by caspase-3 activation. The failure of the default apoptotic pathway might be attributed to faster activation of caspase-1, inadequate autophagic control of mitochondrial MPTP, collapse of cellular energy metabolism, resulting in rapid progression of necrotic cell death. Damage to mitochondria and ER stress as well as potential depletion of cellular ATP reserves simultaneously promote autophagy that might render even the slower apoptotic pathway immunogenic.

The enhanced tumor specificity of Ivermectin can also be attributed to the Warburg effect and the high dependence on glycolysis under the hypoxic tumor environment in vivo. Caspase-1 has multiple downstream effector mechanisms that include cleavage of key enzymes in the glycolytic pathway. Such activity could potentially compromise cellular energetics, ER $Ca^{2+}$ ATPases, and cytosolic $Ca^{2+}$ homeostasis, resulting in failure of the default immunologically silent apoptotic pathway and the prevalence of CaMKII/MPTP-mediated necrotic cell death. In support of this hypothesis, applicants have shown that Ivermectin-induced cell death is consistently mediated through the P2X7, CaM-KII and MPTP pathways in all mouse and human cancer cell lines tested (FIG. 7). Ivermectin directly impacts the balance between ATP-dependent pro-survival and cytotoxic signals, converting a key pro-survival and tumor-promoting pathway into a P2X7- and caspase-l-mediated immunogenic cell death. P2 purinergic receptors provide essential anti-apoptotic and pro-survival $Ca^{2+}$-mediated signals to cancer cells allowing them to overcome various therapeutic or environmental stresses. ATP-dependent $Ca^{2+}$ signaling also appears to be involved in regulation of cell volume. P2X7 receptors and CaMKII mediate trophic and protective purinergic/$Ca^{2+}$ signaling in various cell types, but the same signaling cascade can promote both survival and cell death dependent on signaling strength or duration. Thus, CaMKII/MPTP-mediated necrotic cell death appears to result from overstimulation of the P2X7 pathway. Limited MPTP could be contained by $Ca^{2+}$-induced autophagic removal of damaged mitochondria and stressed ER; whereas a massive collapse of mitochondria and mtDNA-stimulated NLRP3 inflammasome activation would lead to necrosis. Such a massive mitochondrial collapse followed by autophagic vacuolization was indeed observed by us in Ivermectin-treated MCF7 breast cancer cells.

This study suggest that the anti-cancer properties of Ivermectin can be potentiated by therapies inducing autophagy, ATP release, and ROS, such as irradiation and doxorubicin. ATP-regulated ROS are known to play roles in inflammation, NFKB signaling, and recruitment of leukocytes. Thus, purinergic-regulated ROS may be involved in maintenance of tissue homeostasis in response to cellular stress or to directly promote cancer cell growth and survival.

Ivermectin promotes a novel form of cancer cell death involving a combination of enhanced autophagic apoptosis and highly inflammatory regulated necrosis, consistent with pyroptosis. The induction of autophagy is particularly interesting since it represents an important cellular defense mechanism against various chemotherapeutics, while enhancing immunogenicity and rendering cancer cells susceptible to immune mediated killing. The P2X4/P2X7/Pannexin-1 system regulates ATP release from autophagic cancer cells but also functions as a positive feedback/amplification step that is involved in the recruitment and activation of T cells, macrophages and dendritic cells. The anti-cancer properties of Ivermectin are therefore not limited to direct cytotoxicity but additionally its immunomodulatory potential and impact on cancer immunotherapy.

Material and Methods

Cell lines. 4T1.2 Balb/c triple-negative breast cancer cells were obtained from Robin Anderson, PhD, Peter MacCallum Cancer Centre, Melbourne, Australia. The human breast cancer cell lines MDA-MB-231(triple-negative), MCF7 (ER-positive), SKBR3 (Her-2-positive) were obtained from Robert Hickey, City of Hope National Medical Center. The murine B16 (C57BL/6 mouse melanoma), CT26 (Balb/c colon adenocarcinoma), and DDHer2 (Balb/c Her-2/neu breast carcinoma) cell lines were obtained from Glenn Dranoff, M D, Dana-Farber Cancer Institute, Boston. Human melanoma (A2058, A375) and pancreatic cancer (PANC1, MiaPaca-2) lines were a gift from Don Diamond, City of Hope National Medical Center. Human Prostate (DU145), Head and Neck (A253) and Leukemia (MV411) cells were obtain from Marcin Kortylewski Lab, City of Hope National Medical Center. All cancer cell lines were grown in RPMI medium supplemented with 10% FBS, Pen/Strep, Glutamine, and HEPES Buffer (R10).

Reagents. The following reagents were used: Ivermectin (Sigma 18898-250MG), KN-93 (Tocris, 5215-1MG), Cyclosporin A (Tocris, 1101-100MG), KN-62 (Tocris, 1277-1MG), PSB 069 (Santa Cruz, sc-204216 10MG), DCPIB (Tocris, 1540-10MG), A438079 (Tocris, 2972-10MG), z-vad-fmk (Enzo Life Sciences, ALX-260-020-M001-1MG), vx765 (InvivoGen, inh-vx765-1-10MG), oxATP (Sigma Aldrich, A6779-25MG), PPAD (Sigma Aldrich, P178-10MG), DPI (Sigma Aldrich, D2926-10MG), NAC (Sigma Aldrich, A9165-25MG), Suramin (Sigma Aldrich, S2671-100MG), Necrostatin (Enzo Life Sciences, BML-AP309-0020-20MG), Digoxin (Sigma Aldrich, D6003-100MG), Apyrase (New England Biolabs, M03935-10,000 milliunits), ATP (Sigma Aldrich, A2383-1G), Pannexin-l-Inhibitor (AnaSpec, 61911-1MG), Probenecid (Sigma Aldrich, P8761-25G), YOPRO-1 Iodide (Life Technologies, Y3603-1mL), GSH (Sigma Aldrich, G4251-1G).

Cell viability. Cancer cells were plated on 96 well flat-bottom plates and allowed to attach overnight. Cells were then pre-incubated with drugs for 1 h and treated with Ivermectin for 4 h. In the case of 24 h and 48 h incubations the cells, Ivermectin and drugs were plated together. All treatments and controls were done in triplicate wells and results were validated in at least two independent experiments. Following treatment the plates were washed once with PBS and cell viability was measured using the acid phosphatase assay. Briefly, cells were incubated for 1h at 37° C. in 100 µL assay buffer (0.16 M sodium acetate, 0.1% Triton-X-100, supplemented with 4-Nitrophenyl phosphate disodium salt hexahydrate, Sigma Aldrich, at 0.00263 g/ml). Reaction was stopped using 10 µL of 1N sodium hydroxide. Absorption at 405 nm was measured within 10 min using a multi-well plate reader. Mode of cell death and viability of cells in suspension was evaluated using flow cytometry. Briefly, cancer cells were pre-incubated with drugs for 30 min to 1 h, as indicated, treated with Ivermectin for 4 h in 5 ml FACS tubes, washed twice in PBS and stained with PE-conjugated Annexin V and 7AAD (1 µl per 100 µl/200,000 cancer cells) for 15 min.

Cytosolic $Cl^-$ influx. Cancer cells in suspension were treated with various doses of Ivermectin in R10 medium for 1h at 37° C. and 5% CO2. Cells were then washed with PBS and loaded with 10 µM SPQ probe (Life Technologies, M440) in a hypotonic buffer containing 50% PBS and 50% double distilled water. Following brief 15 min incubation at room temperature in the dark cells were washed once with PBS and immediately analyzed by flow cytometry measuring fluorescence in the AF350 channel.

Cytosolic $Ca^{2+}$ flux. Cancer cells in suspension were washed with PBS and loaded with 1 µM Rhod-3 AM (Life Technologies, R10145) for 30 min at room temperature in the dark. Cells were washed with PBS couple of times and treated with various doses of Ivermectin in R10 medium. Cells were incubated for 15 min to 4 h in 5 ml FACS tubes at 37° C. and 5% CO2, followed by immediate flow cytometry analysis of fluorescence in the PE channel. Chelating of extracellular and intracellular $Ca^{2+}$ was performed by supplementing the Ivermectin treatment medium with 1 mM EDTA (USB Corp, 15694) or by adding 20 µM BAPTA-AM (Tocris, 2787) to the Rhod-3 AM loading solution, respectively.

Mitochondrial membrane potential. Cancer cells in suspension were washed with PBS and loaded with 2 µM JC-1 (Life Technologies, T3168) for 15 min at room temperature in the dark. Cells were washed twice with PBS and treated with various doses of Ivermectin in R10 medium. Cells were incubated for 1 h/4 h in 5 ml FACS tubes at 37° C. and 5% CO2. After 1h/4h of treatment cells were analyzed by flow cytometry. Mitochondrial polarization was evaluated by measuring the corresponding changes in fluorescence in the FITC and PE channels. Treatment with 50 µM CCCP (Sigma C2759-100MG) was used as a positive control.

Plasma membrane polarization. Cancer cells in suspension were treated with various doses of Ivermectin in the presence of 0.5 µM $DiBAC_4$ (3) (Sigma D8189). Treatments were performed in serum free RPMI medium and cells were analyzed by flow cytometry after 1h of incubation. De-/hyper-polarization results in increased/decreased fluorescence in the GFP channel, respectively.

Reactive oxygen and nitrogen species. Cancer cells in suspension were washed with PBS and loaded with 50 µM H2DCFDA (Molecular Probes, Life Technologies, D399) or 5 µM DAF-2 (Cayman Chemical, Catalog #85165) for 30 min at room temperature in the dark. Cells were washed twice with PBS and treated with various doses of Ivermectin in R10 medium. Cells were incubated for 1h in 5 ml FACS tubes at 37° C. and 5% CO2, and immediately analyzed by flow cytometry. Generation of intracellular ROS and NO results in corresponding increases in the GFP fluorescence of the H2DCFDA and DAF-2 probes, respectively.

Caspase activation and PARP cleavage. Cancer cells in suspension were treated with Ivermectin in 5 ml FACS tubes for 4 h. Analysis of caspase activation was done using the FLICA® 660 Caspase 3/7 Assay Kit (ImmunoChemistry Technologies 9125) and the FAM FLICA™ Caspase 1 Assay Kit (ImmunoChemistry Technologies 98), following manufacturers' instructions. PARP cleavage was analyzed after fixing the cells (eBioscience, Cat #00-5123 and Cat #00-5223) for 30 min at RT. Cells were then washed twice with permeabilization Buffer (eBioscience, Cat #00-8333) and then stained with FITC-conjugated antibody specific for cleaved PARP (10 µl per 100 µl, BD Biosciences 558576) for 1 hr at RT. Cells were washed twice with permeabilization buffer, followed by flow cytometry analysis.

Generation of P2X7 receptor knockdown 4T1.2 cells. 4T1.2 cells were transduced using Sigma mission shRNA lentiviral transduction particle with four P2X7 shRNA (NM_011027/TRCN0000068568, NM_011027/TRCN000-0068570, NM_011027/TRCN0000068571, NM_011027/TRCN0000068572) or Non-Target control (SHC002V). The viral particles were added to growing cells in the presence of 8 µg/ul POLYBRENE® (Sigma, St Louis, Mo.), and incubated overnight at 37° C. Puromycin selection (2000 ng/ml) was done from third day onwards to select for stably transformed cells.

Extracellular ATP release. 4T1.2 and MDA-MB231 cells were plated onto 96 well flat-bottom plates at a density of 10,000 cells per well and incubated overnight before transfection with pMetLuc-Mem luciferase vector, following manufacturers' instructions (Clontech Laboratories Inc). Forty eight hours post transfection, stable transformants were selected using G418 (1000 µg /ml). The cancer cells engineered to stably express the membrane-bound Luciferase were treated with Ivermectin for 30 min-4 h and luminescence was measured in the presence of 2 µM Luciferin. ATP concentration in Ivermectin treated supernatants was measured using ATP determination kit (Life Technologies, A22066) following manufacturers' instructions.

Real-time RT-PCR analysis. Total RNA was isolated from cancer and normal cell using Qiagen micro RNA isolation kit according to manufacturer's instructions. The cDNA were synthesized from 1 µg of total RNA using SuperScript™ II reverse transcriptase kit, (Invitrogen Inc) and oligo dT. Using mouse gene specific primers for P2X7 (forward 5'-TGGATGACAAGAACACGGATG-3' (SEQ ID NO:1) and reverse 5'-CAGGATGTCAAAACGGATGC-3') (SEQ ID NO:2) and 18s RNA primers as controls, real-time RT-PCR was performed in duplicate for each sample in an iCycler (BioRad). Reactions (25 µl) contained cDNA template (1 µl), primers and SYBR® green PCR mix (Applied Biosystems). Relative quantification was done by the ΔΔCT method (--).

Surface exposure of CRT and Mannose-6 Phosphate receptor. Surface exposure of Calreticulin (CRT) and Mannose-6 Phosphate receptor (CD220) was evaluated by staining with monoclonal antibodies specific for CRT (unconjugated, specific for both mouse and human, Abcam ab22683, and PE-conjugated, specific for human only, Abcam, ab83220) and CD220 (Thermo Scientific, MA1-10148) versus isotype controls. Staining for CRT was performed as previously described[64]. Cell viability/membrane integrity probe was used to discriminate/gate between live and dead cells (Life Technologies, L23105).

HMGB1 and LDH Release. HMGB1 and LDH release were evaluated using an HMGB1 detection kit (IBL International, ST51011) and the CYTOTOX96® Non Radioactive Cytotoxicity Assay (Promega, G1780),following manufacturers' instructions.

Western Blotting. Protein lysates from tumor cells treated with Ivermectin were prepared using RIPA buffer. Activation and cleavage of caspases was evaluated using antibodies specific for caspase-1 (NOVUS, NBP1-45433) and caspase-3 (Cell Signaling, 9665). Induction of autophagy was validated using antibodies specific for p62/SQSTM1 (American Res., 03-GP62-C) and LC3 (Cell Signaling, 4599).

Statistical Analysis. Statistical analysis of the data was performed using two-tailed unpaired Student's t-test. Figures depict data representative of at least two independent and similar experiments. Statistically significant differences ($P<0.05$) are shown with asterisks (*).

REFERENCES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

1. Burnstock, G. & Di Virgilio, F. Purinergic signalling and cancer. Purinergic Signal. 9, 491-540 (2013). 2. Pellegatti, P. et al. Increased level of extracellular ATP at tumor sites: in vivo imaging with plasma membrane luciferase. PLoS One. 3, e2599 (2008). 3. Burnstock, G. & Verkhratsky, A. Long-term (trophic) purinergic signalling: purinoceptors control cell proliferation, differentiation and death. Cell Death Dis. 1, e9 (2010). 4. White, N. & Burnstock, G. P2 receptors and cancer. Trends Pharmacol. Sci. 27, 211-217 (2006). 5. Dixon, C. J. et al. Extracellular nucleotides stimulate proliferation in MCF-7 breast cancer cells via P2-purinoceptors. Br. J. Cancer. 75, 34-39 (1997). 6. Adinolfi, E. et al. P2X(7) receptor: Death or life? Purinergic Signal. 1, 219-227 (2005). 7. Adinolfi, E. et al. Expression of P2X7 receptor increases in vivo tumor growth. Cancer Res. 72, 2957-2969 (2012). 8. Sharmeen, S. et al. The antiparasitic agent ivermectin induces chloride-dependent membrane hyperpolarization and cell death in leukemia cells. Blood. 116, 3593-3603 (2010). 9. Drinyaev, V. A. et al. Antitumor effect of avermectins. Eur J Pharmacol. 501, 19-23 (2004). 10. Furusawa, S. et al. Potentiation of Doxorubicin-Induced Apoptosis of Resistant Mouse Leukaemia Cells by Ivermectin. Pharm Pharmacol Comm. 6, 129-134 (2000). 11. Korystov, Y. N. et al. Avermectins inhibit multidrug resistance of tumor cells. Eur J Pharmacol. 493, 57-64 (2004). 12. Hashimoto, H., Messerli, S. M., Sudo, T. & Maruta, H. Ivermectin inactivates the kinase PAK1 and blocks the PAK1-dependent growth of human ovarian cancer and NF2 tumor cell lines. Drug Discov Ther. 3, 243-246 (2009). 13. Melotti, A. et al. The river blindness drug Ivermectin and related macrocyclic lactones inhibit WNT-TCF pathway responses in human cancer. EMBO Mol Med. 6, 1263-1278 (2014). 14. Seil, M. et al. Ivermectin-dependent release of IL-lbeta in response to ATP by peritoneal macrophages from P2X(7)-KO mice. P Purinergic Signal. 6, 405-416 (2010). 15. Selzner, N. et al. Water induces autocrine stimulation of tumor cell killing through ATP release and P2 receptor binding. Cell Death Differ. 11 Suppl 2, S172-180 (2004). 16. Martins, I. et al. Molecular mechanisms of ATP secretion during immunogenic cell death. Cell Death Differ. 21, 79-91 (2014). 17. Okamoto, M. et al. Constitutively active inflammasome in human melanoma cells mediating autoinflammation via caspase-1 processing and secretion of interleukin-lbeta. J Biol Chem. 285, 6477-6488 (2010). 18. Zemkova, H., Tvrdonova, V., Bhattacharya, A. & Jindrichova, M. Allosteric modulation of ligand gated ion channels by ivermectin. Physiological Res. 63 Suppl 1, S215-224 (2014). 19. Bond, T., Basavappa, S., Christensen, M. & Strange, K. ATP dependence of the IC1,swell channel varies with rate of cell swelling. Evidence for two modes of channel activation. J Gen Physiol. 113, 441-456 (1999). 20. Deng, W., Baki, L. & Baumgarten, C. M. Endothelin signalling regulates volume-sensitive Cl-current via NADPH oxidase and mitochondrial reactive oxygen species. Cardiovasc Res. 88, 93-100 (2010). 21. Varela, D. et al. P2X4 activation modulates volume-sensitive outwardly rectifying chloride channels in rat hepatoma cells. J Biol Chem. 285, 7566-7574 (2010). 22. Seil, M., El Ouaaliti, M. & Dehaye, J. P. Secretion of IL-lbeta triggered by dynasore in murine peritoneal macrophages. Innate Immun. 18, 241-249 (2012). 23. Kawano, A. et al. Involvement of P2X4 receptor in P2X7 receptor-dependent cell death of mouse macrophages. Biochemical and biophysical research communications 419, 374-380 (2012). 24. Kawano, A. et al. Regulation of P2X7-dependent inflammatory functions by P2X4 receptor in mouse macrophages. Biochem Biophys Res Commun. 420, 102-107 (2012). 25. Sakaki, H. et al. P2X4 receptor regulates P2X7 receptor-dependent IL-lbeta and IL-18 release in mouse bone marrow-derived dendritic cells. Biochem Biophys Res Commun. 432, 406-411 (2013). 26. Hung, S.C. et al. P2X4 assembles with P2X7 and pannexin-1 in gingival epithelial cells and modulates ATP-induced reactive oxygen species production and inflammasome activation. PloS One. 8, e70210 (2013). 27. Pelegrin, P. & Surprenant, A. Pannexin-1 mediates large pore formation and interleukin-lbeta release by the ATP-gated P2X7 receptor. EMBO J. 25, 5071-5082 (2006). 28. Locovei, S., Scemes, E., Qiu, F., Spray, D. C. & Dahl, G. Pannexinl is part of the pore forming unit of the P2X(7) receptor death complex. FEBS Lett. 581, 483-488 (2007). 29. Leon, D., Hervas, C. & Miras-Portugal, M. T. P2Y1 and P2X7 receptors induce calcium/calmodulin-dependent protein kinase II phosphorylation in cerebellar granule neurons. Eur J Neurosci. 23, 2999-3013 (2006). 30. Gomez-Villafuertes, R. et al. Ca2+/calmodulin-dependent kinase II signalling cascade mediates P2X7 receptor-dependent inhibition of neuritogenesis in neuroblastoma cells. FEBS J. 276, 5307-5325 (2009). 31. Sepulveda, M., Gonano, L. A., Back, T. G., Chen, S. R. & Vila Petroff, M. Role of CaMKII and ROS in rapid pacing-induced apoptosis. J Mol Cell Cardiol. 63, 135-145 (2013). 32. Roe, N. D. & Ren, J. Oxidative activation of Ca(2+)/calmodulin-activated kinase II mediates ER stress-induced cardiac dysfunction and apoptosis. Am J Physiol Heart Circ Physiol. 304, H828-839 (2013). 33. Joiner, M. L. & Koval, O. M. CaMKII and stress mix it up in mitochondria. Front Pharmacol. 5, 67 (2014). 34. Kroemer, G., Galluzzi, L., Kepp, O. & Zitvogel, L. Immunogenic cell death in cancer therapy. Annu Rev Immunol. 31, 51-72 (2013). 35. Sukkurwala, A. Q. et al. Immunogenic calreticulin exposure occurs through a phylogenetically conserved stress pathway involving the chemokine CXCL8. Cell Death Differ. 21, 59-68 (2014). 36. Kim, S. et al. Radiation-induced autophagy potentiates immunotherapy of cancer via up-regulation of mannose 6-phosphate receptor on tumor cells in mice. Cancer Immunol. Immunother. 63, 1009-1021 (2014). 37. Ramakrishnan, R. & Gabrilovich, D. I. The role of mannose-6-phosphate receptor and autophagy in influencing the outcome of combination therapy. Autophagy. 9, 615-616 (2013). 38. Vande Walle, L., Kanneganti, T. D. & Lamkanfi, M. HMGB1 release by inflammasomes. Virulence. 2, 162-165 (2011). 39. Lu, B., Wang, H., Andersson, U. & Tracey, K. J. Regulation of HMGB1 release by inflammasomes. Protein Cell. 4, 163-167 (2013). 40. Michaud, M. et al. Autophagy-dependent anticancer immune responses induced by chemotherapeutic agents in mice. Science. 334, 1573-1577 (2011). 41. Ma, Y., Galluzzi, L., Zitvogel, L. & Kroemer, G. Autophagy and cellular immune responses. Immunity.

39, 211-227 (2013). 42. Miao, E.A., Rajan, J. V. & Aderem, A. Caspase-1-induced pyroptotic cell death. Immunol Rev. 243, 206-214 (2011). 43. Winter, S. E. & Baumler, A. J. Salmonella exploits suicidal behavior of epithelial cells. Front Microbiol. 2, 48 (2011). 44. Qu, Y., Franchi, L., Nunez, G. & Dubyak, G. R. Nonclassical IL-1 beta secretion stimulated by P2X7 receptors is dependent on inflammasome activation and correlated with exosome release in murine macrophages. J Immunol.

179, 1913-1925 (2007). 45. Baroja-Mazo, A. et al. The NLRP3 inflammasome is released as a particulate danger signal that amplifies the inflammatory response. Nat Immunol. 15, 738-748 (2014). 46. Yan, W. et al. High-mobility group box 1 activates caspase-1 and promotes hepatocellular carcinoma invasiveness and metastases. Hepatology. 55, 1863-1875 (2012). 47. Xu, J. et al. Macrophage endocytosis of high-mobility group box 1 triggers pyroptosis. Cell Death Differ. 21, 1229-1239 (2014). 48. Takai, E., Tsukimoto, M., Harada, H. & Kojima, S. Autocrine signaling via release of ATP and activation of P2X7 receptor influences motile activity of human lung cancer cells. Purinergic Signal. 10, 487-497 (2014). 49. Vazquez-Cuevas, F.G. et al. Paracrine stimulation of P2X7 receptor by ATP activates a proliferative pathway in ovarian carcinoma cells. J Cell Biochem. 115, 1955-1966 (2014). 50. Derangere, V. et al. Liver X receptor beta activation induces pyroptosis of human and murine colon cancer cells. Cell Death Differ. 21, 1914-1924 (2014). 51. Bergsbaken, T., Fink, S. L. & Cookson, B. T. Pyroptosis: host cell death and inflammation. Nat Rev Microbiol. 7, 99-109 (2009). 52. Lamkanfi, M. Emerging inflammasome effector mechanisms. Nat Rev Immunol. 11, 213-220 (2011). 53. Shao, W., Yeretssian, G., Doiron, K., Hussain, S. N. & Saleh, M. The caspase-1 digestome identifies the glycolysis pathway as a target during infection and septic shock. J Biol Chem. 282, 36321-36329 (2007). 54. Cerella, C., Diederich, M. & Ghibelli, L. The dual role of calcium as messenger and stressor in cell damage, death, and survival. Int J Cell Biol. 2010, 546163 (2010). 55. Zhang, W. H. et al. Fundamental role of the Rip2/caspase-1 pathway in hypoxia and ischemia-induced neuronal cell death. Proc Natl Acad Sci USA. 100, 16012-16017 (2003). 56. Hoyer-Hansen, M. et al. Control of macroautophagy by calcium, calmodulin-dependent kinase kinase-beta, and Bcl-2. Mol Cell. 25, 193-205 (2007). 57. Young, C. et al. A novel mechanism of autophagic cell death in dystrophic muscle regulated by P2RX7 receptor large-pore formation and HSP90. Autophagy. 11, 113-130 (2015). 58. Blander, J. M. A long-awaited merger of the pathways mediating host defence and programmed cell death. Nat Rev Immunol. 14, 601-618 (2014). 59. de Oliveira, S. et al. ATP modulates acute inflammation in vivo through dual oxidase 1-derived H2O2 production and NF-kappaB activation. J Immunol. 192, 5710-5719 (2014). 60. Pettigrew, C. A., Clerkin, J. S. & Cotter, T. G. DUOX enzyme activity promotes AKT signalling in prostate cancer cells. Anticancer Res. 32, 5175-5181 (2012). 61. Flentke, G. R., Garic, A., Hernandez, M. & Smith, S. M. CaMKII represses transcriptionally active beta-catenin to mediate acute ethanol neurodegeneration and can phosphorylate beta-catenin. J Neurochem. 128, 523-535 (2014). 62. Junger, W. G. Immune cell regulation by autocrine purinergic signalling. Nat Rev Immunol. 11, 201-212 (2011). 63. Ghiringhelli, F. et al. Activation of the NLRP3 inflammasome in dendritic cells induces IL-lbeta-dependent adaptive immunity against tumors. Nat Med. 15, 1170-1178 (2009). 64. Panaretakis, T. et al. Mechanisms of pre-apoptotic calreticulin exposure in immunogenic cell death. EMBO J. 28, 578-590 (2009).

What is claimed is:

1. A method of treating breast cancer in a patient in need thereof, the method comprising administering to the patient a therapeutically effective amount of a macrocyclic lactone, or a pharmaceutically acceptable salt thereof, and a therapeutically effective amount of an anti-cancer immunostimulant, wherein the macrocyclic lactone is ivermectin and the anti-cancer immunostimulant is a PD-1 inhibitor or a PD-L1 inhibitor.

2. The method of claim 1, wherein the cancer is triple negative breast cancer.

3. The method of claim 1, wherein the anti-cancer immunostimulant is a PD-1 inhibitor.

4. A pharmaceutical composition comprising a macrocyclic lactone, or pharmaceutically acceptable salt thereof, a second agent, and a pharmaceutically acceptable excipient, wherein the macrocyclic lactone is ivermectin and the second agent is a PD-1 inhibitor or a PD-L1 inhibitor; and
   wherein the macrocyclic lactone is present in a therapeutically effective amount to treat breast cancer and the second agent is present in a therapeutically effective amount to treat breast cancer.

5. The pharmaceutical composition of claim 4, wherein the second agent is a PD-1 inhibitor.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 1
tggatgacaa gaacacggat g                                    21

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
caggatgtca aaacggatgc                                      20